US008022043B2

(12) United States Patent
Porcelli

(10) Patent No.: US 8,022,043 B2
(45) Date of Patent: *Sep. 20, 2011

(54) CERAMIDE DERIVATIVES AS MODULATORS OF IMMUNITY AND AUTOIMMUNITY

(75) Inventor: Steven A. Porcelli, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1016 days.

This patent is subject to a terminal disclaimer.

(21) Appl. No.: 11/785,988

(22) Filed: Apr. 23, 2007

(65) Prior Publication Data

US 2007/0238673 A1 Oct. 11, 2007

Related U.S. Application Data

(63) Continuation-in-part of application No. 11/211,653, filed on Aug. 26, 2005, now Pat. No. 7,772,380.

(60) Provisional application No. 60/605,362, filed on Aug. 27, 2004.

(51) Int. Cl.
*A61K 31/70* (2006.01)
(52) U.S. Cl. .......................... 514/25; 536/17.9
(58) Field of Classification Search .................. None
See application file for complete search history.

(56) References Cited

U.S. PATENT DOCUMENTS

| 5,679,347 | A | 10/1997 | Porcelli et al. |
| 5,780,441 | A | 7/1998 | Higa et al. |
| 5,849,716 | A | 12/1998 | Akimoto et al. |
| 5,853,737 | A | 12/1998 | Modlin et al. |
| 5,936,076 | A | 8/1999 | Higa et al. |
| 6,162,609 | A | 12/2000 | Hafler et al. |
| 6,238,676 | B1 | 5/2001 | Porcelli et al. |
| 6,531,453 | B1 | 3/2003 | Taniguchi et al. |
| 6,747,010 | B2 | 6/2004 | Taniguchi et al. |
| 2003/0157135 | A1 | 8/2003 | Tsuji et al. |
| 2004/0127429 | A1 | 7/2004 | Tsuji |
| 2006/0052316 | A1 | 3/2006 | Porcelli |
| 2006/0116331 | A1 | 6/2006 | Jiang et al. |

OTHER PUBLICATIONS

Bendelac, A.: "Mouse NK+T cells," *Current Opinion in Immunology*, 1995, vol. 7: pp. 367-374.
Bendelac, A., et al., "CD1 Recognition by Mouse NK1+ T lymphocytes," *Science*, May 12, 1995, vol. 268: pp. 861-863.
Bendelac, A., et al., "Mouse CD-1-Specific NK1 T Cells: Development, Specificity , and Function, " *Annual Review Immunol*, 1997, vol. 15: pp. 535-562.
Benlagha, K., et al., "InVivo Identifcation of Glycolipid Antigen-specific T Cells Using Flourescent CD1d Tetramers," Jun. 5, 2000, vol. 191, No. 11: pp. 1895-1903.
Burdin, N., et al., "Immunization with α-galactosylceramide polarizes CD-1-reactive NK T cells toward Th2 cytokine synthesis," *Eur. J. Immunol*, 1999, vol. 29: pp. 2014-2025.

Bynoe, M.S., et al., "Characterization of anti-DNA B cells that escape negative selection," *Eur. J. Immunol*, 1999, vol. 29: pp. 1304-1313.
Bynoe, M.S., et al., "Estrogen up-regulates Bcl-2 and blocks tolerance induction of naive B cells " *Proc. Natl. Acad. Sci. U.S.A.*, Mar. 14, 2000 vol. 97, Issue 6: pp. 2703-2708.
Crowe, Nadine Y., et al., "Glycolipid Antigen Drives Rapid Expansion and Sustained Cytokline Production by NK T Cells," *The Journal of Immunology*, 2003, vol. 171: pp. 4020-4027.
Davodeau, François, et al., "Close Phenotypic and Functional Similarities Between Human and Murin αβ T Cells Expressing Invariant TCR α-Chains," *The Journal of Immunology*, 1997, vol. 158: pp. 5603-5611.
Erbel G., et al., "Rapid Death and Regeneration of NKT Cells in Anti-CD3ε- or IL-12-Treated Mice: A Major Role for Bone Marrow in NKT Cell Homeostasis," *Immunity*, Sep. 1998, vol. 9, pp. 345-353.
Exley, M. J., et al., "Requirements for CD1d Recognition by Human Invariant Vα24+ DC4-CD8-T Cells " *J. Exp. Med.*, Jul. 7, 1997, vol. 186: pp. 109-120.
Gaynor, B., et al., "Peptide inhibition of glomerular deposition pf an anti-DNA antibody," *Proc. Natl. Acad. Sci. U.S.A.*, Mar. 1997, vol. 94: pp. 1955-1960.
Godfrey, D.I., et al., "NKT cells: facts, functions and fallacies," *Immunol Today*, Nov. 2000, vol. 21, No. 11: pp. 573-583.
Hahn, B. H., "Antibodies to DNA," *New England Journal of Medicine* , May 7, 1998, vol. 338, No. 19: pp. 1359-1368.
Hammond, K.J.L., et al., "αβ-T Cell Receptor (TCR)+DC4-CD8- (NKT) Thymocytes Prevent Insulin-dependent Diabetes Mellitus in Nonobese Diabetic (NOD)/Lt Mice by the Influence of Interleukin (IL)-4 and/or IL-10 " *J. Exp. Med.*, Apr. 6, 1998, vol. 187, No. 7: pp. 1047-1056.
Hong, S, et al., "The natural killer T-cell ligand α-galactosylcermide prevents autoimmune diabetes in non-obese diabetic mice," *Nature Medicine*, Sep. 2001, vol. 7, No. 9: pp. 1052-1056.
Iijima, H., et al., "Structure-Activity Relationship and Conformational Analysis of Monoglycosylceramides on the Syngeneic Mixed Leukocyte Reaction," *Bioorganic & Medicine Chemistry*, 1998, vol. 6: pp. 1905-1910.

(Continued)

*Primary Examiner* — Elli Peselev

(74) *Attorney, Agent, or Firm* — Sterne, Kessler, Goldstein & Fox P.L.L.C.

(57) ABSTRACT

α-Galactosylceramides and glycosylceramides ("ceramide-like glycolipids") that modulate NK T cells. The ceramide-like glycolipids vary in the cytokines induced in NK T cells and vary in the antigen-presenting cells that are capable of efficiently presenting the compounds to NK T cells. Pharmaceutical compositions of the ceramide-like glycolipids are provided, as are pharmaceutical compositions of the ceramide-like glycolipids combined with dendritic cells. Methods utilizing the ceramide-like glycolipids in vaccines, to activate NK T cells, to stimulate the immune system, and to treat mammals are also provided. The invention also provides methods of evaluating a compound for its ability to activate an NK T cell in the presence of a cell expressing a CD1d protein.

54 Claims, 34 Drawing Sheets

OTHER PUBLICATIONS

Inoue, H. et al., "α-Galactosylcermide (AGL-517) treatment protects mice from lethal irradiation " *Experimental Hematology*, 1997, vol. 25: pp. 935-944.

Joyce, S., et al., "Natural Ligand of Mouse CD1d1: Cellular Glycosylphosphatidylinositol," *Science* Mar. 6, 1998, vol. 279: pp. 1541-1544.

Kawano, T., et al., "CD1d-Restricted and TCR-Meditated Activation of $V_\alpha 14$ NKT Cells by Glycosylceramides," *Science*, Nov. 28, 1997, vol. 278: pp. 1626-1629.

Kobayashi, E., et al., "Enhancing Effects of α-, β-Monoglycosylcermides on Natural Killer Cell Activity," *Bioorganic & Medicinal Chemistry*, 1996, vol. 4, No. 4,: pp. 615-619.

Kobayashi, E., et al.. "Enhancing effects of agelasphon-11 on natural killer cell activities of normal and tumor-bearing mice," *Biol. Pharm Bull.*, Mar. 1996, vol. 19, No. 3: pp. 335-486.

Koboyashi, E., et al., " KRN7000, A Novel Immunomodulator, and Its Anittumor Activities," *Oncology Research*, 1995, vol. 7, Nos. 10/11: pp. 529-534.

Kojo, S., et al., "Dysfunction of T Cell Receptor AV24AJ18+,BV11+ Double-Negative Regulatory Natural Killer T Cells in Autoimmune Diseases," *Arthritis & Rheumatism*, May 2001, vol. 44, No. 5: pp. 1127-1138.

Koseki, H., et al., "Dominant expression of a distinctive V14+ T-cell antigen receptor α chain in mice " *Proc. Natl. Acad. Sci. U.S.A.*, Sep. 1991, vol. 888: pp. 7518-7522.

Kotzin, B. L., et al. "Systemic Lupus Erythematosus," *Cell*, May 3, 1996, vol. 85: pp. 303-306.

Kuo, P., et al., "Bcl-2 leads to expression of anti-DNA B cells but no nephritis: a model for a clinical subset," *Eur. J. Immumol*, 1999, vol. 29: pp. 3168-3178.

Laloux, V., et al., "NK T Cell-Induced Protection Against Diabetes in $V\alpha 14$-$J\alpha 281$ Transgenic Nonobese Diabetic Mice Is Associated with a TH2 Shift Circumscribed Regionally to the Islets and Functionally to Islet Autoantigen," *Journal of Immunology*, 2001, vol. 166: pp. 3749-3756.

Matsuda, J. L., et al., "Tracking the Response of Natural Killer T Cells to a Glycolipid Antigen Using CD1d Tetramers," *J. Exp. Med.*, Sep. 3, 2000, vol. 192, No. 5: pp. 741-753.

Mieza, M. A., et al., "Selective Reduction of $V\alpha 14+$ NK T Cells Associated with Disease Development in Autoimmune-Prone Mice," *Journal of Immunology*, 1996, vol. 156: pp. 4035-4040.

Miyamoto, K. et al., "A synthetic glycolipid prevents autoimmune encephalamyelitis by inducing $T_H 2$ bias of natural killer T cells," *Nature*, Oct. 2000, vol. 413: pp. 531-534.

Moody, D.B., et al., "The molecular basis of CD1-medicated presentation of lipid antigens," *Immunol. Rev.*, Dec. 1999, vol. 172: pp. 285-296.

Morita, M., et al., "Structure Relationship of α-Galactosylceramides against B-16-Bearing," *J. Med. Chem.*, 1995, vol. 38: pp. 2176-2187.

Motoki, M.K., et al., Effects of alpha-galactosylceramides on bone marrow cells in vitro and hematopoiesis in vivo, *Biological & Pharmceutical Bulletin*, Jul. 1996, vol. 19, No. 7: pp. 952-955.

Motoki, K., et al., "Immunostimulatory and a antitumor activities of monoglycosylceramides having various sugar moieties," *Biological & Pharacuetical Bulletin*, Nov. 1995, vol. 18, No. 11: pp. 1487-1491.

Naidenko, O.V., et al., "Binding and antigen Presentation of Ceramide-containing Glycolipids by Soluble Mouse and Human CD1d Molecules," *J. Exp. Med.*, Oct. 18, 1999, vol. 190, No. 8: pp. 1069-1079.

Nakagawa, R., et al., "Antitumor activity of alpha-galactosylceramide, KRN7000, in mice with EL-4 hepatic metastasis and its cytokine production," *Oncology Research*, 1998, vol. 10: pp. 561-568.

Nakagawa, R., et al., "Antitumor activity of alpha-galactosylceramide, KRN7000, in mice with the melanoma B16 hepatic metastasis and immunohistological study of tumor infiltrating cells," *Oncology Research*, 2000, vol. 12: pp. 51-58.

Oishi, Y., et al., "Selective reduction and recovery of invariant Valpha24JalphaQ T cell receptor T cells in correlation with disease activity in patients with systemic lupus erythematosus," *Journal of Rheumatology*, Feb. 2001, vol. 28, No. 2: pp. 275-283.

Pisetsky, D.S., "Systemic lupus erythematosus. Diagnosis and treatment " *The Medical Clinics of North America: Advances in Rheumatology*, Jan. 1997, vol. 81, No. 1: pp. 113-128.

Porcelli, S.A., "The CD1 family: a third lineage of antigen-presenting molecules." *Advances in Immunology*, 1995, vol. 59: pp. 1-98.

Porcelli, S.A., et al., "The CD1 System: Antigen-Presenting Molecules for T Cell Recognition of Lipids and Glycolipids," *Ammu. Rev. Immunol.* 1999, vol. 17: pp. 297-329.

Porcelli, S.A., et al., "Analysis of T Cell Antigen Receptor (TCR) Expression by Human Peripheral Blood CD4-8—αβ T Cells Demonstrates Preferential Use of Several Vβ Genes and an Invariant TCR α Chain," *J. Exp. Med.*, Jul. 1993, vol. 178: pp. 1-16.

Porcelli, S. A., et al., "The CD1 family of lipid antigen-presenting molecules," *Review Immunology Today*, Aug. 1998, vol. 19, No. 8: pp. 362-368.

Putterman, C., et al., "Immunization with a Peptide Surrogate for Double-stranded DNA (dsDNA) Induces Autoantibody Production and Renal Immunoglobulin Deposition," *J. Exp. Med.*, Jul. 6, 1998, vol. No. 1: pp. 29-38.

Putterman, C., et al., "Molecular Analysis of the Autoantibody Response in Peptide-Induced Autoimmunity," *The Journal of Immunology*, 2000, vol. 164: pp. 2542-2549.

Sharif, S., et al., "Activation of natural killer T cells by α-galactosyceramide treatment prevents the onset and recurrence of autoimmune Type 1 diabetes," *Nature Medicine*, Sep. 2001, vol .7, No. 9: pp. 1057-1062.

Sharif, S., et al., "Regulation of autoimmune disease by natural killer T cells," *Journal of Molecular Medicine*, May 2002, vol. 80, No. 5: pp. 290-300.

Sidobre, S., et al., "The $V\alpha 14$ NKT Cell TCR Exhibits High-Affinity Binding to a Glycolipid/CD1d Complex," *The Journal of lmmunology*, 2002, vol. 169: pp. 1340-1348.

Sieling, P. A., et al., Human Double-Negative T Cells in Systematic Lupus Erythematosus Provide Help for IgG and Are Restricted by CD1c, *J. Immunol.*, 2000, vol. 165: pp. 5338-5344.

Smyth, M. J., et al., "NKT cells and tumor immunity-a double-edged sword," *Nature Immunology*, Dec. 2000, vol. 1, No. 6: pp. 459-460.

Spada, F.M., et al., "CD1d-restricted Recognition of Synthetic Glycolipid Antigens by Human Natural Killer T Cells," *J. Exp. Med.*, Oct. 19, 1998, vol. 188, No. 8: pp. 1529-1534.

Spatz, L., et al., "Light Chain Usage in Anti-double-stranded DNA B Cell Subsets: Role in Cell Fate Determination," Apr. 7, 1997, vol. 185, No. 7: pp. 1317-1326.

Sumida, T., et al., "Selective Reduction of T Cells Bearing Invariant $V\alpha 24 J\alpha Q$ Antigen Receptor in Patients with Systemic Sclerosis," *J. Exp. Med.*, Oct. 1995, vol. 182: pp. 1163-1168.

Takeda, K., et al., "The Development of Autoimmunity in C57BL/6 *Ipr* ice Correlates with the Disappearance of Natural Killer Type 1-positive Cells: Evidence for Their Suppressive Action on Bone Marrow Stem Cell Proliferation, B Cell Immunoglobulin Secretion, and Autoimmune Symptoms," *Journal Exp. Medical*, Jan. 1993, vol. 177: pp. 155-164.

Uchimura, A., et al. , "Immunostimulatory Activities of Monoglycosylated α-D-Pyranosylceramides " *Biorganic & Medicinal Chemistry*, 1997, vol. 5, No. 12: pp. 2245-2249.

Uchimura, A. et al., "Immunostimulatory Activties of Mono- or Diglycosylated α-Galactosyceramides," *Biorganic & Medicinal Chemistry*, 1997, vol. 5, No. 7: pp. 1447-1452.

Wang, B., et al., "Cd-1 restricted NK T Cells Protect Nonobese Diabetic Mice from Developing Diabetes," *J. Exp. Med.* , Aug. 6, 2001, vol. 194, No. 3: pp. 313-319.

Wilson, S.B., et al., "Extreme Th1 bias of invariant $V\alpha 24 J\alpha Q$ T cells in type 1 diabetes," *Nature*, Jan. 8, 1998, vol. 391: pp. 177-181.

Yamaguchi, Y., et al., "Enhancing Effects of (2S,3S,4R)-1-O-(alpha-D-galactopyranosyl)-2-(N-hexacosanoylamino)-1,3,4-octadecanetriol (KRN7000) on antigen-presenting cells and antimetastatic activity of KRN7000-pretreated antigen-presenting cells and antimetastatic activity of KRN7000-pretreated antigen-presenting cells," *Oncology Research*, 1996, vol. 8, Nos. 10/11: pp. 399-407.

Yoshimoto, T., et al., "CD4$^{pos}$, NK1.1$^{pos}$ T Cells Promptly Produce Interleukin 4 in Response to In Vivo Challenge with Anti-CD3," *The Journal of Experimental Medicine*, Apr. 1994, vol. 179: pp. 1285-1295.

Yoshimoto, T., et al., "Role of NK.1$^+$Cells in a T$_H$2 Response and in Immunoglobulin E Production," *Science*, Dec. 15, 1995, vol. 270, Issue 5243: pp. 1845-1847.

Yoshimoto, T., et al., "Defective IgE production by SJL mice is linked to the absence of CD4$^+$, NK1.1$^+$T cells that promptly produce interleukin 4," *Proc. Natl. Acad. Sci. USA*, Dec. 1995, vol. 92: pp. 11931-11934.

Zeng, Z.-H., et al., "Crystal Structure of Mouse CD1: An MHC-like Fold with a Large Hydrophobic Binding Groove," *Science*, Jul. 18, 1997, vol. 277:pp. 339-345.

Zeng, D., et al., "Cutting Edge: A Role for CD1 in the Pathogenesis of Lupus in NZB/NZW Mice," *J. Immunol.*, 2000, vol. 164: pp. 5000-5004.

Bhat, S., et al., "Galactosyl ceramide or a derivative is an essential comoponent of the neural receptor for human immunodeficiency virus type 1 envelope glycoprotein gp120," *Proc. Natl. Acad. Sci.*, 88:7131-7134, Neurobiology, United States (1991).

Yu, K.O., et al., "Modulation of CD1d-restricted NKT cell responses by using N-acyl variants of a-galactosylceramides," *Proc. Natl. Acad. Sci.*, 102:3383-3388, National Academy of Sciences, United States (2005).

Office Action mailed Oct. 4, 2007, in U.S. Appl. No. 11/211,653, Porcelli, filed Aug. 26, 2005.

Office Action mailed Jun. 4, 2008, in U.S. Appl. No. 11/211,653, Porcelli, filed Aug. 26, 2005.

Office Action mailed Jan. 29, 2009, in U.S. Appl. No. 11/211,653, Porcelli, filed Aug. 26, 2005.

Office Action mailed Apr. 17, 2009, in U.S. Appl. No. 11/211,653, Porcelli, filed Aug. 26, 2005.

Office Action mailed Nov. 9, 2009, in U.S. Appl. No. 11/211,653, Porcelli, filed Aug. 26, 2005.

International Search Report for International Application No. PCT/US08/04546, United States Patent and Trademark Office, U.S.A., mailed on Jul. 30, 2008.

FIG. 5B1
YTC03 COMPOUNDS
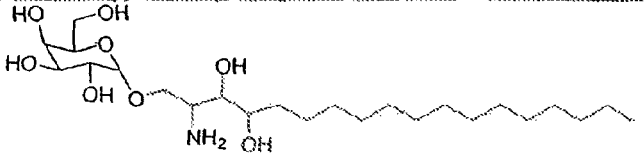

FIG. 5B2
YTC03 COMPOUNDS
| 4 | 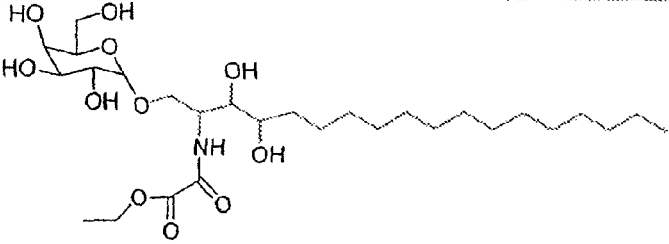 Mol. Wt.: 579.72 |
| --- | --- |
| 5 | 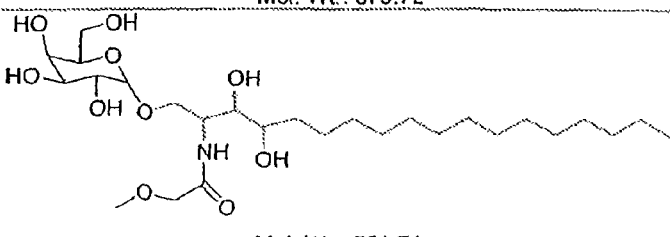 Mol. Wt.: 551.71 |
| 6 | 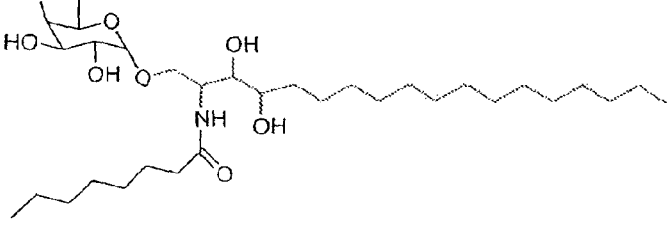 Mol. Wt.: 605.84 |
| 7 | 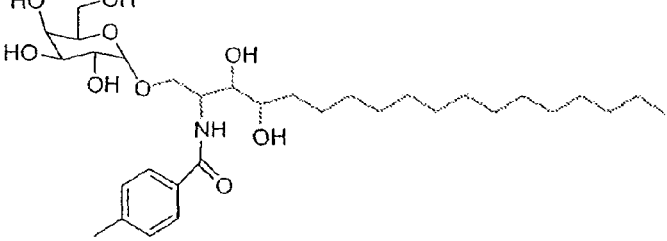 Mol. Wt.: 597.78 |
| 8 | 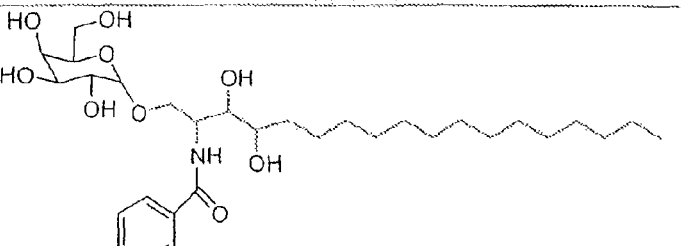 Mol. Wt.: 652.64 |

FIG. 5B3
YTC03 COMPOUNDS
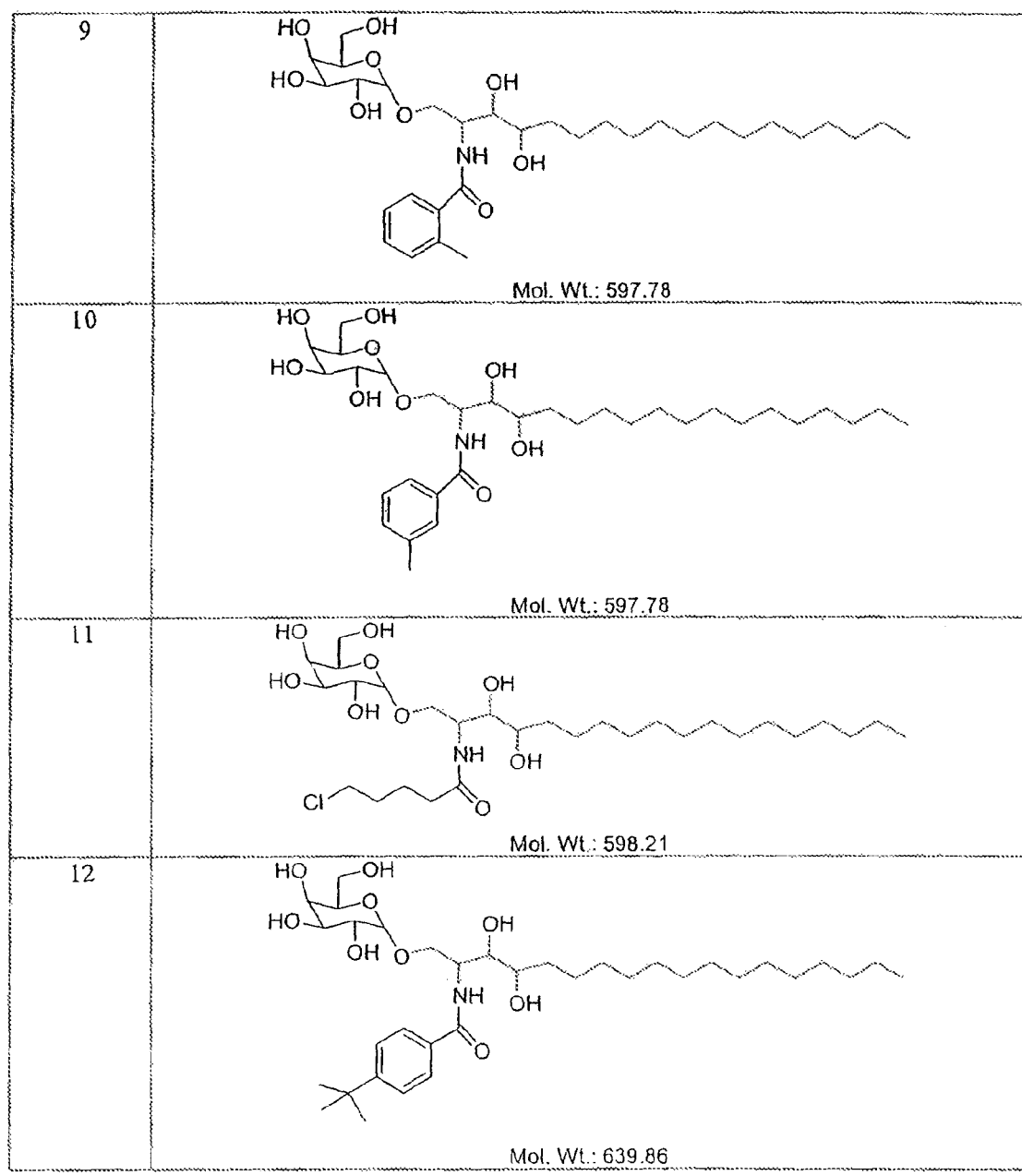

FIG. 5B4
YTC03 COMPOUNDS
| 13 | 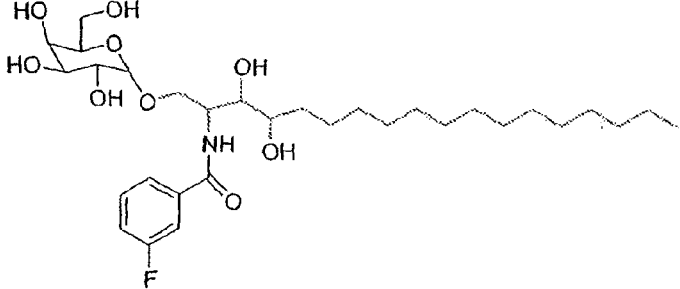<br>Mol. Wt.: 601.74 |
| --- | --- |
| 14 | 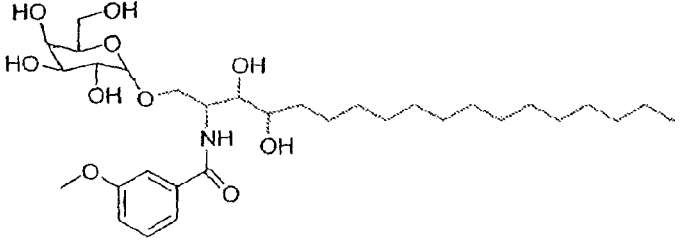<br>Mol. Wt.: 613.78 |
| 15 | 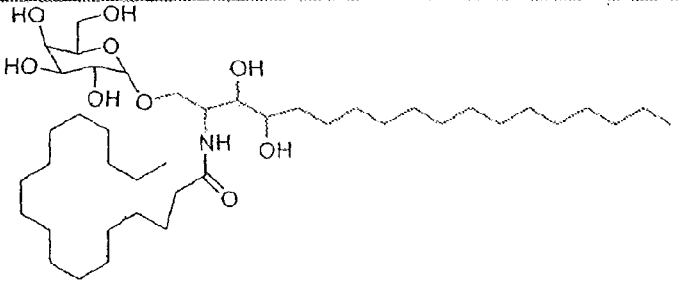<br>Mol. Wt.: 746.11 |
| 16 | 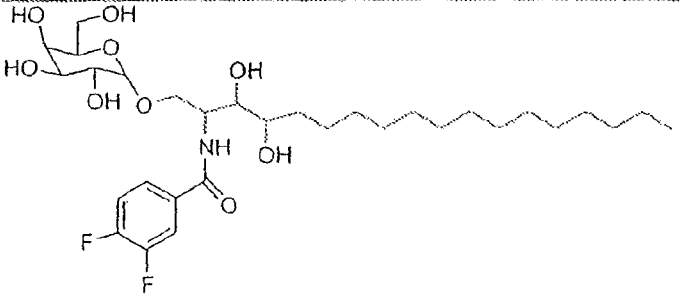<br>Mol. Wt.: 619.73 |

FIG. 5B5
YTC03 COMPOUNDS
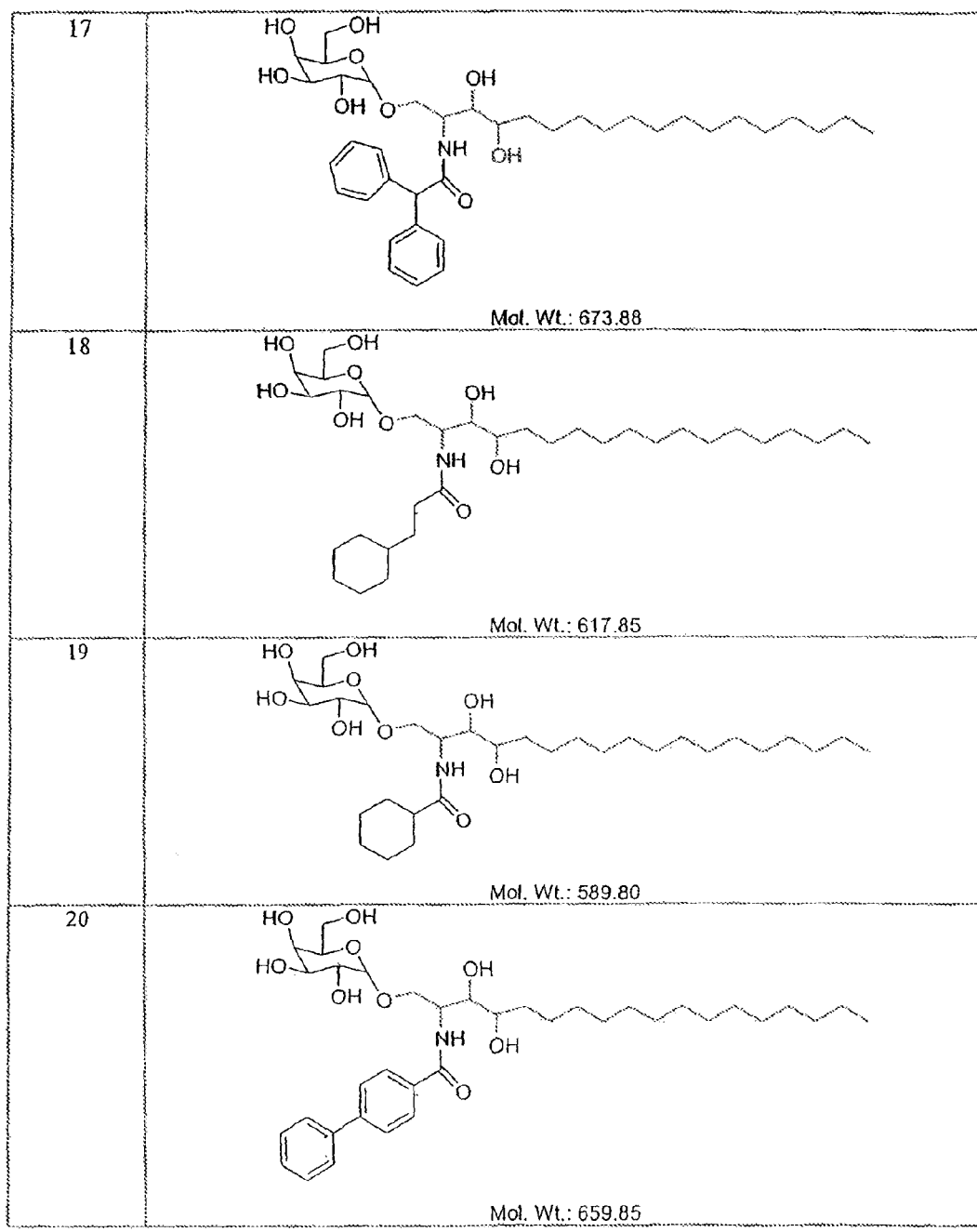

FIG. 5B6
YTC03 COMPOUNDS
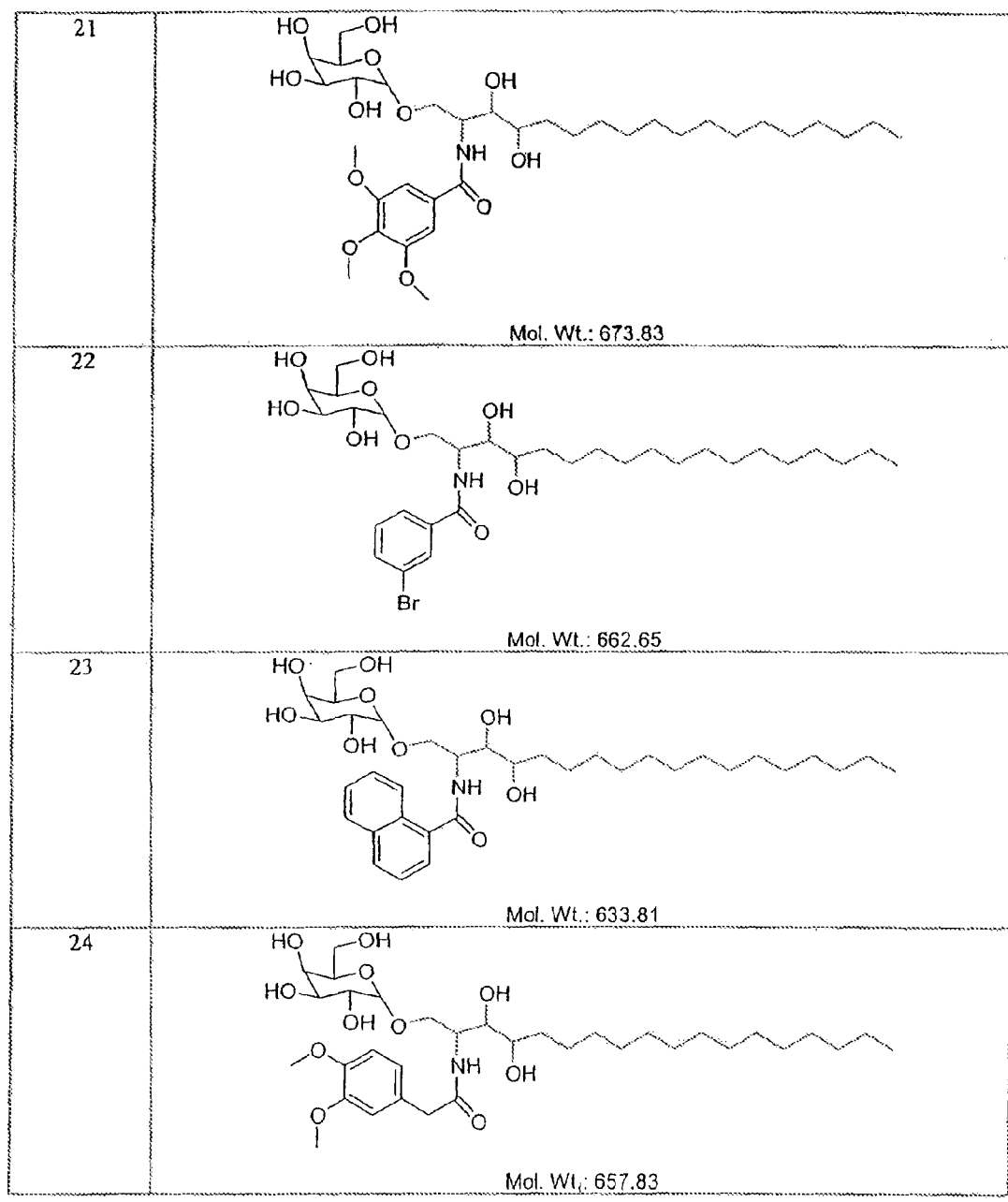

FIG. 5B7
YTC03 COMPOUNDS
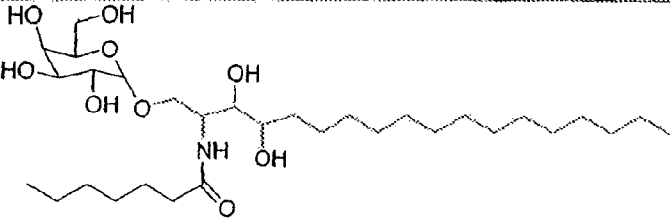

FIG. 5B8
YTC03 COMPOUNDS
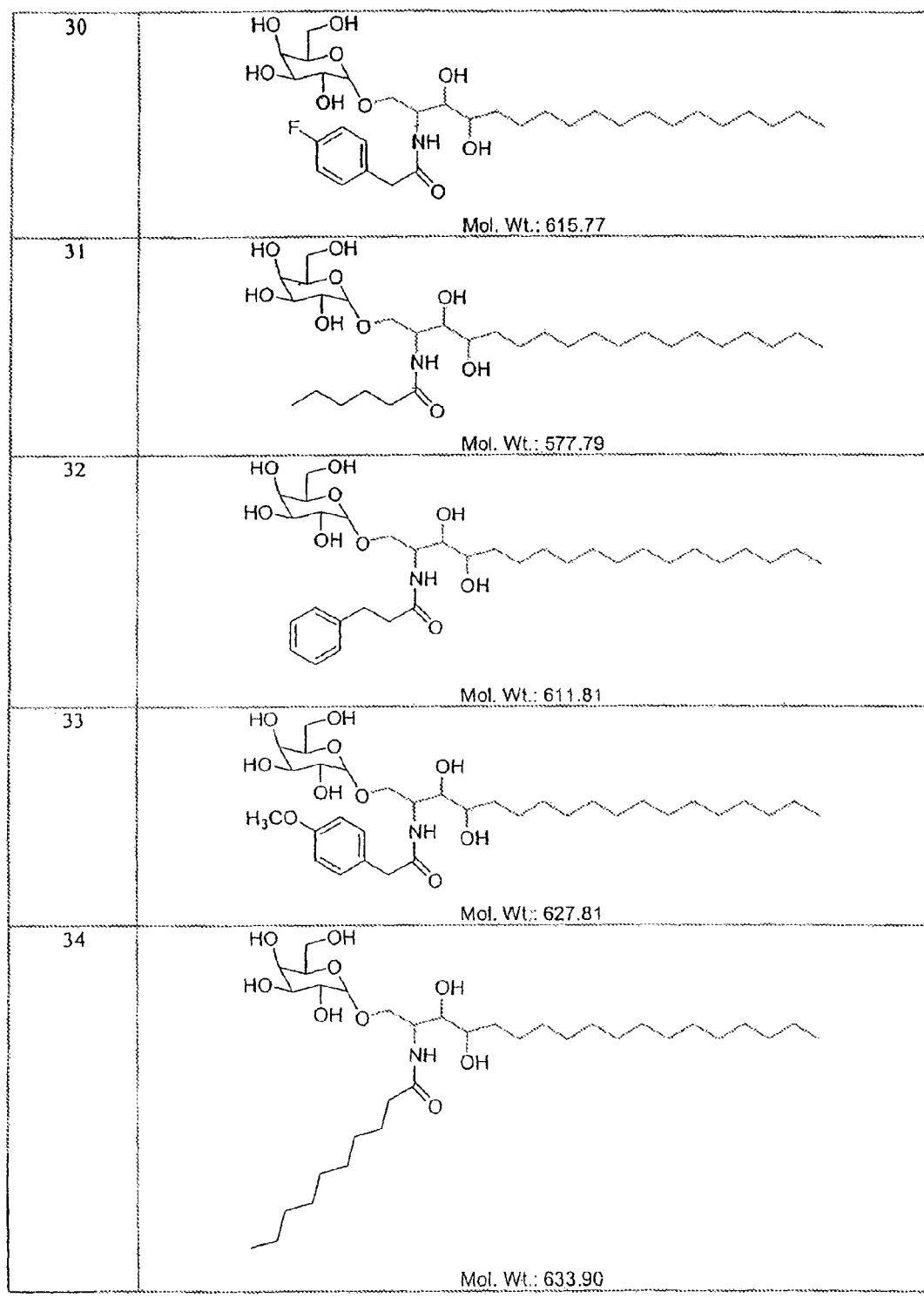

FIG. 5B9
YTC03 COMPOUNDS
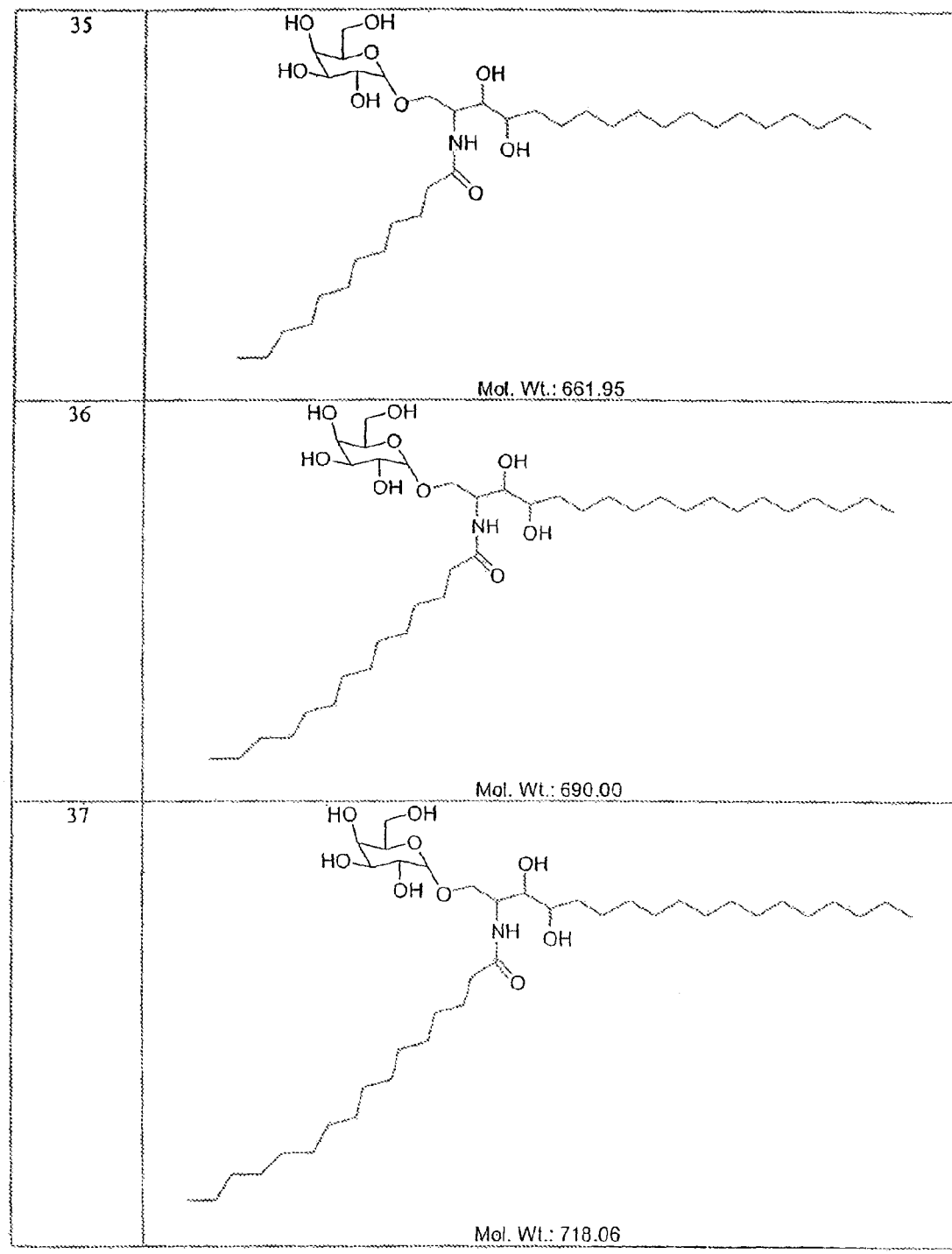

FIG. 5B10
YTC03 COMPOUNDS
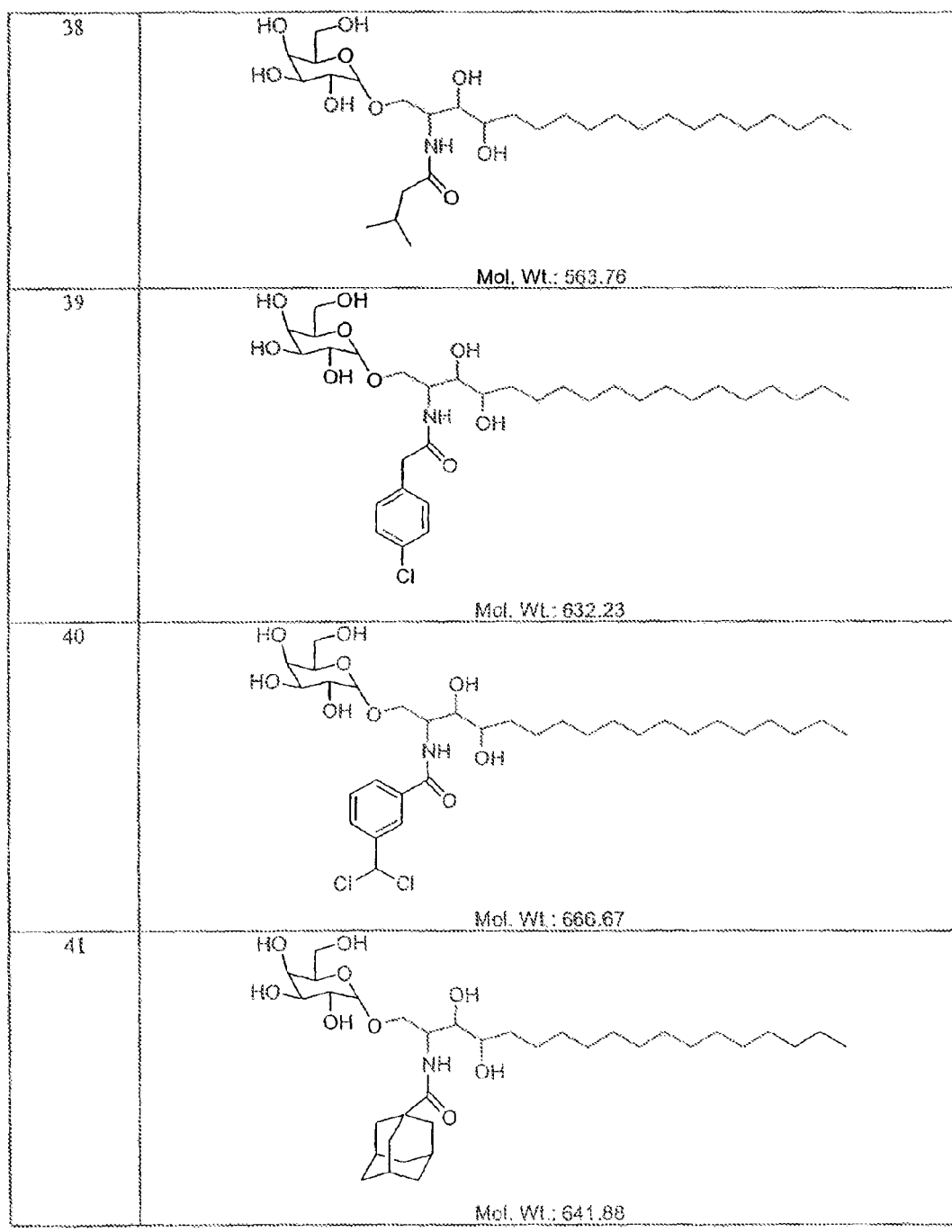

FIG. 5B11
YTC03 COMPOUNDS
| # | Structure |
|---|---|
| 42 | 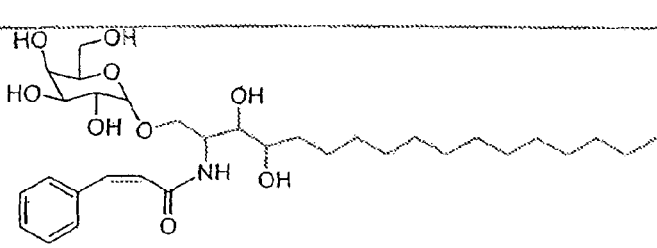<br>Exact Mass: 609.39 |
| 43 | 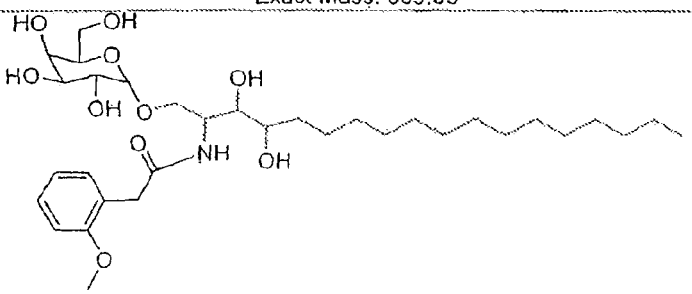<br>Exact Mass: 627.40 |
| 44 | 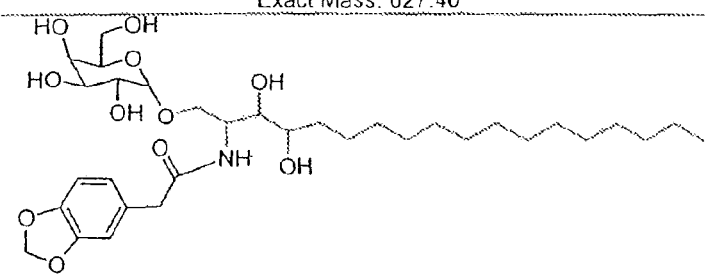<br>Exact Mass: 641.38 |
| 45 | 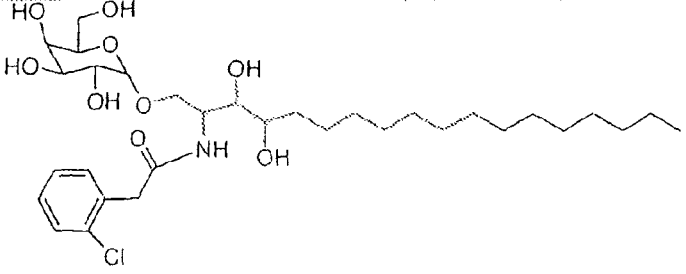<br>Exact Mass: 631.35 |

FIG. 5B12
YTC03 COMPOUNDS
| 46 | 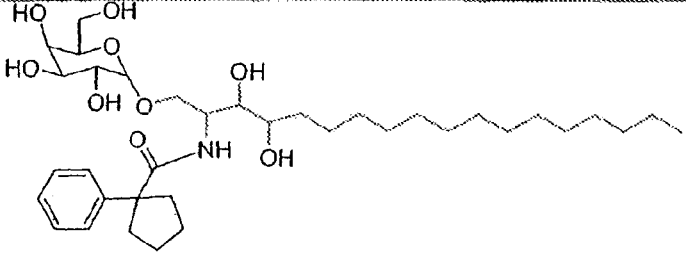 Exact Mass: 651.43 |
| --- | --- |
| 47 | 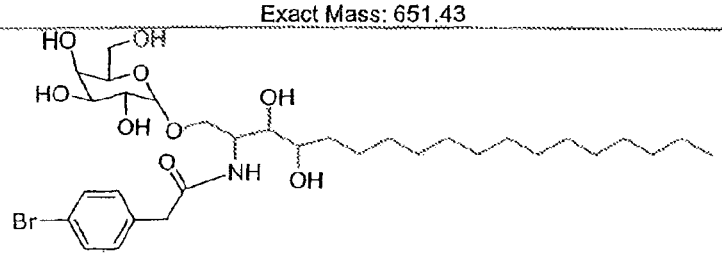 Exact Mass: 675.30 |
| 48 | 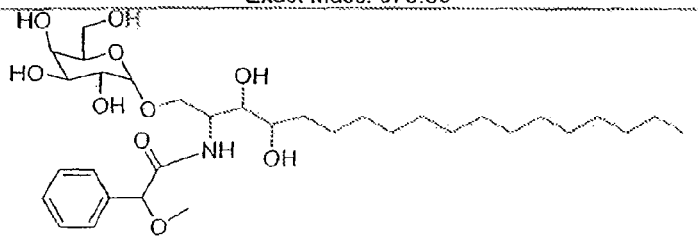 Exact Mass: 627.40 |
| 49 | 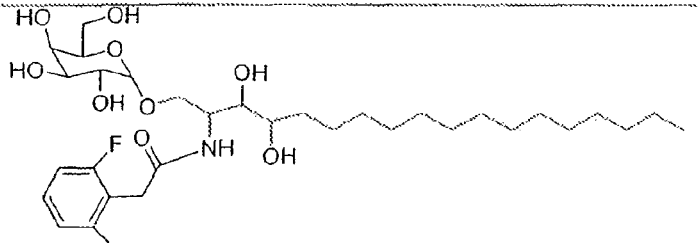 Exact Mass: 649.34 |
| 50 | 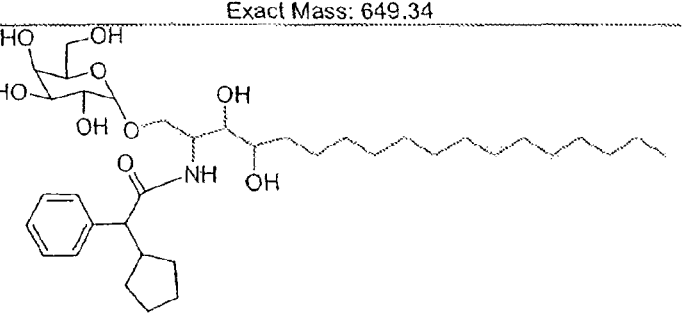 Exact Mass: 665.45 |

FIG. 5B13
YTC03 COMPOUNDS
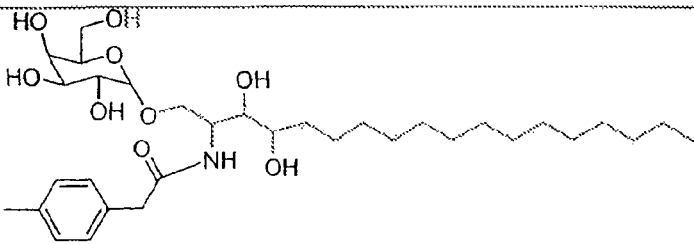
51 — Exact Mass: 611.40
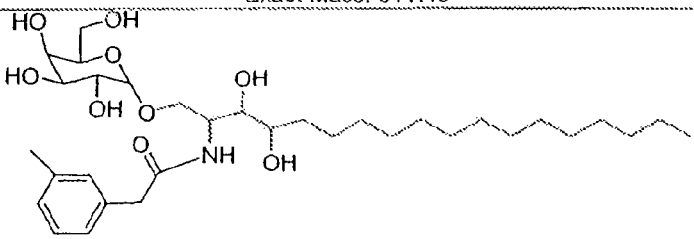
52 — Exact Mass: 611.40
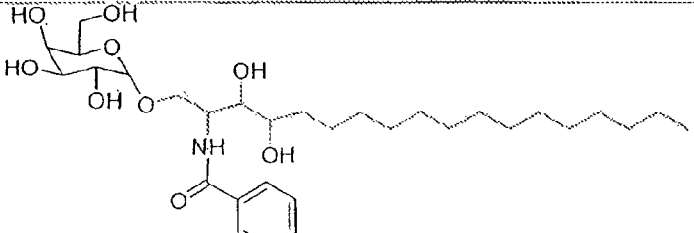
53 — Exact Mass: 697.48
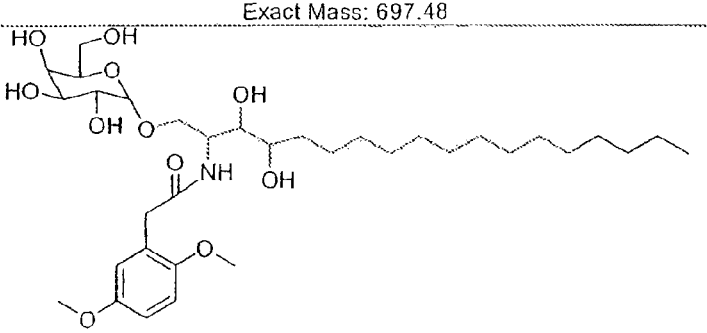
54 — Exact Mass: 657.41
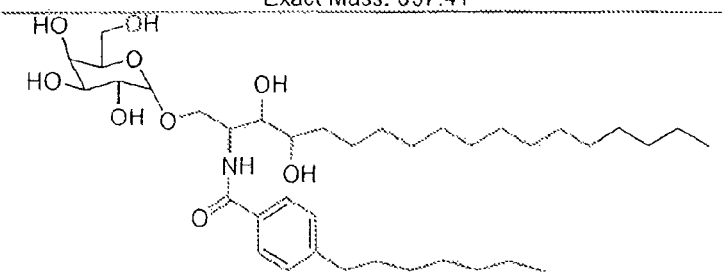
55 — Exact Mass: 681.48

FIG. 5B14
YTC03 COMPOUNDS
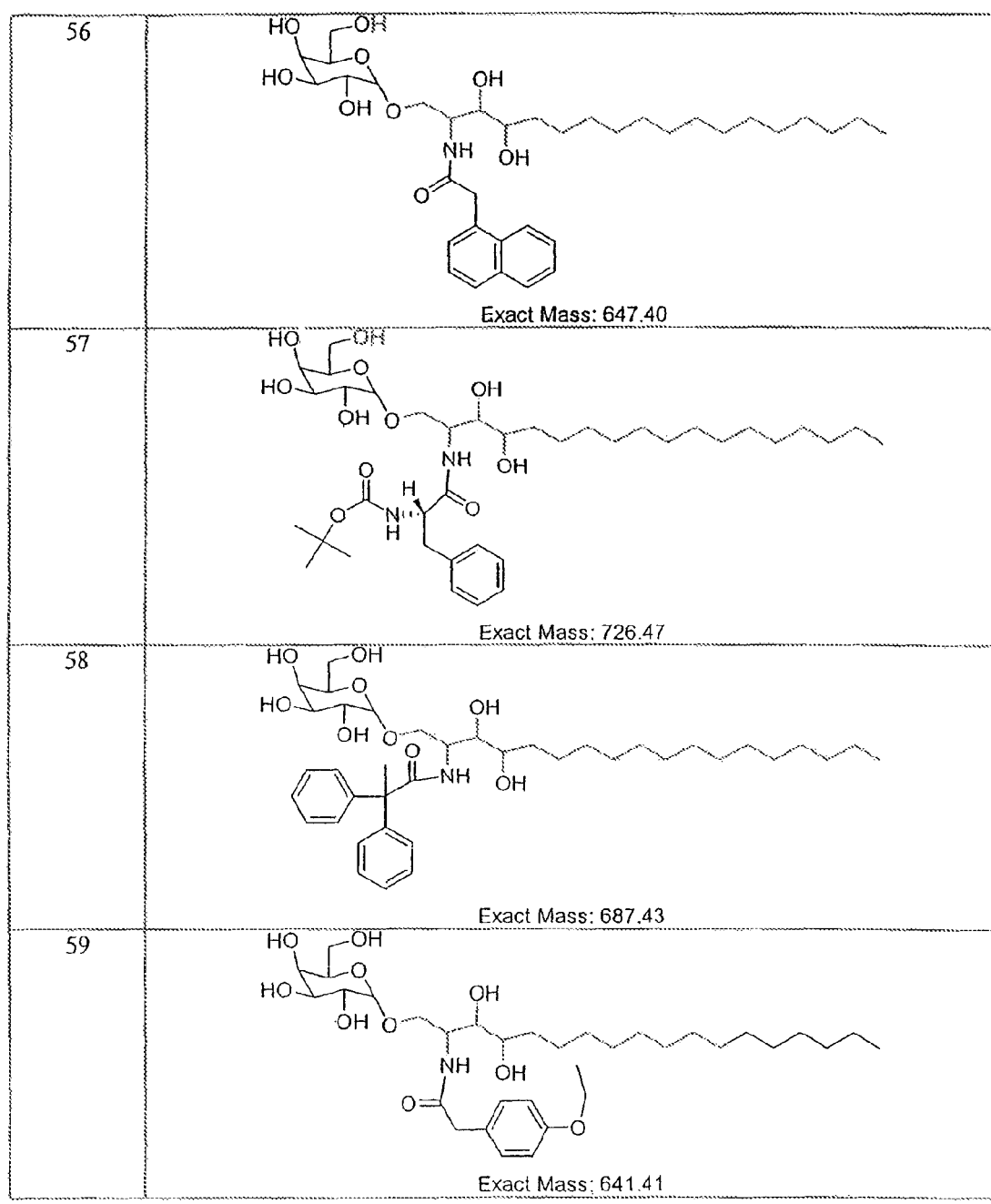

FIG. 5B15
YTC03 COMPOUNDS
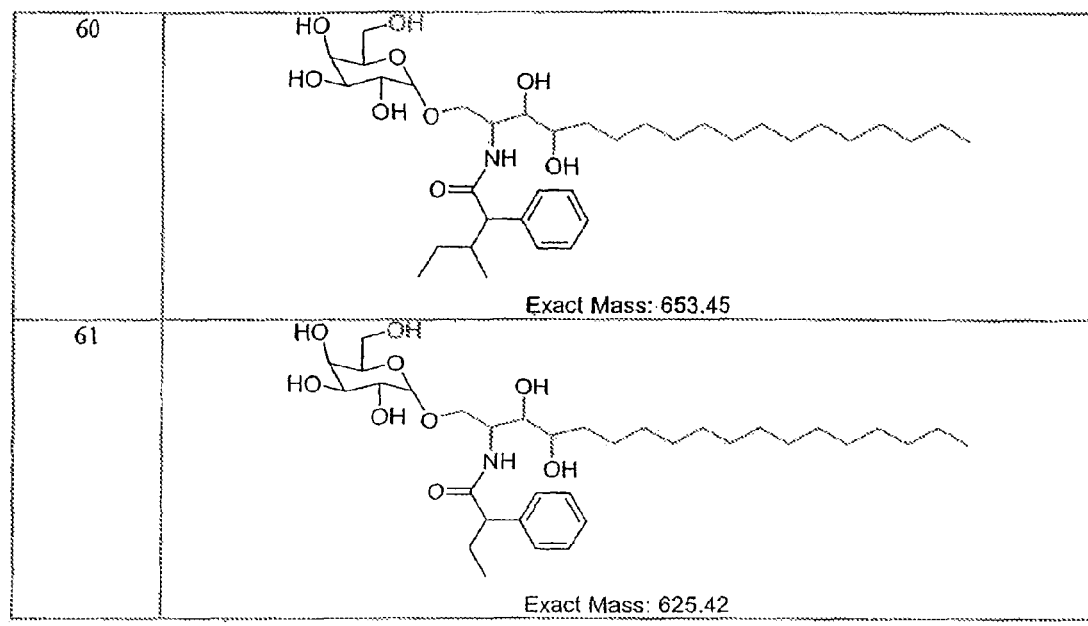

FIG. 5B16
DB03 Compounds
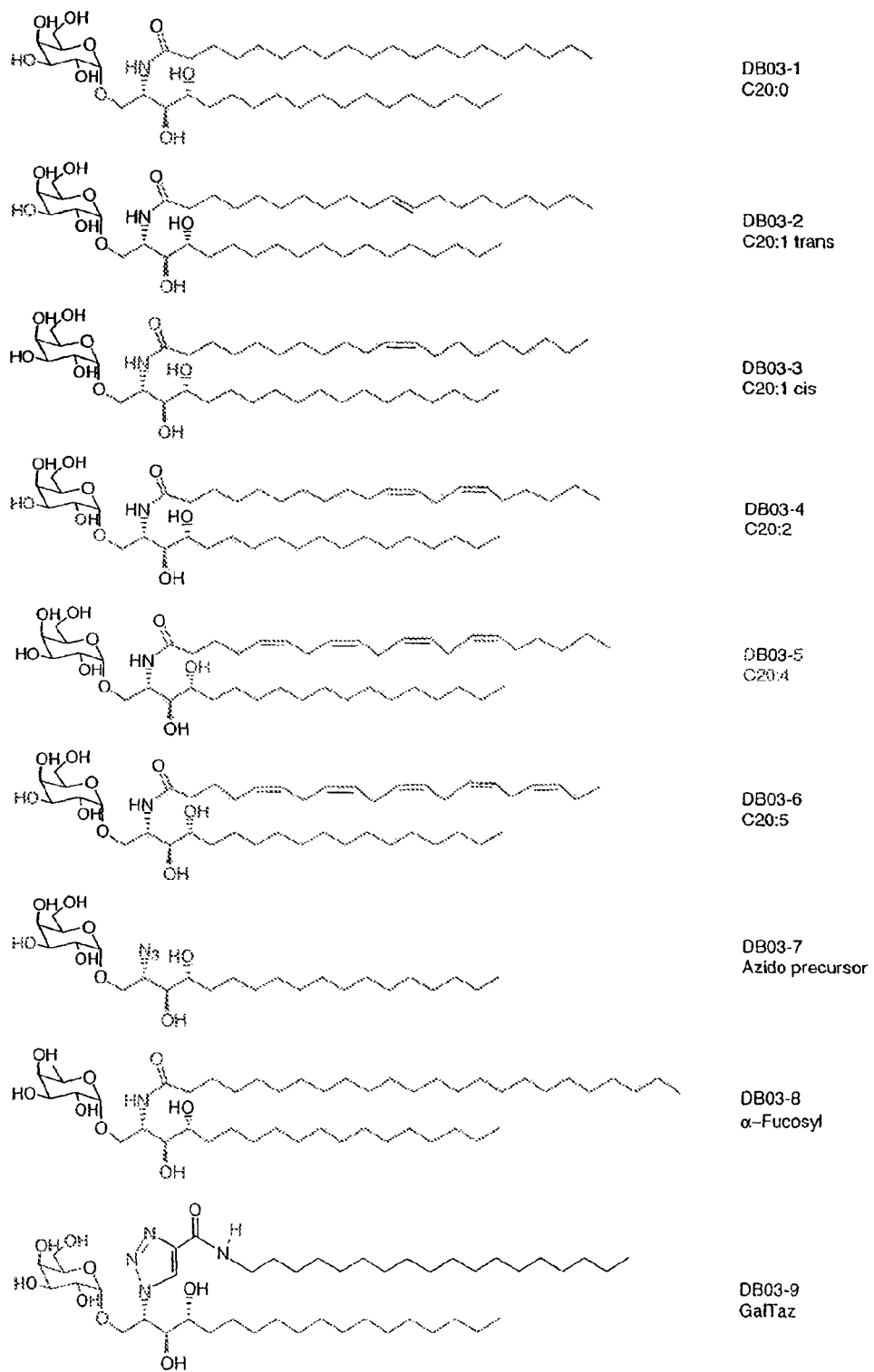
DB03-1
C20:0
DB03-2
C20:1 trans
DB03-3
C20:1 cis
DB03-4
C20:2
DB03-5
C20:4
DB03-6
C20:5
DB03-7
Azido precursor
DB03-8
α-Fucosyl
DB03-9
GalTaz

CERAMIDE DERIVATIVES AS MODULATORS OF IMMUNITY AND AUTOIMMUNITY

CROSS REFERENCE TO RELATED APPLICATIONS

This application is a continuation-in-part of application Ser. No. 11/211,653, filed Aug. 26, 2005 now U.S. Pat. No. 7,772,380, which claims the benefit of U.S. provisional application Ser. No. 60/605,362, filed Aug. 27, 2004, the contents of which are incorporated herein in their entirety.

GOVERNMENT RIGHTS

Portions of this work were supported by grants from the National Institutes of Health. The government may have certain rights in this invention.

FIELD OF THE INVENTION

The present invention generally relates to the activation of immune cells. More specifically, the invention relates to the identification of compounds that modulate NK T cells.

BACKGROUND

Description of the Related Art

References Cited

Bendelac, A. 1998. Mouse NK1$^+$ T cells. *Curr. Opin. Immunol.* 7:367.

Bendelac, A., O. Lantz, M. E. Quimby, J. W. Yewdell, J. R. Bennink, and R. R. Brutkiewicz. 1995. CD1 recognition by mouse NK1$^+$ T lymphocytes. *Science* 268:863.

Bendelac, A., M. N. Rivera, S. H. Park, and J. H. Roark. 1997. Mouse CD1-specific NK1 T cells: development, specificity, and function. *Annu. Rev. Immunol.* 15:535.

Benlagha, K., A. Weiss, A. Beavis, L. Teyton, and A. Bendelac. 2000. In vivo identification of glycolipid antigen-specific T cells using fluorescent CD1d tetramers. *J Exp. Med.* 191:1895-1903.

Burdin, N., L. Brossay, and M. Kronenberg. 1999. Immunization with alpha-galactosylceramide polarizes CD1-reactive NK T cells towards Th2 cytokine synthesis. *Eur. J Immunol.* 29:2014-2025.

Bynoe, M. S., L. Spatz, and B. Diamond. 1999. Characterization of anti-DNA B cells that escape negative selection. *Eur. J Immunol.* 29:1304.

Bynoe, M. S., C. M. Grimaldi, and B. Diamond. 2000. Estrogen up-regulates Bcl-2 and blocks tolerance induction of naive B cells. *Proc. Natl. Acad. Sci. U.S.A* 97:2703.

Crowe, N. Y., A. P. Uldrich, K. Kyparissoudis, K. J. Hammond, Y. Hayakawa, S. Sidobre, R. Keating, M. Kronenberg, M. J. Smyth, and D. I. Godfrey. 2003. Glycolipid antigen drives rapid expansion and sustained cytokine production by NK T cells. *J. Immunol.* 171:4020-4027.

Davodeau, F., M.-A. Peyrat, A. Necker, R. Dominici, F. Blanchard, C. Leget, J. Gaschet, P. Costa, Y. Jacques, A. Godard, H. Vié, A. Poggi, F. Romagné, and M. Bonneville. 1997. Close phenotypic and functional similarities between human and murine T cells expressing invariant TCR α-chains. *J Immunol.* 158:5603.

Eberl, G. and H. R. MacDonald. 1998. Rapid death and regeneration of NKT cells in anti-CD3eps. *Immunity.* 9:345.

Exley, M., J. Garcia, S. P. Balk, and S. Porcelli. 1997. Requirements for CD1d Recognition by Human Invariant Vα24$^+$ CD4$^-$CD8$^-$ T Cells. *J. Exp. Med.* 186:109.

Gaynor, B., C. Putterman, P. Valadon, L. Spatz, M. D. Scharff, and B. Diamond. 1997. Peptide inhibition of glomerular deposition of an anti-DNA antibody. *Proc. Natl. Acad. Sci. U.S.A* 94:1955.

Godfrey, D. I., K. J. Hammond, L. D. Poulton, M. J. Smyth, and A. G. Baxter. 2000. NKT cells: facts, functions and fallacies. *Immunol. Today* 21:573-583.

Hahn, B. H. 1998. Antibodies to DNA. *N. Engl. J. Med.* 338:1359.

Hammond, K. L., L. D. Poulton, L. J. Palmisano, P. A. Silveira, D. I. Godfrey, and A. G. Baxter. 1998. alpha/beta-T cell receptor (TCR)$^+$CD4$^-$CD8$^-$ (NKT) thymocytes prevent insulin-dependent diabetes mellitus in nonobese diabetic (NOD)/Lt mice by the influence of interleukin (IL)-4 and/or IL-10. *J. Exp. Med.* 187:1047.

Hong, S., M. T. Wilson, I. Serizawa, L. Wu, N. Singh, O. V. Naidenko, T. Miura, T. Haba, D. C. Scherer, J. Wei, M. Kronenberg, Y. Koezuka, and L. Van Kaer. 2001. The natural killer T-cell ligand alpha-galactosylceramide prevents autoimmune diabetes in non-obese diabetic mice. *Nat. Med.* 7:1052-1056.

Iijima, H., K. Kimura, T. Sakai, A. Uchimura, T. Shimizu, H. Ueno, T. Natori, and Y. Koezuka. 1998. Structure-activity relationship and conformational analysis of monoglycosylceramides on the syngeneic mixed leukocyte reaction. *Bioorg. Med. Chem.* 6:1905-1910.

Inoue, H., Y. Koezuka, N. Nishi, M. Osawa, K. Motoki, E. Kobayashi, K. Kabaya, M. Obuchi, H. Fukushima, and K. J. Mori. 1997. alpha-Galactosylceramide (AGL-517) treatment protects mice from lethal irradiation. *Exp. Hematol.* 25:935-944.

Joyce, S., A. S. Woods, J. W. Yewdell, J. R. Bennink, A. D. De Silva, A. Boesteanu, S. P. Balk, R. J. Cotter, and R. R. Brutkiewicz. 1998. Natural ligand of mouse CD1d1: cellular glycosylphosphatidylinositol. *Science* 279:1541.

Kotzin, B. L. 1996. Systemic lupus erythematosus. *Cell* 85:303.

Kawano, T., J. Cui, Y. Koezuka, I. Toura, Y. Kaneko, K. Motoki, H. Ueno, R. Nakagawa, H. Sato, E. Kondo, H. Koseki, and M. Taniguchi. 1997. CD1d-restricted and TCR-mediated activation of valpha14 NKT cells by glycosylceramides. *Science* 278:1626-1629.

Kobayashi, E., K. Motoki, T. Uchida, H. Fukushima, and Y. Koezuka. 1995. KRN7000, a novel immunomodulator, and its antitumor activities. *Oncol. Res.* 7:529-534.

Kobayashi, E., K. Motoki, Y. Yamaguchi, T. Uchida, H. Fukushima, and Y. Koezuka. 1996a. Enhancing effects of alpha-, beta-monoglycosylceramides on natural killer cell activity. *Bioorg. Med. Chem.* 4:615-619.

Kobayashi, E., K. Motoki, T. Natori, T. Uchida, H. Fukushima, and Y. Koezuka. 1996b. Enhancing effects of age-lasphin-11 on natural killer cell activities of normal and tumor-bearing mice. *Biol. Pharm. Bull.* 19:350-353.

Kojo, S., Y. Adachi, H. Keino, M. Taniguchi, and T. Sumida. 2001. Dysfunction of T cell receptor AV24AJ18$^+$, BV11$^+$ double-negative regulatory natural killer T cells in autoimmune diseases. *Arthritis Rheum.* 44:1127.

Koseki, H., H. Asano, T. Inaba, N. Miyashita, K. Moriwaki, K. F. Lindahl, Y. Mizutani, K. Imai, and M. Taniguchi. 1991. Dominant expression of a distinctive V14$^+$ T-cell antigen receptor chain in mice. *Proc. Natl. Acad. Sci. U.S.A.* 88:7518.

Kuo, P., M. S. Bynoe, C. Wang, and B. Diamond. 1999. Bcl-2 leads to expression of anti-DNA B cells but no nephritis: a model for a clinical subset. *Eur. J Immunol.* 29:3168.

Laloux, V., L. Beaudoin, D. Jeske, C. Carnaud, and A. Lehuen. 2001. NK T cell-induced protection against diabetes in Vα14-Jα281 transgenic nonobese diabetic mice is associated with a th2 shift circumscribed regionally to the islets and functionally to islet autoantigen. *J Immunol.* 166:3749.

Matsuda, J. L., O. V. Naidenko, L. Gapin, T. Nakayama, M. Taniguchi, C. R. Wang, Y. Koezuka, and M. Kronenberg. 2000. Tracking the response of natural killer T cells to a glycolipid antigen using CD1d tetramers. *J Exp. Med.* 192:741.

Mieza, M. A., T. Itoh, J. Q. Cui, Y. Makino, T. Kawano, K. Tsuchida, T. Koike, T. Shirai, H. Yagita, A. Matsuzawa, H. Koseki, and M. Taniguchi. 1996. Selective reduction of Vα14+ NK T cells associated with disease development in autoimmune-prone mice. *J Immunol.* 156:4035.

Miyamoto, K., S. Miyake, and T. Yamamura. 2001. A synthetic glycolipid prevents autoimmune encephalomyelitis by inducing TH2 bias of natural killer T cells. *Nature* 413:531-534.

Moody, D. B., G. S. Besra, I. A. Wilson, and S. A. Porcelli. 1999. The molecular basis of CD1-mediated presentation of lipid antigens. *Immunol. Rev* 172:285.

Morita, M., K. Motoki, K. Akimoto, T. Natori, T. Sakai, E. Sawa, K. Yamaji, Y. Koezuka, E. Kobayashi, and H. Fukushima. 1995. Structure-activity relationship of alpha-galactosylceramides against B16-bearing mice. *J. Med. Chem.* 38:2176-2187.

Motoki, K., M. Morita, E. Kobayashi, T. Uchida, H. Fukushima, and Y. Koezuka. 1996a. Effects of alpha-galactosylceramides on bone marrow cells in vitro and hematopoiesis in vivo. *Biol. Pharm. Bull.* 19:952-955.

Motoki, K., K. Maeda, H. Ueno, E. Kobayashi, T. Uchida, H. Fukushima, and Y. Koezuka. 1996b. Antitumor activities of combined treatment with a novel immunomodulator, (2S, 3S,4R)-1-O-(alpha-D-Galactopyranosyl)-2-(N-Hexacosanoylamino)-1,3,4-octadecanetriol (KRN7000), and radiotherapy in tumor-bearing mice. *Oncol. Res.* 8:155-162.

Motoki, K., M. Morita, E. Kobayashi, T. Uchida, K. Akimoto, H. Fukushima, and Y. Koezuka. 1995. Immunostimulatory and antitumor activities of monoglycosylceramides having various sugar moieties. *Biol. Pharm. Bull.* 18:1487-1491.

Naidenko, O. V., J. K. Maher, W. A. Ernst, T. Sakai, R. L. Modlin, and M. Kronenberg. 1999. Binding and antigen presentation of ceramide-containing glycolipids by soluble mouse and human CD1d molecules. *J Exp. Med.* 190:1069-1080.

Nakagawa, R., K. Motoki, H. Nakamura, H. Ueno, R. Iijima, A. Yamauchi, S. Tsuyuki, T. Inamoto, and Y. Koezuka. 1998. Antitumor activity of alpha-galactosylceramide, KRN7000, in mice with EL-4 hepatic metastasis and its cytokine production. *Oncol. Res.* 10:561-568.

Nakagawa, R., I. Serizawa, K. Motoki, M. Sato, H. Ueno, R. Iijima, H. Nakamura, A. Shimosaka, and Y. Koezuka. 2000. Antitumor activity of alpha-galactosylceramide, KRN7000, in mice with the melanoma B16 hepatic metastasis and immunohistological study of tumor infiltrating cells. *Oncol. Res.* 12:51-58.

Oishi, Y., T. Sumida, A. Sakamoto, Y. Kita, K. Kurasawa, Y. Nawata, K. Takabayashi, H. Takahashi, S. Yoshida, M. Taniguchi, Y. Saito, and I. Iwamoto. 2001. Selective reduction and recovery of invariant Vα24JαQ T cell receptor T cells in correlation with disease activity in patients with systemic lupus erythematosus. *J Rheumatol.* 28:275.

Pisetsky, D. S., G. Gilkeson, and E. W. St Clair. 1997. Systemic lupus erythematosus. Diagnosis and treatment. *Med. Clin. North Am.* 81:113.

Porcelli, S. A. 1995. The CD1 family: a third lineage of antigen-presenting molecules. *Adv. Immunol.* 59:1.

Porcelli, S. A. and R. L. Modlin. 1999. The CD1 system: antigen-presenting molecules for T cell recognition of lipids and glycolipids. *Ann. Rev. Immunol.* 17:297.

Porcelti, S., C. E. Yockey, M. B. Brenner, and S. P. Balk. 1993. Analysis of T cell antigen receptor (TCR) expression by human peripheral blood CD4−8−αβ T cells demonstrates preferential use of several Vβ genes and an invariant TCR α chain. *J. Exp. Med.* 178:1.

Porcelli, S. A., B. W. Segelke, M. Sugita, I. A. Wilson, and M. B. Brenner. 1998. The CD1 family of lipid antigen presenting molecules. *Immunol. Today* 19:362.

Putterman, C. and B. Diamond. 1998. Immunization with a peptide surrogate for double-stranded DNA (dsDNA) induces autoantibody production and renal immunoglobulin deposition. *J Exp. Med.* 188:29.

Putterman, C., B. Deocharan, and B. Diamond. 2000. Molecular analysis of the autoantibody response in peptide-induced autoimmunity. *J Immunol.* 164:2542.

Sharif, S., G. A. Arreaza, P. Zucker, Q. S. Mi, J. Sondhi, O. V. Naidenko, M. Kronenberg, Y. Koezuka, T. L. Delovitch, J. M. Gombert, M. Leite-De-Moraes, C. Gouarin, R. Zhu, A. Hameg, T. Nakayama, M. Taniguchi, F. Lepault, A. Lehuen, J. F. Bach, and A. Herbelin. 2001. Activation of natural killer T cells by alpha-galactosylceramide treatment prevents the onset and recurrence of autoimmune Type 1 diabetes. *Nat. Med.* 7:1057-1062.

Sharif, S., G. A. Arreaza, P. Zucker, Q. S. Mi, and T. L. Delovitch. 2002. Regulation of autoimmune disease by natural killer T cells. *J. Mol. Med.* 80:290-300.

Sidobre, S., O. V. Naidenko, B. C. Sim, N. R. Gascoigne, K. C. Garcia, and M. Kronenberg. 2002. The V alpha 14 NKT cell TCR exhibits high-affinity binding to a glycolipid/CD1d complex. *J. Immunol.* 169:1340-1348.

Sieling, P. A., S. A. Porcelli, B. T. Duong, F. Spada, B. R. Bloom, B. Diamond, and B. H. Hahn. 2000. Human double-negative T cells in systemic lupus erythematosus provide help for IgG and are restricted by CD1c. *J Immunol.* 165:5338.

Smyth, M. J. and D. I. Godfrey. 2000. NKT cells and tumor immunity—a double-edged sword. *Nat. Immunol.* 1:459-460.

Spada, F., Y. Koezuka, and S. A. Porcelli. 1998. CD1d-restricted recognition of synthetic glycolipid antigens by human natural killer T cells. *J. Exp. Med.* 188:1.

Spatz, L., V. Saenko, A. Iliev, L. Jones, L. Geskin, and B. Diamond. 1997. Light chain usage in anti-double-stranded DNA B cell subsets: role in cell fate determination. *J Exp. Med.* 185:1317.

Sumida, T., A. Sakamoto, H. Murata, Y. Makino, H. Takahashi, S. Yoshida, K. Nishioka, I. Iwamoto, and M. Taniguchi. 1995. Selective reduction of T cells bearing invariant Vα24JαQ antigen receptor in patients with systemic sclerosis. *J. Exp. Med.* 182:1163.

Takeda, K. and G. Dennert. 1993. The development of autoimmunity in C57BL/6 lpr mice correlates with the disappearance of natural killer type 1-positive cells: evidence for their suppressive action on bone marrow stem cell proliferation, B cell immunoglobulin secretion, and autoimmune symptoms. *J Exp. Med.* 177:155.

Uchimura, A., T. Shimizu, M. Morita, H. Ueno, K. Motoki, H. Fukushima, T. Natori, and Y. Koezuka. 1997a. Immunostimulatory activities of monoglycosylated alpha-D-pyranosylceramides. *Bioorg. Med. Chem.* 5:2245-2249.

Uchimura, A., T. Shimizu, M. Nakajima, H. Ueno, K. Motoki, H. Fukushima, T. Natori, and Y. Koezuka. 1997b. Immunostimulatory activities of mono- or diglycosylated alpha-galactosylceramides. *Bioorg. Med. Chem.* 5:1447-1452.

Wang, B., Y. B. Geng, and C. R. Wang. 2001. CD1-restricted NK T cells protect nonobese diabetic mice from developing diabetes. *J. Exp. Med.* 194:313-320.

Wilson, S. B., S. C. Kent, K. T. Patton, T. Orban, R. A. Jackson, M. Exley, S. Porcelli, D. A. Schatz, M. A. Atkinson, S. P. Balk, J. L. Strominger, and D. A. Hafler. 1998. Extreme Th1 bias of invariant Vα24JαQ T cells in type 1 diabetes. *Nature* 391:177.

Yamaguchi, Y., K. Motoki, H. Ueno, K. Maeda, E. Kobayashi, H. Inoue, H. Fukushima, and Y. Koezuka. 1996. Enhancing effects of (2S,3S,4R)-1-O-(alpha-D-galactopyranosyl)-2-(N-hexacosanoylamino)-1,3,4-octadecanetriol (KRN7000) on antigen-presenting function of antigen-presenting cells and antimetastatic activity of KRN7000-pretreated antigen-presenting cells. *Oncol. Res.* 8:399-407.

Yoshimoto, T. and W. E. Paul. 1994. $CD4^{pos}$ NK1.1$^{pos}$ T cells promptly produced IL-4 in response to in vivo challenge with anti-CD3. *J. Exp. Med.* 179:1285.

Yoshimoto, T., A. Bendelac, C. Watson, J. Hu-Li, and W. E. Paul. 1995a. Role of NK1.1 T cells in a TH2 response and in immunoglobulin E production. *Science* 270:1845.

Yoshimoto, T., A. Bendelac, J. Hu-Li, and W. E. Paul. 1995b. Defective IgE production by SJL mice is linked to the absence of CD4+, NK1.1+ T cells that promptly produce interleukin 4. *Proc. Natl. Acad. Sci. U.S.A.* 92:11931.

Zeng, Z., A. R. Castano, B. W. Segelke, E. A. Stura, P. A. Peterson, and I. A. Wilson. 1997. Crystal structure of mouse CD1: An MHC-like fold with a large hydrophobic binding groove. *Science* 277:339.

Zeng, D., M. K. Lee, J. Tung, A. Brendolan, and S. Strober. 2000. Cutting edge: a role for CD1 in the pathogenesis of lupus in NZB/NZW mice. *J Immunol.* 164:5000.

PCT Patent Publication WO93/05055.
U.S. Pat. No. 5,679,347.
U.S. Pat. No. 5,780,441.
U.S. Pat. No. 5,853,737.
U.S. Pat. No. 5,936,076.
U.S. Pat. No. 6,162,609.
U.S. Pat. No. 6,238,676.

NK T Cells.

A novel lineage of T lymphocytes referred to as "natural killer T cells" (NK T cells) has recently been identified and demonstrated to be distinct from conventional αβ T cells in a number of important ways (Bendelac et al., 1997; Bendelac 1998). NK T cells were first identified in mice (Bendelac et al., 1997), but recent work has shown that they are remarkably conserved in terms of phenotype and function in humans (Exley et al., 1997; Spada et al., 1998; Davodeau et al., 1997). These T cells were first recognized as a distinct population because of their coexpression of the NK lineage marker NK1.1 (NKR-P1C) and the αβ T cell receptor. They have been found to be either $CD4^+$ or $CD4^+$ ("double negative" or DN), and are now recognized to have a number of unique phenotypic traits, including low or intermediate T cell receptor (TCR) levels ($TCR^{int}$), and expression of a variety of C-type lectin receptors encoded by the so-called NK locus (e.g., NK1.1, CD69, CD94, and various Ly-49 family members). In addition, even in their normal baseline state, they express markers indicative of an activated phenotype ($CD44^{hi}$, $CD62L^{lo}$ L-2R$β^{hi}$). NK T cells originate from both thymic and extrathymic developmental pathways, and their normal turnover appears to be compensated by a long-lived population that resides in the bone marrow (Eberl et al., 1998). They accumulate to high levels in normal liver where they comprise as much as 30% of the resident hepatic T cells, and also make up a substantial fraction of the T cells of spleen and bone marrow, and are found in lower but detectable numbers in other lymphoid tissues.

A key property of many NK T cells is their expression of TCRs with extremely limited diversity. The TCRα chains of the great majority of murine NK1.1$^+$ T cells in normal animals are absolutely identical, and are formed by precise rearrangement of the germline Vα14 and Jα281 gene segments without junctional diversity (Koseki et al., 1991; Lantz et al., 1994). This invariant TCRα chain is typically paired with a semi-invariant TCRβ chain, which shows Vβ gene usage that is highly skewed toward just a few germline Vβ genes (most commonly Vβ family members in mice, with Vβ2 and Vβ7 also prominently represented). This TCR structure is also seen in human NK T cells which express a homologous invariant TCRα chain (Vα24-JαQ) and restricted Vβ gene usage (most commonly Vβ11), thus implying that NK T cells must recognize a conserved nonpolymorphic ligand (Porcelli et al., 1993; Exley et al., 1997; Lantz et al., 1994).

It is now well established that the great majority of NK T cells expressing the invariant TCRα chain are selected by recognition of the CD1d molecule, a nonpolymorphic MHC class I-like cell surface glycoprotein that is conserved between humans, mice and possibly all mammals (Bendelac et al., 1995; Exley et al., 1997; see also U.S. Pat. Nos. 5,679, 347; 5,853,737; and 6,238,676). In humans, the CD1 family consists of five nonpolymorphic genes that map to chromosome 1. These encode five distinct but closely related cell surface glycoproteins (designated as CD1a, CD1b, CD1c, CD1d, and CD1e) that bear striking structural similarities to MHC class I antigen-presenting molecules (Zeng et al., 1997; Porcelli, 1995). A substantial body of data has revealed that several of the human CD1 proteins, (CD1a, CD1b and CD1c—collectively referred to as group 1 CD1) function as antigen presenting molecules for a subset of T cells that responds to specific lipids and glycolipids found in the cell walls of mycobacteria and other bacterial pathogens (Porcelli et al., 1998; Porcelli et al., 1999). The ability of CD1 proteins to perform this role is most likely due to their ability to act as lipid binding proteins, which trap hydrophobic alkyl chains within a deep hydrophobic pocket formed by the two membrane distal domains of the protein (Moody et al., 1999). This leads to the antigenic lipid being displayed such that its hydrophilic or polar head group is accessible for direct interactions with the TCRs of specific CD1 restricted T cells (FIG. 1).

The discovery of the lipid antigen presenting function of human group 1 CD1 molecules suggested that a similar function might also exist for the CD1d protein, the only member of this family that is conserved in rodents. This possibility is supported by the finding that CD1d molecules isolated from cultured cells are associated noncovalently with glycosyl phosphatidylinositols, which could represent a self glycolipid ligand bound in the CD1d hydrophobic pocket (Joyce et al., 1998). Perhaps even more striking was the finding that a family of ceramide-like glycolipids (i.e., α-galactosylceramide (αGalCer) and related α-glycosyl ceramides), could stimulate strong CD1d-restricted responses by murine NK T cells (Kawano et al., 1997). These compounds contain an α-anomeric hexose sugar (galactose or glucose being active for NK T cell recognition), distinguishing them from the ceramides that commonly occur in mammalian tissues which contain only β-anomeric sugars. Remarkably, these compounds are at present known to occur naturally only in marine sponges, the source from which they were originally isolated, and became of interest to immunologists when it was demonstrated that αGalCer induced dramatic tumor rejection as a result of immune activation when injected into tumor bearing mice (Kobayashi et al., 1995). Subsequently, this activity was linked to the ability of αGalCer to rapidly activate NK T cells through a CD1d dependent mechanism. It has now been definitively shown that αGalCer binds to CD1d, thus creating a molecular complex that has a measurable affinity for the TCRs of NK T cells (Naidenko et al., 1999; Matsuda et al., 2000; Benlagha et al., 2000). Thus, αGalCer provides a potent agent that can enable activation of the majority of NK T cells both in vitro and in vivo.

The most extensively studied NK T activating αGalCer, called KRN7000 in the literature, is a synthetic molecule that has a structure similar to natural forms of αGalCer that were originally isolated from a marine sponge on the basis of their anti-cancer activity in rodents (Kawano et al., 1997; Kobayashi et al., 1995; Iijima et al., 1998; Inoue et al., 1997; Kobayashi et al., 1996a, 1996b; Hakagawa et al., 2000; Uchimura et al., 1997a; Uchimura et al., 1997b; Motoki et al., 1996a; Motoki et al., 1995; Nakagawa et al., 1998; Yamaguchi et al., 1996; Morita et al., 1995; Motoki et al., 1996b). The structure of KRN7000 is shown in FIG. 1.

Given the potent activity of KRN7000 and the promising therapeutic effects on cancer, infectious and autoimmune diseases in animals, the possibility of developing structural analogues with greater potency or different activities is an area of obvious interest. In this regard, one previous report has described a synthetic analogue of KRN7000 with a truncated sphingosine base that showed an enhanced ability to suppress autoimmunity in a mouse model of experimental allergic encephalomyelitis (EAE) (Miyamoyo et al., 2001). The structure of this compound, which was designated "OCH" by the investigators who reported it, is shown in FIG. 3. Other variants altered in the αGalCer sphingosine base are identified in U.S. Pat. No. 5,936,076. In contrast, there has been very little previous work on modifications of the fatty acid chain. Fatty acid chain length variations were studied by Kawano, et al. (1997), but this analysis was very limited and not revealing of any interesting properties.

A large body of literature dating from November 1997 to the present time has studied the mechanism by which KRN7000 activates the immune system of mammals (Kawano et al., 1997; Benlagha et al., 2000; Burdin et al., 1999; Crowe et al., 2003; Naidenko et al., 1999; Sidobre et al., 2002; Godfrey et al., 2000; Smyth and Godfrey, 2000). These studies uniformly show that the proximal mechanism for the effect of KRN7000 is the binding of this compound to a CD1d protein, which is expressed on most hematopoietic cells, as well as some epithelial and other cell lineages. The binding of KRN7000 to CD1d creates a molecular complex that is recognized with high affinity by the T cell antigen receptors (TCRs) of a subset of T lymphocytes called natural killer T cells (NK T cells). Recognition of the KRN7000/CD1d complex leads to rapid activation of the NK T cells, which reside in the liver, spleen and other lymphoid organs and have the potential to traffic to potentially any tissue. Activated NK T cells rapidly secrete a wide range of chemokines and other cytokines, and also have the capability of activating other cell types such as dendritic cells and natural killer (NK) cells. The chain of events that follows the activation of NK T cells by KRN700/CD1d complexes has been shown to have many potential downstream effects on the immune system. For example, in the setting of certain types of infections this can lead to an adjuvant effect that boosts the adaptive immunity to the infection and promotes healing. Or, in the setting of certain types of autoimmune diseases, the activation of NK T cells by KRN7000 can alter the course of the autoimmune response in a way that suppresses tissue destruction and ameliorates the disease. This latter effect has been documented to be especially strong in a mouse model of spontaneous type 1 diabetes mellitus (i.e., the NOD mouse strain, FIG. 2) (Sharif et al., 2001; Sharif et al., 2002; Hong et al., 2001; Wang et al., 2001).

The functions of NK T lymphocytes remain incompletely resolved, but a variety of studies point to an important role for these T cells in the regulation of immune responses. A hallmark of NK T cells is their rapid production of large quantities of both IL-4 and IFN-γ upon stimulation through their αβ TCRs (Exley et al., 1997; Yoshimoto et al., 1994; Yoshimoto et al., 1995a; Yoshimoto et al. 1995b). In fact, their identification as perhaps the major cell responsible for the early production of IL-4 during immune activation suggested that they may play a critical role in polarizing type 2 (Th2) T cell responses. In this regard, it is not surprising that NK T cells have been identified to play a significant role in determining the outcome of infections with a variety of different pathogens in mice. In addition, a major immunoregulatory role for NK T cells has been proposed in autoimmune Type 1 diabetes mellitus, both in humans and in the NOD mouse model. In human subjects, it has been established that the progression to overt diabetes mellitus in predisposed subjects is associated with a decline in the number of circulating NK T cells, and with a loss of the ability of these cells to produce IL-4 while they retain production of IFNγ (Wilson et al., 1998). These findings are strongly supported by virtually identical observations in NOD mice. Most importantly, a number of studies show that the onset of diabetes mellitus in the NOD model can be delayed or even prevented by increasing the numbers of available IL-4 producing NK T cells through adoptive transfer or by expression of a Vα14-Jα281 TCRα transgene (Hammond et al., 1998; Laloux et al., 2001). Recently, it has been shown that treatment of NOD mice with αGalCer (KRN7000) in vivo can alter, delay, or even prevent the onset of overt diabetes mellitus (Hong et al., 2001; Sharif et al., 2001), providing a strong precedent for the development of this compound and related analogues as pharmacologic agents for the modulation of autoimmune disorders.

Autoimmune Diseases.

Autoimmune diseases are the result of a patient's immune system attacking their own cells and tissues. This can result in a wide variety of diseases, including multiple sclerosis, myasthenia gravis, Addison's disease, alopecia areata, ankylosing spondylitis, antiphospholipid syndrome, Behcet's disease, Crohn's disease and ulcerative colitis, Goodpasture syndrome, pemphigus vulgaris, primary biliary cirrhosis, rheumatic fever, sarcoidosis, vasculitis, vitiligo, Wegener's granulomatosis, graft vs. host disease, Meniere's disease, rheumatoid arthritis, diabetes mellitus, systemic lupus erythematosus (SLE), psoriasis, scleroderma, idiopathic thrombocytopenia purpura, pancreatitis, inflammatory bowel disease, glomerulo-nephritis, encephalomyelitis, and Sjogen's disease. For the most part, the etiology of autoimmune diseases is poorly understood, and, although there are several treatments for autoimmune disease such as systemic lupus erythematosus, all possess serious disadvantages. Thus, there is a need for safer and more effective treatments for autoimmune diseases.

Systemic lupus erythematosus (SLE) is a common autoimmune disease that damages multiple vital organs and causes substantial morbidity and mortality even when the best available current treatments are applied (Kotzin, 1996; Pisetsky et al., 1997).

Most current models for the pathogenesis of SLE focus on the autoreactivity of B lymphocytes, and their production of a variety of autoantibodies. Epidemiologic studies and considerable data from animal models support the view that certain autoantibodies associated with SLE in humans, such as antibodies to double stranded DNA (dsDNA) and specific nucleic acid/protein complexes, play a direct role in disease pathogenesis (Hahn, 1998). Thus, a key goal for research into the causes and effective therapy of SLE is to identify mechanisms that maintain tolerance within the B cell compartment, and that regulate B cell autoreactivity. Such mechanisms may provide the most effective targets for the development of improved treatment and prevention of SLE.

In recent years, mouse models of SLE have contributed greatly to our understanding of the basic mechanisms that lead to this disorder (Datta, 1988; Silveira and Baxter, 2001). One hereditary murine model of SLE which is generally accepted to strongly parallel many aspects of the human illness is that which occurs in the F1 cross between New Zealand Black female and New Zealand White male mice (NZB/W F1 mice). These mice develop signs of B cell autoreactivity at an early age with secretion of IgM and double-stranded DNA (dsDNA) antibodies. At approximately six months of age, NZB/W F1 mice show a transition of autoantibody secretion from IgM to IgG, and this is associated with the production of cationic IgG anti-dsDNA antibodies that are pathogenic and contribute to immune complex glomerulonephritis (Zeng et al., 2000). In similar fashion, mice bearing the lpr mutation exhibit an age dependent development of spontaneous SLE-like disease, which is again associated with the occurrence of high titers of IgG antibodies against dsDNA and other target antigens that are characteristic of SLE in humans. These spontaneous models of SLE provide excellent model systems in which to examine various mechanisms of immune regulation and tolerance to determine what role they may play in preventing the development of B cell autoreactivity and SLE.

In addition to these hereditary models of spontaneous SLE in mice, various models have been devised to study the processes that may lead to induction of SLE on a genetic background that is not predisposed to autoimmunity. These models have been useful in helping to determine the mechanisms that may lead to the disruption of normal immune tolerance to allow autoreactive lymphocytes to persist and become activated. Although such models do not in general provide an accurate simulation of the actual disease, they allow one to examine events occurring shortly after the induction of autoreactivity. Two models of inducible B cell autoreactivity that leads to autoantibody production similar to that which is characteristic of SLE are the R4A heavy chain transgenic mouse model and the MAP-peptide induced autoimmunity mouse model.

The R4A transgenic mouse model of B cell autoreactivity has been the subject of many highly informative studies on the mechanisms of B cell tolerance (Bynoe et al., 2000; Kuo et al., 1999; Bynoe et al., 1999). These mice express a transgene that encodes a rearranged IgG2b heavy chain of a monoclonal anti-dsDNA antibody called R4A. The original R4A antibody has a moderate affinity for dsDNA, and is classified as a pathogenic antibody in BALB/c mice because of its tendency to form deposits in renal glomeruli. R4A has also been shown to bind with high affinity to a protein antigen expressed on mesangial cells, which has recently been identified to be α-actinin. In the R4A transgenic (R4A Tg) mice, the rearranged IgG2b heavy chain associates with numerous endogenous light chains to generate antibodies with varying affinities for dsDNA, as well as a presumably large array of nonautoimmune specificities.

Serum autoantibody titers are negligible in R4A Tg mice, but the mice harbor at least three separate populations of anti-dsDNA B cells (Spatz et al., 1997). The normally deleted high affinity anti-dsDNA B cells of R4A Tg mice can also be rescued by treatment of these mice with estradiol (Bynoe et al., 2000). This transgenic model provides a sensitive environment in which to study the factors that regulate the selection and survival of B cells that have a strong intrinsic skewing toward recognition of anti-dsDNA.

In the MAP-peptide induced model, nonautoimmune BALB/c mice can be induced to develop lupus-like autoimmunity following immunization with a multimerized form of a synthetic peptide (DWEYSVWLSN) (Gaynor et al., 1997; Putterman et al., 1998; Putterman et al., 2000). The antigenic peptide contains a core sequence (DWEYS) that functions as a mimetope of dsDNA. To enhance the immunogenicity of the peptide mimetope, DWEYSVWLSN is conjugated to an eight branched polylysine backbone, and emulsified in Complete Freund's adjuvant. Mice immunized with this multiple antigenic peptide (MAP) conjugate develop anti-dsDNA antibodies of both IgM and IgG isotypes, and also develop antibodies against a variety of other autoantigens characteristic of SLE and IgM and IgG deposits in the renal glomeruli. Anti-dsDNA antibodies isolated from MAP-peptide immunized BALB/c mice show some striking similarities to autoantibodies isolated from spontaneous hereditary murine SLE models, such as the NZB/W F1. This model provides the opportunity to assess the control of autoimmunity that develops in normal animals following the controlled application of a defined immunizing stimulus that has the ability to break tolerance.

A number of studies strongly suggest that defects in NK T cells similar to those associated with the development of autoimmune diabetes mellitus are also present in SLE. For example, Takeda and Dennert initially reported that the development of autoimmunity in C57BL/6 lpr/lpr mice correlated with the disappearance of NK1.1$^+$ cells, and showed that deletion of these cells in vivo accelerated disease while adoptive transfer of NK1.1$^+$ cells delayed the onset of disease (Takeda et al., 1993). This study did not distinguish between NK cells and NK T cells in the in vivo analysis, but demonstrated in vitro that a CD3$^+$ NK1.1$^+$ population mediated direct inhibition of anti-DNA autoantibody production. Subsequently, Mieza et al. have shown the occurrence of marked reductions and eventual disappearance of NK T cells expressing the invariant Vα14-Jα281 rearrangement concurrently with the development of disease in a variety of lupus-prone mice, including MRL lpr/lpr, C3H gld/gld and NZB/W F1 mice (Mieza et al., 1996). These investigators also showed that Vα14 transgenic MRL lpr/lpr mice, in which the levels of Vα14 NK T cells are upregulated, showed a significant suppression of their lymphoproliferative disease, confirming that Vα14 NK T cells may play a significant regulatory role in disease onset and progression in this animal model of SLE.

Importantly, recent findings in humans with SLE have demonstrated changes in CD1-reactive T cells, including some that closely parallel the defects in NK T cells found in the mouse SLE models. For example, Sieling et al. reported that human subjects with SLE have increased numbers of CD1-restricted CD4$^-$8$^-$ T cells in their circulating lymphocyte pool, and that these unusual T cells can potently trigger B cells to produce antibody and undergo isotype switching (Sieling et al., 2000). These T cells were found to recognize the human CD1c protein, which along with CD1d is one of two human CD1 isoforms known to be strongly expressed by B cells. Even more striking are the results reported by Oishi et al., who showed that NK T cells expressing the invariant TCRα chain were essentially absent from the circulation in human subjects with active SLE. Following corticosteroid induced remissions, NK T cells could again be detected, establishing an intriguing inverse correlation between the presence of these regulatory T cells and the level of disease activity (Oishi et al., 2001). Another recent study has confirmed many of these findings in human SLE (Kojo et al., 2001), and very similar findings were reported by Sumida et al. in a study of patients with systemic sclerosis, a systemic autoimmune disease that shares several features with SLE including prominent autoantibody production against nuclear antigens (Sumida et al., 1995). These results indicate a strong correlation between the abnormalities reported in murine models and true SLE and other related autoimmune diseases in humans. See also U.S. Pat. No. 6,162,609, disclosing a method of treating autoimmune disease by increasing numbers of CD4− CD8− NK T cells. The disclosed method for increasing these cells is by exposing them to CD1d or fragments thereof.

Other autoimmune diseases appear similar to SLE in that they have an etiology that is mediated at least in part by autoantibodies. Included here are myasthenia gravis, pemphigus vulgaris, Guillain-Barre syndrome, antiphospholipid antibody syndrome, Goodpasture syndrome, graft vs. host disease, multiple sclerosis, primary biliary cirrhosis, scleroderma, vasculitis, vitiligo, Wegener's granulomatosis, rheumatoid arthritis, glomerulo-nephritis, idiopathic thrombocytopenia purpura, and Sjogen's disease.

Vaccines

Vaccines have been developed, and are under development, for both T-independent antigens and T-dependent antigens. Since the T-independent immune response generally does not have the memory component that is necessary to produce an effective vaccine, vaccines against T-independent antigens are often developed by taking a component of the pathogen that normally induces the T-independent response, such as a characteristic polysaccharide, and conjugating that component to a carrier molecule that is capable of inducing a T-dependent response. Thus, the component becomes part of a T-dependent antigen, hopefully causing a T-dependent immune reaction (and memory B cell production) against the component of the T-independent pathogen. However, these vaccines, as well as many vaccines against T-dependent antigens, are often not able to induce a sufficient T-dependent immune response to effectively allow the vaccinated mammal to be able to fight off subsequent challenge by the pathogen. KRN7000 has been shown to be an effective adjuvant for vaccines due to its ability to activate T cells and improve T-dependent responses (PCT Patent Publication WO93/05055).

Passive Immunity

An increasingly important mode of cancer therapy is administration of human antibodies against specific tumor target molecules such as CD20 in Non-Hodgkins Lymphoma (NHL) or Her2/neu in a subset of patients with breast cancer. It has been demonstrated that efficacy of anti-CD20 antibodies for treatment of NHL is, in part, mediated by antibody dependent cellular cytotoxicity (ADCC) which is a major function of natural killer (NK) cells. A potentially important strategy for enhancing efficacy of such passively transferred antibody therapeutics directed at tumor antigens would be to enhance NK activity by co-administration of an adjuvant that promotes the activation and expansion of NK cells. Because of the key role that NK T cells play in the activation of IFNγ producing NK cells, molecules described herein that further enhance the NK stimulating activity of NK T cells are likely to be valuable adjuvants for antibody therapeutics.

Due to the importance of NK T cells in mammalian immunity, there is a need for the identification and characterization of additional modulators of NK T cells. The present invention addresses that need.

SUMMARY OF THE INVENTION

Accordingly, the inventors have discovered that many variants of αGalCer are capable of activating NK T cells, that these variants differ in the type of cell that efficiently presents the compound, and that these variants induce varied cytokine profiles when used to activate NK T cells.

Thus, in some embodiments, the invention is directed to α-galactosylceramides comprising Formula I:

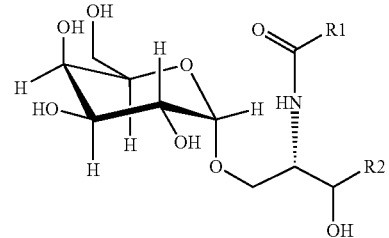

Formula I wherein
R1 is a linear or branched $C_1$-$C_{27}$ alkene with at least one C=C bond but not —$(CH_2)_7CH$=$CH(CH_2)_7CH_3$, or R1 is C(OH)—R3 wherein R3 is a linear or branched $C_1$-$C_{26}$ alkene with at least one C=C bond; and
R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH$=$CH(CH_2)_xCH_3$,
(e) —$CH(OH)(CH_2)_xCH(CH_3)CH_2CH_3$,
wherein X is an integer ranging from 5-17.

In other embodiments, the invention is directed to α-galactosylceramides comprising Formula I:

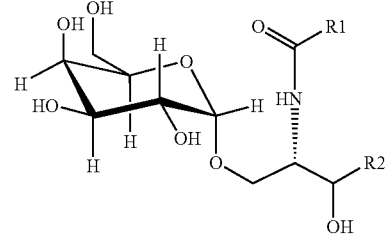

Formula I wherein
R1 is branched $C_1$-$C_{27}$ alkane or
R1 is C(OH)—R3 where R3 is a linear or branched $C_1$-$C_{26}$ alkene; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$,
wherein X is an integer ranging from 5-17.

In additional embodiments, the invention is directed to α-galactosylceramides comprising Formula I:

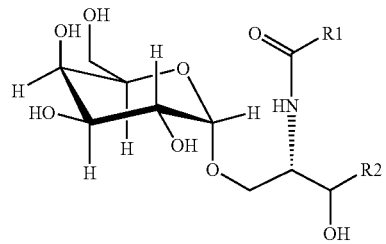

Formula I wherein
R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$,
wherein X is an integer ranging from 5-17.

The invention is additionally directed to α-galactosylceramides comprising Formula I:

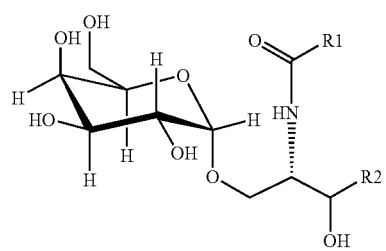

Formula I wherein
R1 is selected from the group consisting of —C(=O)OCH$_2$CH$_3$, —(CH$_2$)$_6$CH$_3$, —(CH$_2$)$_4$Cl, —(CH$_2$)$_{16}$CH$_3$, —(CH$_2$)$_5$CH$_3$, —(CH$_2$)$_2$CH$_3$, —(CH$_2$)$_4$CH$_3$, —(CH$_2$)$_8$CH$_3$, —(CH$_2$)$_{10}$CH$_3$, —(CH$_2$)$_{12}$CH$_3$; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_x(CH_3$,
(e) —$CH(OH)(CH_2)_xCH(CH_3)CH_2CH_3$,
wherein X is an integer ranging from 5-17.

In further embodiments, the invention is directed to glycosylceramides comprising Formula II:

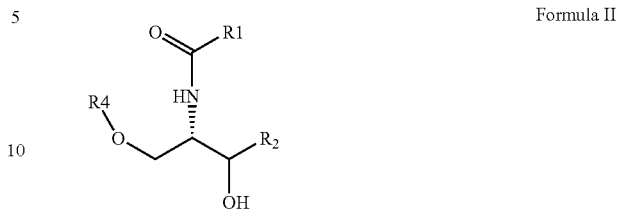

Formula II wherein
R1 is a linear or branched $C_1$-$C_{27}$ alkane or alkene, or
R1 is C(OH)—R3 wherein R3 is a linear or branched $C_1$-$C_{26}$ alkene with at least one C=C bond,
or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):
(a) —$CH_2(CH_1)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$,
wherein X is an integer ranging from 5-17; and
R4 is an α-linked monosaccharide other than α-galactosyl or a β-linked monosaccharide.

The present invention is also directed to pharmaceutical compositions comprising any of the α-galactosylceramides or glycosylceramides described above.

In further embodiments, the invention is directed to compositions comprising any of the α-galactosylceramides or glycosylceramides described above and a dendritic cell.

The invention is also directed to methods of administering a vaccine in a mammal. The methods comprise administering the vaccine in combination with any of the above α-galactosylceramides or glycosylceramides.

In additional embodiments, the invention is directed to methods of activating an NK T cell. The methods comprise contacting the NK T cell with any of the α-galactosylceramides or glycosylceramides described above.

The invention is additionally directed to methods of stimulating the immune system in a mammal. The methods comprise administering an effective amount of the above described pharmaceutical composition to the mammal.

The invention is further directed to methods of stimulating the immune system of a mammal by contacting dendritic cells with the above pharmaceutical composition and injecting the dendritic cells into the mammal.

In further embodiments, the invention is directed to methods of evaluating a compound for its ability to activate an NK T cell in the presence of a cell expressing a CD1d protein. The methods comprise combining the compound with the NK T cell in the presence of more than one cell type that expresses a CD1d protein and evaluating whether the NK T cell is activated.

The invention is also directed to methods of treating or preventing an autoimmune disease, cancer, or an infection in a mammal. The methods comprise administering to the mammal the above-described pharmaceutical composition.

DETAILED DESCRIPTION OF THE INVENTION

Figure 1:
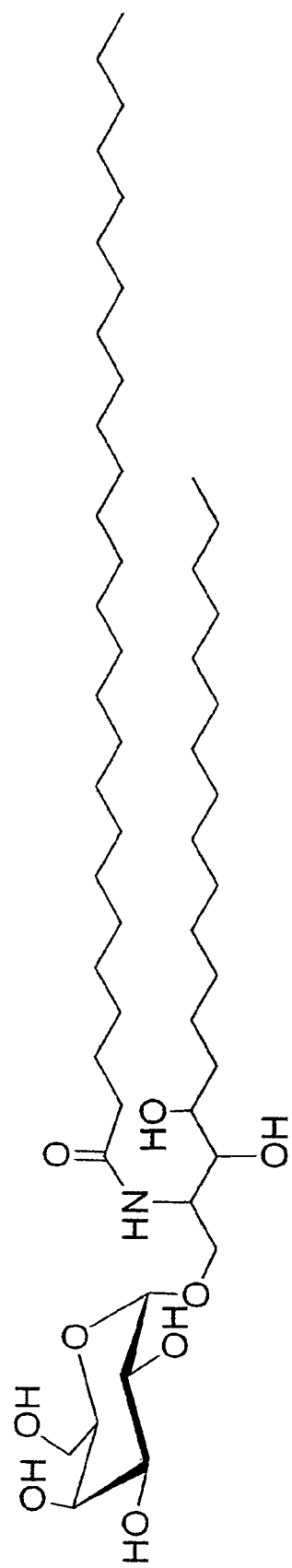
FIG. 1 shows the structure of the αGalCer KRN7000, a specific activator of CD1 d-restricted NK T cells. KRN7000 is ((2S,3S,4R)-1-O-(α-D-galactopyranosyl)-N-hexa-cosanoyl-2-amino-1,3,4-octadecanetriol). It contains a C18 phytosphingosine base and a C26 fatty acyl group. See U.S. Pat. No. 5,780,441.
Figure 2:
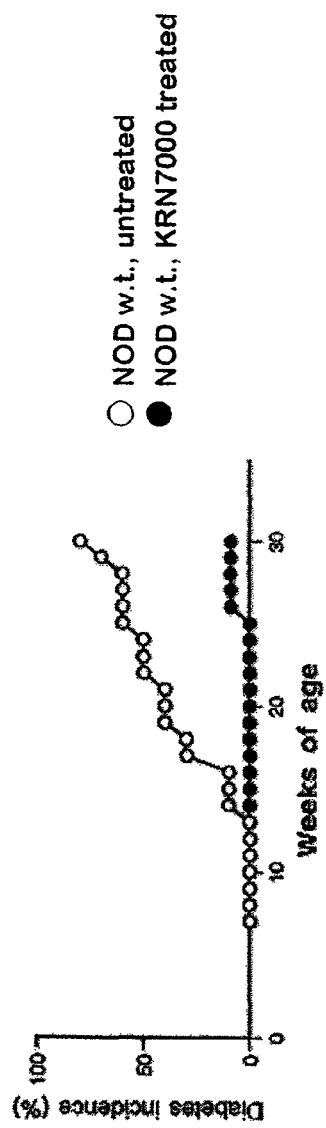
FIG. 2 shows data from Hong et al. (2001) that KRN7000 prevents development of type 1 diabetes in NOD mice. Mice received twice weekly injection with KRN7000 beginning at 4 weeks of age. Top graph shows reduction in incidence of diabetes from 75% to approximately 5%. Bottom graph shows that this effect is not seen in NOD mice that carry a knockout locus for CD1. These mice do not have CD1-restricted NK T cells, which are required for all of the known effects of KRN7000.
Figure 2:
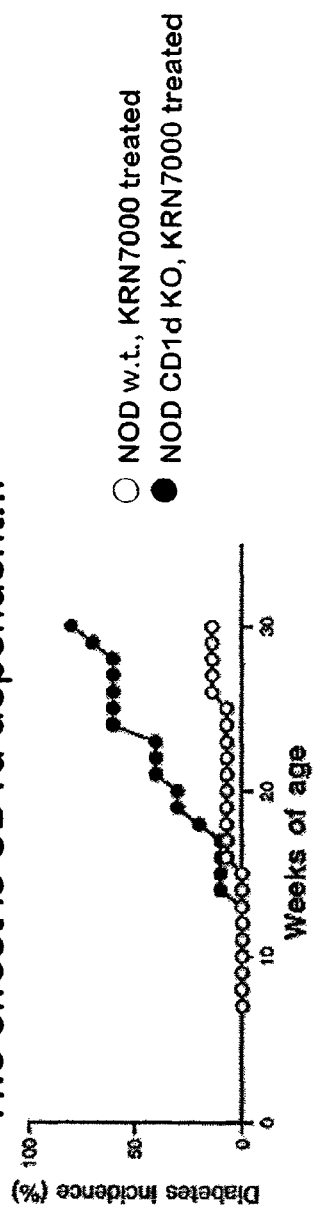
Figure 3:
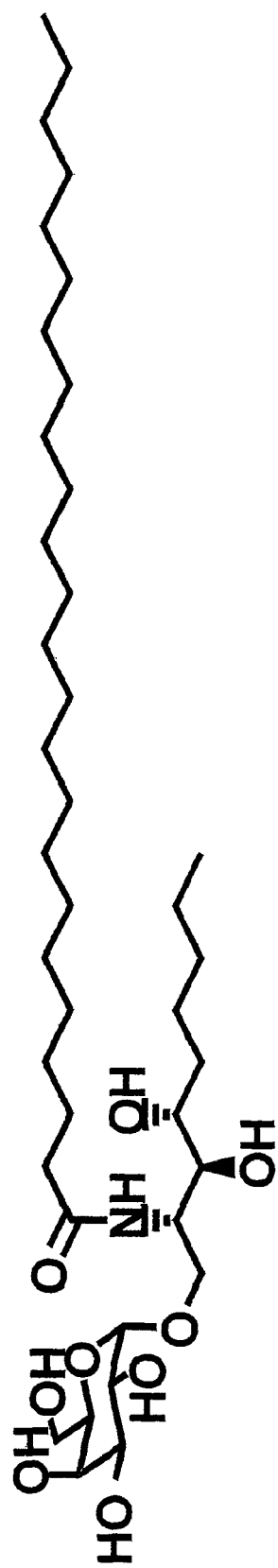
FIG. 3 shows the structure of OCH, an analogue of αGalCer with enhanced ability to suppress autoimmmune inflammation in mouse EAE. This differs from the KRN7000 structure in that it has a shortened C9 sphingosine base (as opposed to a C18 sphingosine base).
Figure 4:
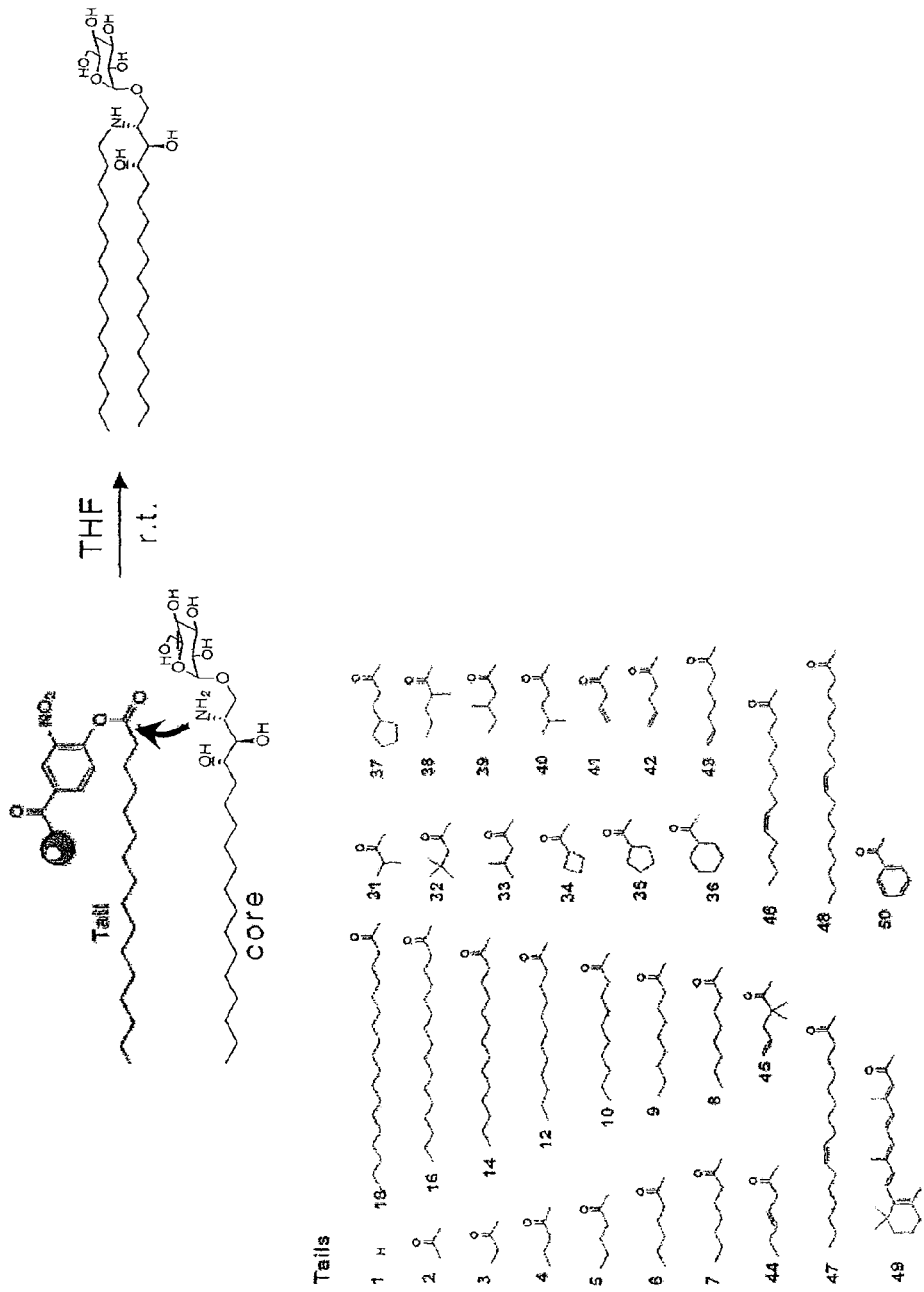
FIG. 4 shows the core structure and coupling reaction for synthesis of amino-substituted ceramide-like glycolipids identified in the present invention.

The present invention is based on the discovery that various ceramide-like glycolipids, i.e., α-galactosylceramides or other α-glycosylceramides, ("the ceramide-like glycolipids") are capable of modulating NK T cells, particularly variants in the moiety that is a fatty acid in KRN7000. The invention is also based on the discovery that the ceramide-like glycolipids differ in the type of cell that efficiently presents them, and that they can induce varied cytokine profile when used to activate NK T cells.

In one embodiment, the ceramide-like glycolipids activate cytokine production by the NK T cells. In another embodiment, the ceramide-like glycolipids suppress cytokine production by the NK T cells. In yet another embodiment, the ceramide-like glycolipids change the ratio of cytokines produced by the NK T cells.

Definitions:

The phrase "presents the compound," as used herein, means a cell binds the compound on the surface of the cell to provide a complex that causes the modulation of NK T cells.

The phrase "efficiently presents the compound," as used herein, means that cells will bind the compound on their surface to provide a complex that causes the modulation of NK T cells when the compound is present at a concentration of less than about 1 μM.

The term "modulate," "modulation," and the like, as used herein means, that a given function has been changed. For example, the phrase "a complex modulates the activity or activation of NK T cells" means that the complex causes the activity of NK T cells, for example, the production of cytokines, to be different from what it would have been in the absence of the complex. The alteration in activity can be, for example, an increase in the amount of cytokines produced in the presence of the complex compared to the amount of cytokines produced in the absence of the complex (activation or inducing of the NK T cell), or a decrease in the amount of cytokines produced in the presence of the complex compared to the amount of cytokines produced in the absence of the complex (suppression of the NK T cell), or a change in the ratio of different cytokines that are produced by the NK T cells.

The phrase "$C_6$-$C_{27}$ alkane," as used herein, means a straight chain or branched non-cyclic hydrocarbon having from 6 to 27 carbon atoms. Representative straight chain $C_6$-$C_{27}$ alkane include -methyl, -ethyl, -n-propyl, -n-butyl, -n-pentyl, -n-hexyl, -n-heptyl, -n-octyl, -n-nonyl and -n-decyl. Representative branched $C_6$-$C_{27}$ alkane include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

The phrase "$C_6$-$C_{27}$ alkene," as used herein means a straight chain or branched non-cyclic hydrocarbon having from 6 to 27 carbon atoms and including at least one carbon-carbon double bond. Representative straight chain and branched $C_6$-$C_{27}$ alkene include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The phrase "$C_5$-$C_{15}$ cycloalkane," as used herein, means a saturated cyclic hydrocarbon having from 5 to 15 carbon atoms. Representative $C_5$-$C_{15}$ cycloalkanes are -cyclopentyl, -cyclohexyl, -cycloheptyl, -cyclooctyl, -cyclononyl and -cyclodecyl. The phrase "$C_5$-$C_{15}$ cycloalkane" also encompasses bicycloalkanes and tricycloalkanes. The term bicycloalkane, as used herein, means a bi-cyclic hydrocarbon ring system having from 8 to 15 carbon atoms and at least one saturated cyclic alkyl ring. Representative bicycloalkanes include -indanyl, -1,2,3,4-tetrahydronaphthyl, -5,6,7,8-tetrahydronaphthy-1, -perhydronaphthyl, and the like. The term "tricycloalkanes," as used herein means a tri-cyclic hydrocarbon ring system having from 8 to 15 carbon atoms and at least one saturated ring. Representative tricycloalkanes include -pyrenyl, -1,2,3,4-tetrahydroanthracenyl, -perhydroanthracenyl-aceanthreneyl, -1,2,3,4-tetrahydropenanthrenyl, -5,6,7,8-tetrahydrophenanthrenyl, -perhydrophenanthrenyl, and the like.

The phrase "$C_5$-$C_{15}$ cycloalkene," as used herein, means a mono-cyclic non-aromatic hydrocarbon having at least one carbon-carbon double bond in the cyclic system and from 5 to 15 carbon atoms. Representative $C_5$-$C_{15}$ cycloalkenes include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl -cyclononadienyl, -cyclodecenyl, -cyclodecadienyl and the like. The phrase $C_5$-$C_{15}$ cycloalkene also encompasses bicycloalkenes and tricycloalkenes. The term "bicycloalkene," as used herein, means a bicyclic hydrocarbon ring system having at least one carbon-carbon double bond in one of the rings and from 8 to 15 carbon atoms. Representative bicycloalkenes include, but are not limited to, -indenyl, -pentalenyl, -naphthalenyl, -azulenyl, -heptalenyl, -1,2,7,8-tetrahydronaphthalenyl, and the like. The term "tricycloalkene," as used herein, means a tri-cyclic hydrocarbon ring system having at least one carbon-carbon double bond in one of the rings and from 8 to 15 carbon atoms. Representative bicycloalkenes include, but are not limited to, -anthracenyl, -phenanthrenyl, -phenalenyl, -acenaphthalenyl, as-indacenyl, s-indacenyl and the like.

The term "heterocycle, as used herein, means a 3- to 10-membered monocyclic or bicyclic heterocyclic ring which is either saturated, unsaturated non-aromatic, or aromatic containing up to 4 heteroatoms. Each heteroatom is independently selected from nitrogen, which can be quaternized; oxygen; and sulfur, including sulfoxide and sulfone. The heterocycle can be attached via a nitrogen, sulfur, or carbon atom. Representative heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyt, -carbazolyl, -β-carbolinyl and the like. The term heterocycle also includes heteroaryls. The term "heteroaryl" as used herein, mean an aromatic heterocycle ring of 5 to 10 members, including both mono- and bicyclic ring systems, wherein at least one carbon atom of one or both of the rings is replaced with a heteroatom independently selected from nitrogen, oxygen and sulfur. One or both of the heteroaryl's rings contain at least one carbon atom. Representative heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, thiadiazolyl, triazinyl, cinnolinyl, phthalazinyl, and quinazolinyl.

The phrase "aromatic ring," as used herein, means a 5 to 14 membered aromatic carbocyclic ring, including both mono, bicyclic, and tricyclic ring systems. Representative aromatic rings are phenyl, napthyl, anthryl and phenanthryl.

The phrase "oxo," as used herein, means a double bond to oxygen.

The phrase "halo," and "halogen," as used herein means chloro, bromo, iodo, and fluoro.

The term "adjuvant for a vaccine," as used herein, means any substance that non-specifically enhances immunogenicity of a specific antigen.

The phrase "treatment of" and "treating" includes the amelioration or cessation of a disease, disorder, or a symptom thereof.

The phrase "prevention of" and "preventing" includes the avoidance of the onset of a disease, disorder, or a symptom thereof.

The Ceramide-Like Glycolipids

In one embodiment, the invention is directed to ceramide-like glycolipids that are α-galactosylceramides comprising Formula I:

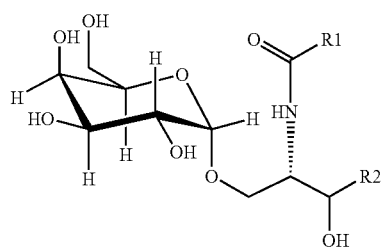

Formula I wherein

R1 is a linear or branched $C_1$-$C_{27}$ alkene with at least one C═C bond but not —$(CH_2)_7CH$═$CH(CH_2)_7CH_3$, or R1 is C(OH)—R3 wherein R3 is a linear or branched $C_1$-$C_{26}$ alkene with at least one C═C bond; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH$═$CH(CH_2)_xCH_3$,
(e) —$CH(OH)(CH_2)_xCH(CH_3)CH_2CH_3$, wherein X is an integer ranging from 5-17.

Ceramide-like glycolipids having moieties (a)-(e) in the sphingosine moiety are known to be capable of activating NK T cells. See U.S. Pat. No. 5,936,076. However, that patent did not evaluate whether variation in the fatty acid moiety would be capable of activating NK T cells.

In one embodiment, the sphingosine moiety (R2) is $CH(OH)(CH_2)_{13}CH_3$, which is the same as KRN7000, since that compound has been extensively evaluated.

As illustrated in the Examples several of the ceramide-like glycolipids are similar to, or stronger than, KRN7000 in their ability to activate NK T cells. These ceramide-like glycolipids can have various fatty acid lengths and numbers of unsaturated fatty acid bonds. Examples of the ceramide-like glycolipids include, but are not limited to, DB03-4, where R1 is $(CH_2)_9CH$═$CH$—$CH_2$—$CH$═$CH(CH_2)_4CH_3$; DB03-5, where R1 is $(CH_2)_2CH$═$CH$—$CH_2$—$CH$═$CH$—$CH_2$—$CH$═$CH$—$CH_2$—$CH$═$CH$—$(CH_2)_4CH_3$; DB03-6 where R1 is $(CH_2)_3CH$═$CH$—$CH_2$—$CH$═$CH$—$CH_2$—$CH$═$CH$—$CH_2$—$CH$═$CH$—$CH_2$—$CH$═$CH$—$CH_2$—$CH_3$; and DB03-10, where R1 is $(CH_2)_7CH$═$CH$—$CH_2$—$CH$═$CH$═$(CH_2)_4$—$CH_3$.

In one embodiment, the double bonds of the ceramide-like glycolipids have the cis configuration.

In one embodiment, the R2 moiety of the ceramide-like glycolipids is the same as KRN7000, i.e., CH(OH)$(CH_2)_{13}CH_3$.

In one embodiment, R1 includes at least two C═C bonds. In one embodiment, R1 includes at least two C═C bonds that are conjugated with each other, i.e., C═C—C═C.

In one embodiment, the ceramide-like glycolipids are capable of inducing or suppressing production of a cytokine. In one embodiment, the ceramide-like glycolipids induce cytokine production by an NK T cell at a level equal to or greater than that induced by the same concentration of KRN7000. The ceramide-like glycolipids also vary in the NK T immune response they elicit. For example, the ratio of different cytokines that are produced by the NK T cells can be different for different ceramide-like glycolipids, as illustrated in the Examples.

The capability of any of the ceramide-like glycolipids to induce or suppress cytokine production can be determined by measuring any cytokine that is produced by NK T cells. Methods for measuring cytokine production by NK T cells are well known to those skilled in the art. Any method known to those skilled in the art can be used to measure cytokine production by NK T cells including, but are not limited to, those described herein. In one embodiment, the cytokine is IL-2, IL-4 or IFNγ. Other cytokines whose production by NK T cells can be modulated using the ceramide-like glycolipids include, but are not limited to, $T_H2$-associated cytokines; the cytokines IL-13, IL-10, IL-5, RANTES, TNFα, and lymphotoxin.

Another measure of NK T cell induction is the expression of CD40L (CD154). See FIG. 11. Thus, measurement of the NK T cell-inducing efficacy of any of the ceramide-like glycolipids can also be determined by measuring the expression of CD40L. Methods for measuring expression of CD40L are well known to those skilled in the art. Any method known to those skilled in the art can be used to measure CDL40 expression including, but not limited to, those described in the examples. In one embodiment, CD40L levels are determined by staining with fluorescent-labeled anti-CD40L antibody followed by cell sorting by methods well known to those skilled in the art.

In one embodiment, modulation of cytokines or cell surface markers such as CD40L in NK T cells are accomplished with the ceramide-like glycolipids of the invention using an antigen-presenting cell (APC) line that expresses CD1d, for example a lymphoid line such as RMA-S.mCD1d, a myeloid lineage dendritic APC line such as JAWS II, or an epithelial APC line such as HeLa.hCD1d (see Example).

The present invention is also directed to ceramide-like glycolipids that are α-galactosylceramides comprising Formula I:

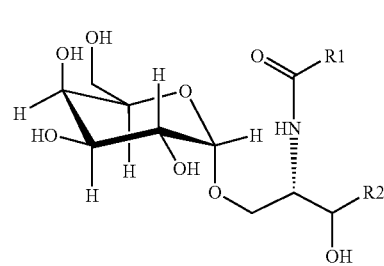

Formula I wherein

R1 is branched $C_1$-$C_{27}$ alkane or

R1 is C(OH)—R3 where R3 is a linear or branched $C_1$-$C_{26}$ alkene; and

R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 5-17.

In one embodiment of these α-galactosylceramides R2 is CH(OH)(CH$_2$)$_{13}$CH$_3$, i.e., the same as KRN7000.

In one embodiment, R1 includes at least two C=C bonds. In one embodiment, R1 includes at least two C=C bonds that are conjugated with each other, i.e., C=C—C=C.

In further embodiments, the invention is directed to ceramide-like glycolipids that are α-galactosylceramides comprising Formula I:

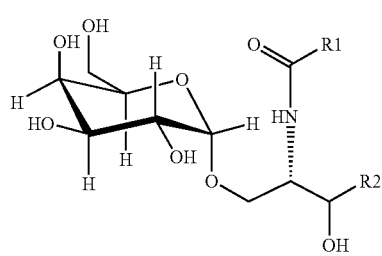

Formula I wherein

R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring; and R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 5-17.

In one embodiment of these compounds, R2 is CH(OH)(CH$_2$)$_{13}$CH$_3$. i.e., the same as KRN7000.

In some embodiments, R1 is substituted with oxo; hydroxy; halogen; —OC(O)R$_5$; —OR$_5$; —C(O)R$_5$; or N(R$_5$)$_2$ wherein each R$_5$ is independently hydrogen, C$_1$-C$_6$ alkyl, or an aromatic ring optionally substituted with halogen, hydroxy, halogen, —OC(O)R$_6$, —OR$_6$, —C(O)R$_6$, N(R$_6$)$_2$ wherein each R$_6$ is independently hydrogen or C$_1$-C$_6$ alkyl.

In one embodiment, R1 is a C$_6$-C$_{27}$ alkane or alkene wherein the C$_6$-C$_{27}$ alkane or alkene is substituted with a C$_5$-C$_{15}$ cycloalkane, C$_5$-C$_{15}$ cycloalkene, heterocycle, or aromatic ring.

In one embodiment R1 is a C$_6$-C$_{27}$ alkane or alkene wherein the C$_6$-C$_{27}$ alkane or alkene includes, within the chain, a C$_5$-C$_{15}$ cycloalkane, C$_5$-C$_{15}$ cycloalkene, heterocycle, or aromatic ring.

In one embodiment, R1 includes at least two C=C bonds. In one embodiment, R1 includes at least two C=C bonds that are conjugated with each other, i.e., C=C—C=C.

In other embodiments, R1 is one of the following moieties:

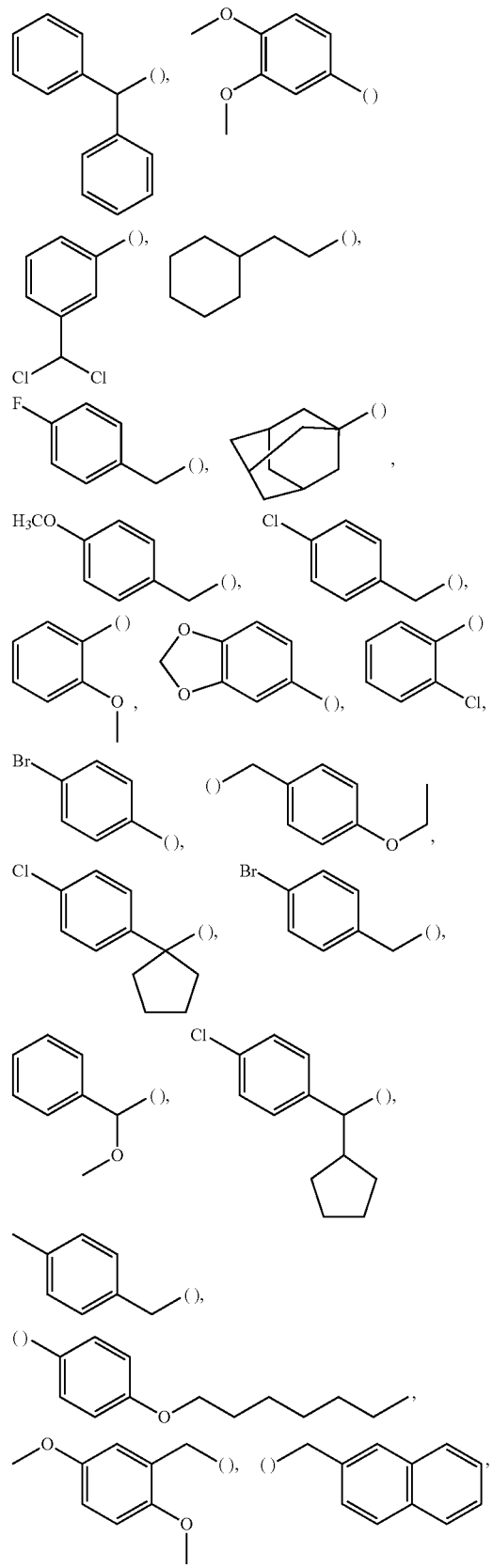

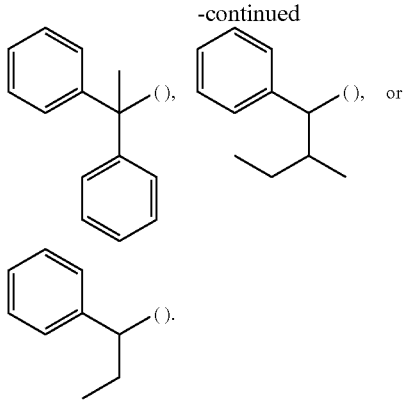

where ( ) represents the point of attachment of R1 to the compound of Formula I. Examples of these compounds are DB03-4, DB03-5, and YTC03 compounds 4, 6, 11, 15, 17, 18, 24, 25, 27, 29, 30, 31, 33, 34, 35, 36, 38, 39, 40, 41, 43, 44, 45, 46, 47, 48, 49, 50, 51, 52, 53, 54, 56, 58, 59, 60 and 61 (see Example, FIG. 5 and Table 1). Particularly effective compounds are DB03-4 and YTC03 compounds 6, 17, 25, 31, 33, 35, 46, 47, 50, 56, 59 and 60.

In other embodiments of these α-galactosylceramides, R2 is $CH(OH)(CH_2)_{13}CH_3$, as in KRN7000.

In additional embodiments, the invention is directed to ceramide-like glycolipids that are α-galactosylceramides comprising Formula I:

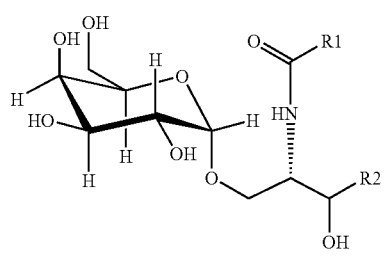

Formula I wherein

R1 is selected from the group consisting of —C(=O)OCH$_2$CH$_3$, —(CH$_2$)$_6$CH$_3$, —(CH$_2$)$_4$Cl, —(CH$_2$)$_{16}$CH$_3$, —(CH$_2$)$_5$CH$_3$, —(CH$_2$)$_2$CH$_3$, —(CH$_2$)$_4$CH$_3$, —(CH$_2$)$_8$CH$_3$, —(CH$_2$)$_{10}$CH$_3$, —(CH$_2$)$_{12}$CH$_3$; and R2 is one of the following (a)-(e):

(a) —CH$_2$(CH$_2$)$_x$CH$_3$, (b) —CH(OH)(CH$_2$)$_x$CH$_3$, (c) —CH(OH)(CH$_2$)$_x$CH(CH$_3$)$_2$, (d) —CH=CH(CH$_2$)$_x$CH$_3$, (e) —CH(OH)(CH$_2$)$_x$CH(CH$_3$)CH$_2$CH$_3$, wherein X is an integer ranging from 5-17.

As illustrative examples, see, e.g., compounds YTCO3-4, 6, 11, 15, 25, 27, 31, 34, 35, and 36 in FIG. 5.

As with the other embodiments described above, R2 is $CH(OH)(CH_2)_{13}CH_3$, as in KRN7000.

The inventors have also discovered that the galactose moiety of αGalCer can be substituted with a other α-linked monosaccharides, where the resulting α-glycosylceramide is capable of activating an NK T cell. See FIGS. 5D and 11, and the Example. Thus, the present invention is also directed to ceramide-like glycolipids that are glycosylceramides comprising Formula II:

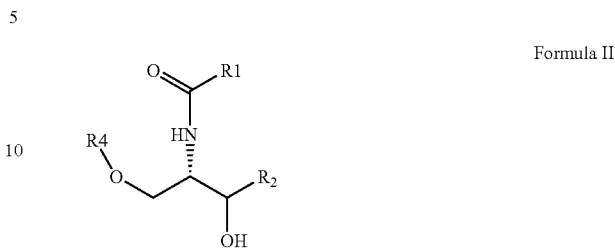

Formula II wherein

R1 is a linear or branched C$_1$-C$_{27}$ alkane or alkene, or

R1 is C(OH)—R3 wherein R3 is a linear or branched C$_1$-C$_{26}$ alkene with at least one C=C bond, or R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring;

R2 is one of the following (a)-(e):

(a) —CH$_2$(CH$_2$)$_x$CH$_3$, (b) —CH(OH)(CH$_2$)$_x$CH$_3$, (c) —CH(OH)(CH$_2$)$_x$CH(CH$_3$)$_2$, (d) —CH=CH(CH$_2$)$_x$CH$_3$, (e) —CH(OH)(CH$_2$)$_x$CH(CH$_3$)CH$_2$CH$_3$, wherein X is an integer ranging from 5-17; and R4 is an α-linked monosaccharide other than α-galactosyl or a α-linked monosaccharide.

In one embodiment, R4 is an α-linked monosaccharide other than α-galactosyl.

In one embodiment, the α linked monosaccharide is α-glucosyl.

In another embodiment, the α linked monosaccharide is α-fucosyl.

In another embodiment, the α linked monosaccharide is α-mannosyl.

In one embodiment, R4 is an β-linked monosaccharide.

In one embodiment, the β-linked monosaccharide is β-mannosyl.

In one embodiment, R1 includes at least two C=C bonds. In one embodiment, R1 includes at least two C=C bonds that are conjugated with each other, i.e., C=C—C=C.

Figure 5A:
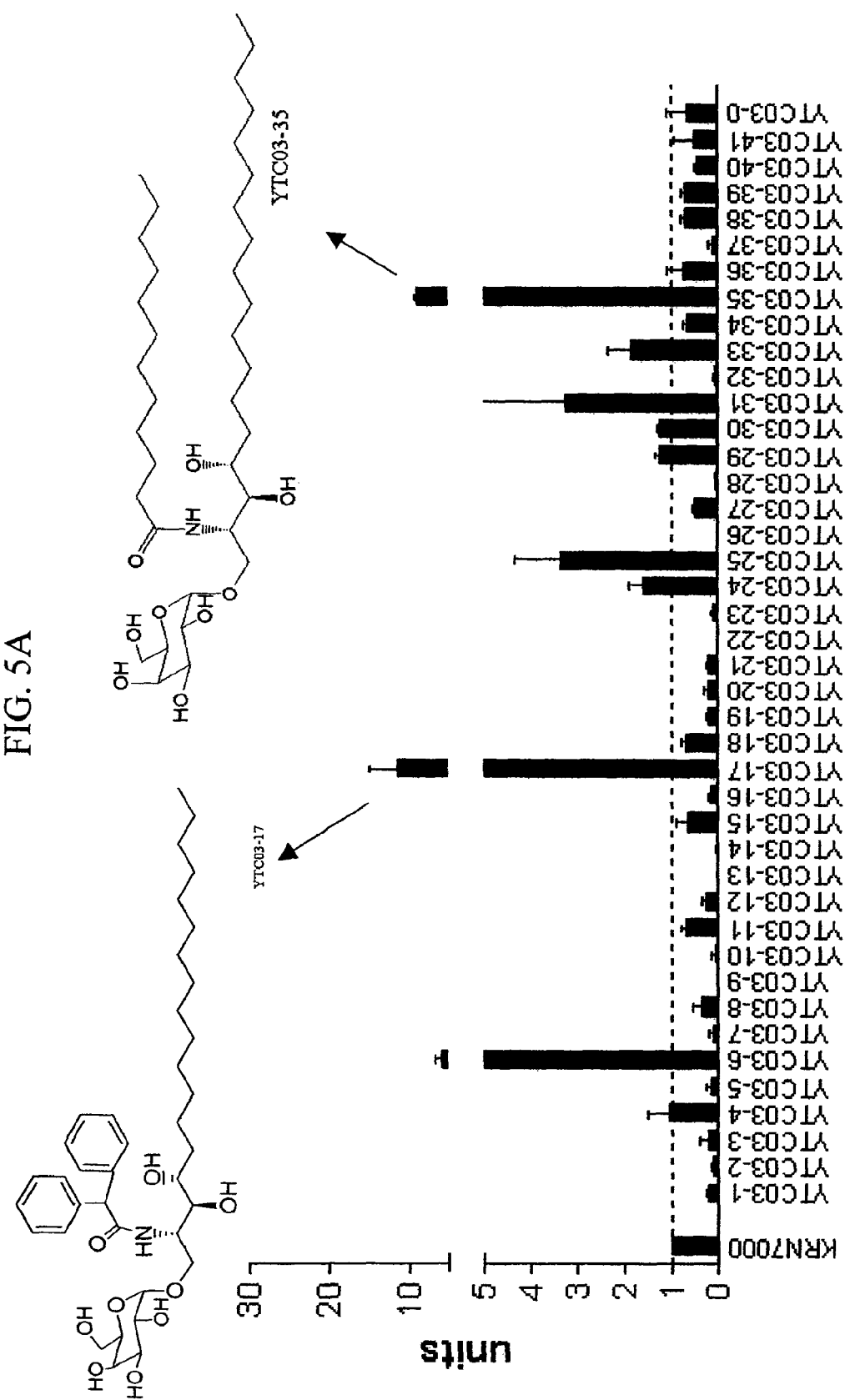
FIG. 5. Panel A shows experimental results of bioactivity screens of ceramide-like glycolipids produced by combinatorial synthesis. NK T hybridoma DN32.D3 was cultured with CD1d-transfected RMA-S cells in microtiter plate wells. Each ceramide-like glycolipid was titrated over a concentration range from 0.5-500 nM, and supernatants were harvested after 24 hours for measurement of IL-2 release. Units of activity were calculated as the reciprocal of the concentration of ceramide-like glycolipid required to give a half maximal release of IL-2, and all values were normalized to the activity of KRN7000 (defined as 1 Unit). The dotted line indicates the level of activity for KRN7000. The structures of two ceramide-like glycolipids with markedly elevated activity relative to KRN7000 are shown. Panel B shows the structures of the ceramide-like glycolipids tested in the experiments described in Panel A and Table 1. Panel C shows a graphical representation of the results from Table 1. Panel D shows stimulation of CD1d-dependent proliferation by DB02-1, an α-glucosyl ceramide identical to DB01-1, except with a glucose replacing the galactose of DB01-1.
Figure 5C:
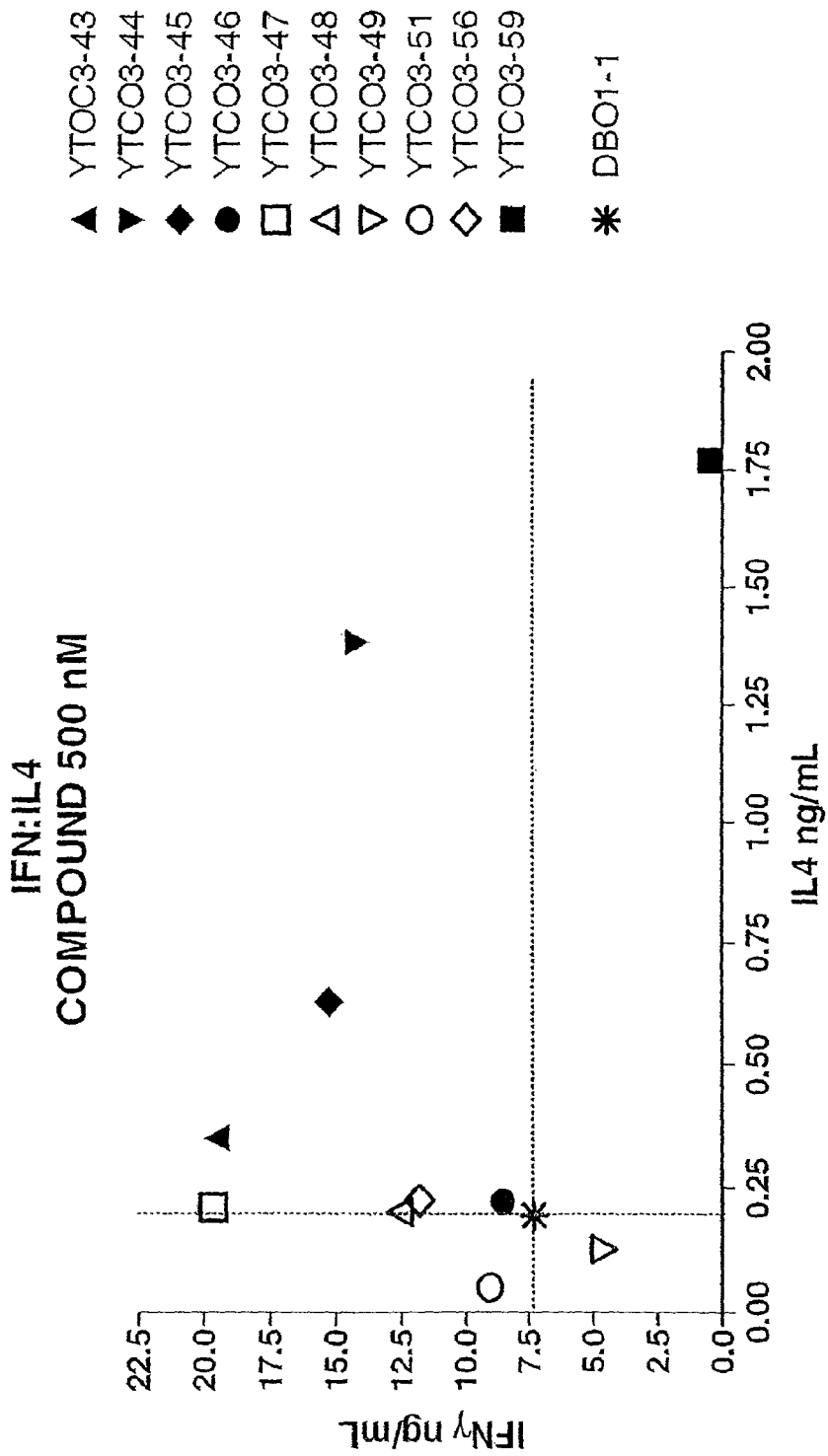
Figure 5D:
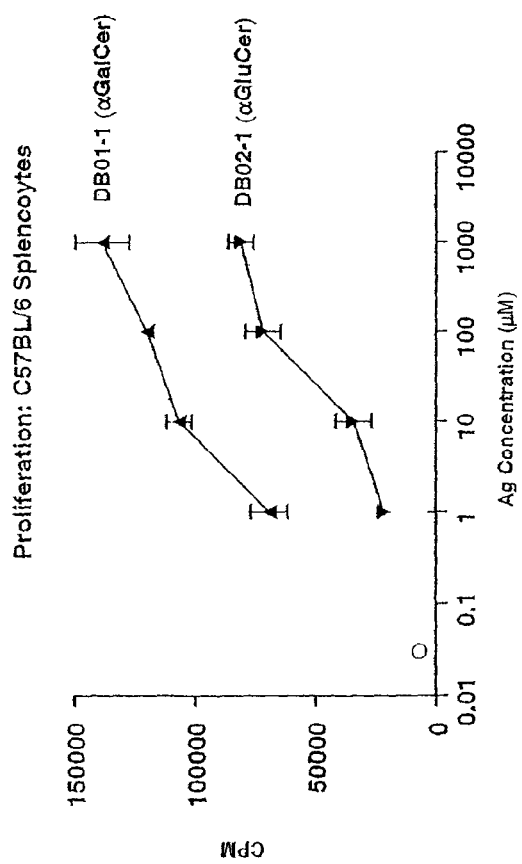

An example of a member of these embodiments is DB03-8 (FIG. 5B) where R4 is a fucose and R1 is (CH$_2$)$_{22}$—CH$_3$ (see Example and FIG. 11), and DB02-1 where R4 is a glucose (see Example and FIG. 5D). In one embodiment, R2 is CH(OH)—(CH$_2$)$_{13}$—CH$_3$. In one embodiment R1 is (CH$_2$)$_{22}$—CH$_3$ and R2 is CH(OH)—(CH$_2$)$_{13}$—CH$_3$. However, any of the R1 moieties that were effective in the α-galactosylceramides disclosed above would be expected to be useful in the α-glycosylceramides. Examples of monosaccharides (at the R4 position) in these embodiments are glucose, fucose, galactose, and mannose.

Representative examples wherein R4 is an β-linked monosaccharide are DB04-8 and DB04-9.
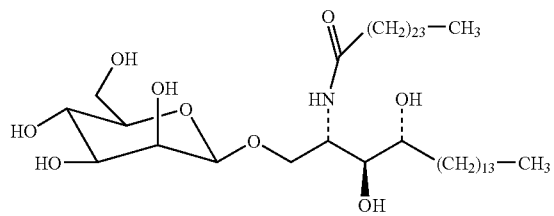
DB04-8
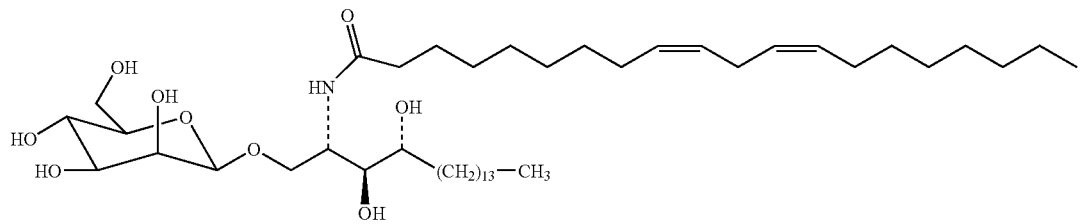
DB04-9
Some representative ceramide-like glycolipids of the invention are provided in the table below:
| Compound | Molecular Weight | Structure |
|---|---|---|
| DB03-4 | 770.13 | 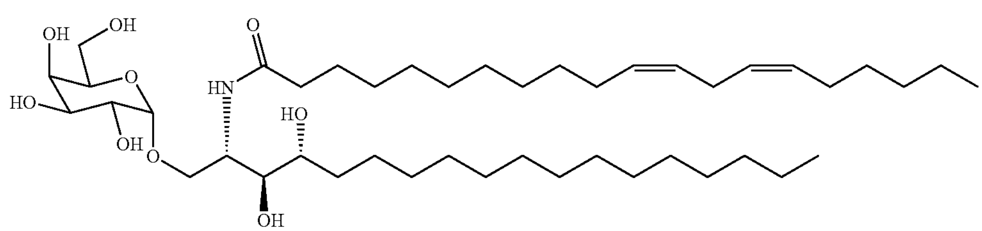 |
| DB03-5 | 766.13 | 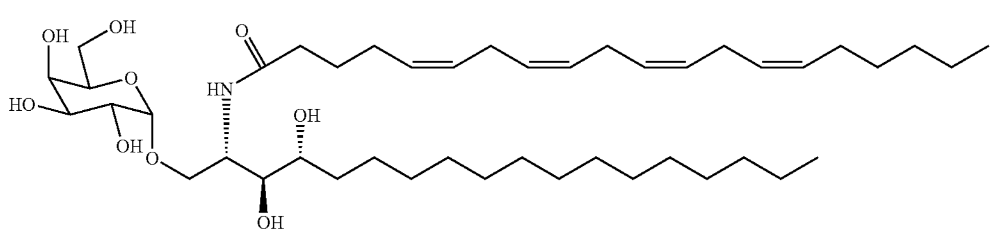 |
| DB03-3 | 772.15 | 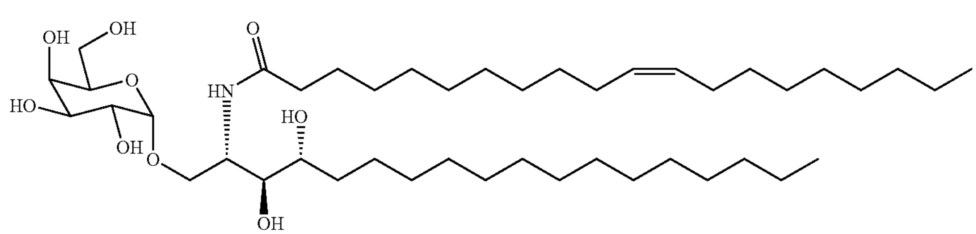 |

-continued
| Compound | Molecular Weight | Structure |
|---|---|---|
| DB03-10 | 742.08 | 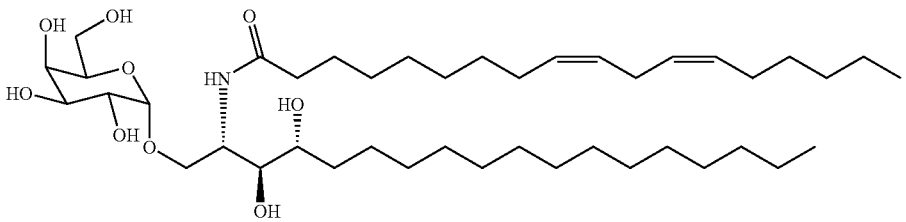 |
| DB04-9 | 770.13 | 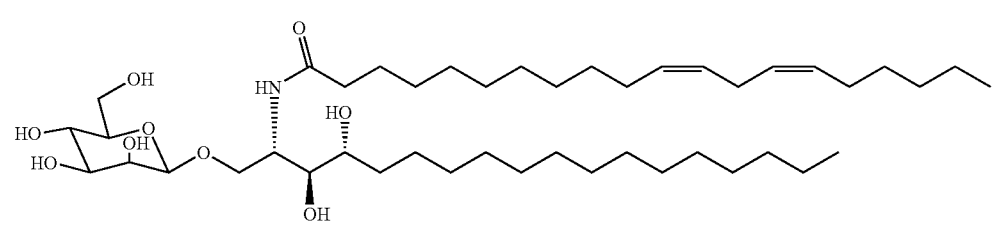 |
| DB03-8 | 886.42 | 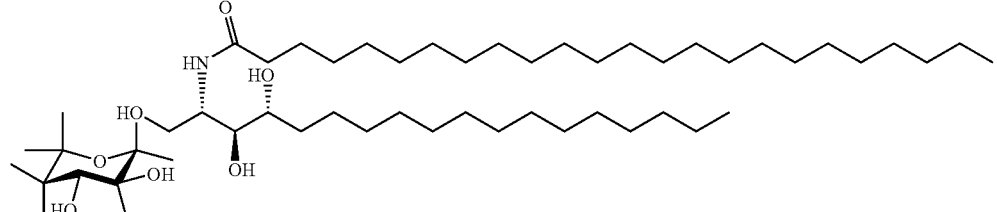 |
| YTC03-17 | 705.96 | 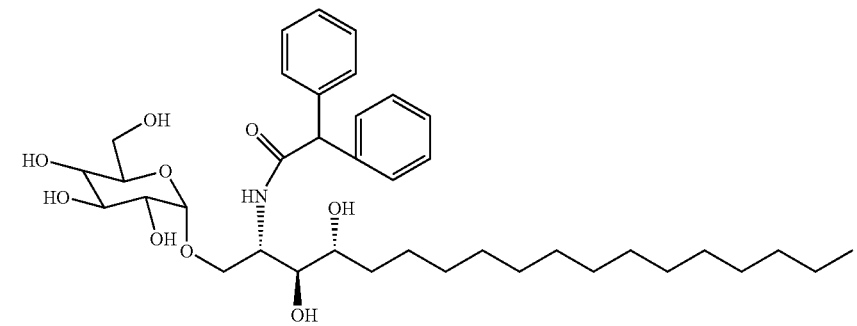 |
| YTC03-24 | 657.83 | 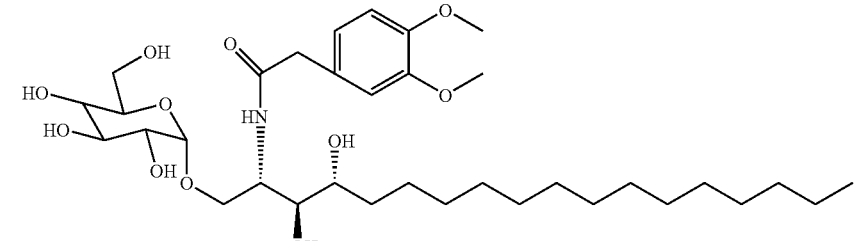 |
| YTC03-25 | 591.82 | 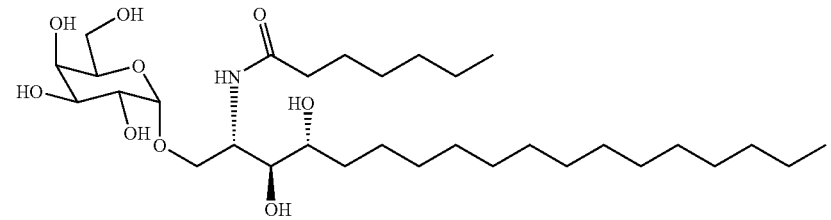 |

| Compound | Molecular Weight | Structure |
|---|---|---|
| DB03-6 | 764.13 | (structure: α-galactosyl ceramide analog with polyunsaturated acyl chain) |

In vivo activity refers to activity in mice (see Example).
In vitro Activity refers to activity in a murine cell assay system (see Example).

Each of the DB03-3, DB03-4, DB03-5, DB03-7, DB03-8, DB03-9, DB03-10, and YTC03-17 show in vitro activity at modulating cytokines using a murine cell assay system (see Example) and, for several of the compounds, activity has also been shown in a human in vitro NKT cell assay system. For example, DB03-4 and DB03-5 are active in stimulation of human NKT cell clones in vitro, and elicits proliferative responses and cytokine secretion when evaluated using culture systems previously established in the literature (See, e.g., Spada F M, Sugita M, Watts G F M, Koezuka Y, and Porcelli S A. Low expression but potent antigen presenting function of CD1d on monocyte lineage cells, *Eur. J. Immunol.*, 30:3468-3477 (2000), and Spada F M, Koezuka Y, Porcelli S A, CD1d-restricted recognition of synthetic glycolipid antigens by human NK T cells. *J Exp Med;* 188:1529-1534 (1998), see also, Lee P T et al., *J Clin Invest.*, 2002 September; 110(6): 793-800. In addition, these compounds can be used to create glycolipid human CD1d tetramers that bind strongly to human NKT cells in normal blood specimens, indicating that these glycolipids, when presented by human CD1d, are avidly recognized by the T cell antigen receptors of human NKT cells (methods for CD1 d tetramer production and application to studying NKT cells are described in Yu K O A, Im J S, Molano A, Dutronc Y, Illarionov P A, Forestier C, Fujiwara N, Arias I, Miyake S, Yamamura T, Chang Y-T, Besra G S, Porcelli S A, Modulation of CD1d-restricted NKT cell responses using N-acyl variants of α-galactosylceramides, Proc. Nat. Acad. Sci. (USA), 102:3383-8 (2005)).

Several of these compounds also showed activity at modulating cytokines in mice (see, examples). Both DB03-4 and DB03-5 show a bias towards inducing Type 2 cytokines, i.e., cytokines that have anti-inflammatory effect, and are strong inducers of IL-4 in iNKT cells with blunted IFNγ and NK cell transactivation. DB03-3 is a good inducer of L-4 and, in some murine strains, a strong inducer of IFNγ in vitro. High level production of IFNγ is often associated with NK cell activation. DB03-9, and DB03-10 are strong inducers of IL-4, weak inducers of IL-2, and moderate inducers of IFNγ in vitro. YTC03-17 shows strong agonist activity in in vitro studies. DB03-8 is a weak agonist of iNKT cells in vitro and exacerbates SLE in NZB/W-F1 mice. It is believed that DB03-8 may be a possible antagonist/partial agonist, i.e., it inhibits the direct and indirect activity of iNKT because it acts as an antagonist of iNKT or because it stimulates an abortive partial activation.

The term iNKT cells, as used herein, mean the specific subset of CD1d-dependent T cells that expresses the invariant TCRα chain rearrangement consisting of Vα14-Jα18 in mice, and Vα24-Jα18 in humans. These cells are uniformly reactive to α-galactosylceramides presented by CD1d. These cells are also referred to as "Type 1" NKT cells, and the distinction between the different types of NKT cells and the nomenclature relating to this are summarized in the publication by Godfrey et al., Nat Rev Immunol. 2004 March; 4(3): 231-7. Methods for determining cytokine production by iNKT cells in response to CD1d-presented glycolipids for determination of strong or weak agonist activity are described in Yu K O A, Im J S, Molano A, Dutronc Y, Illarionov P A, Forestier C, Fujiwara N, Arias I, Miyake S, Yamamura T, Chang Y-T, Besra G S, Porcelli S A, Modulation of CD1d-restricted NKT cell responses using N-acyl variants of α-galactosylceramides, Proc. Nat. Acad. Sci. (USA), 102:3383-8 (2005), see also Godfrey D I et al., *Nat Rev Immunol.* 2004 March; 4(3):231-7.

YTC03-24 and YTC03-25 show enhanced IL-4 induction relative to IFNγ in vitro with splenocytes from NZB/W F1 mice. DB03-6 is an agonist in splenocyte cultures with apparent enhancement of IL-4 relative to IFNγ and minimal IL-2 induction.

Additional representative ceramide-like glycolipids of the invention include those provided in the table below:

| Compound | Monosaccharide | Molecular Weight | Structure |
|---|---|---|---|
| DB04-01 (KRN7000)[a] | α-D-Gal | 858.32 | (structure: α-galactosyl ceramide KRN7000) |

-continued

| Compound | Mono-saccharide | Molecular Weight | Structure |
|---|---|---|---|
| DB01-1 | α-D-Gal | 830.27 | 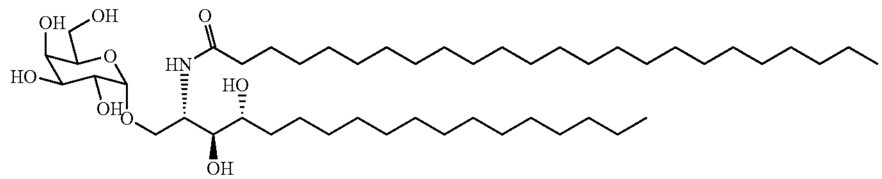 |
| DB02-1 | α-D-Glu | 830.27 | 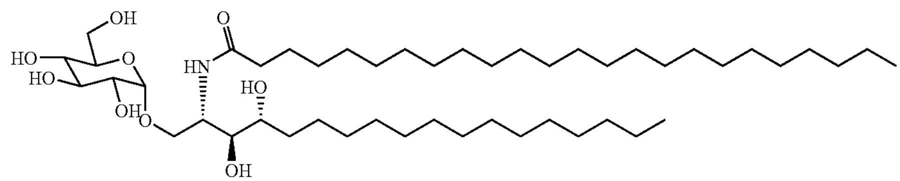 |
| DB03-4 | α-D-Gal | 770.13 | 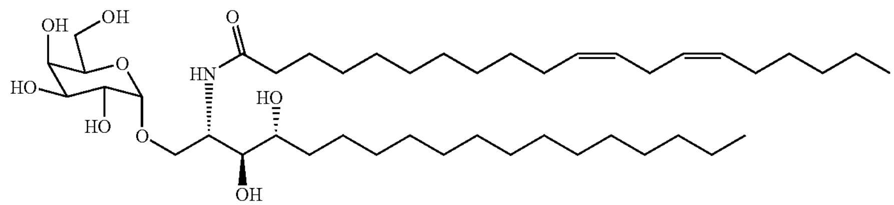 |
| DB03-5 | α-D-Gal | 766.10 | 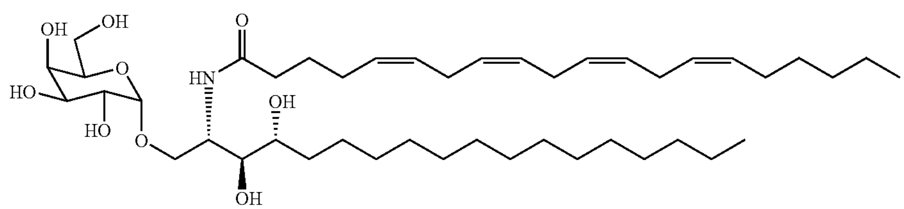 |
| DB03-8 | α-L-Fuc | 814.27 | 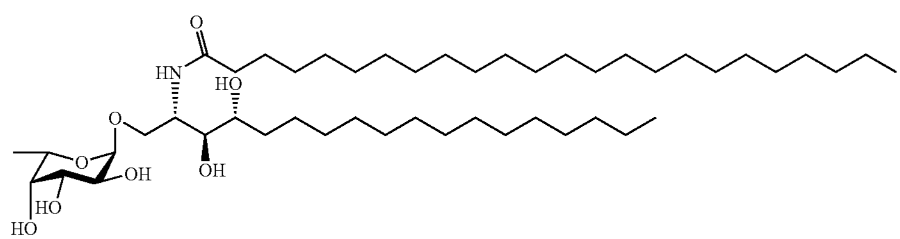 |
| DB04-9 | β-D-Man | 770.13 | 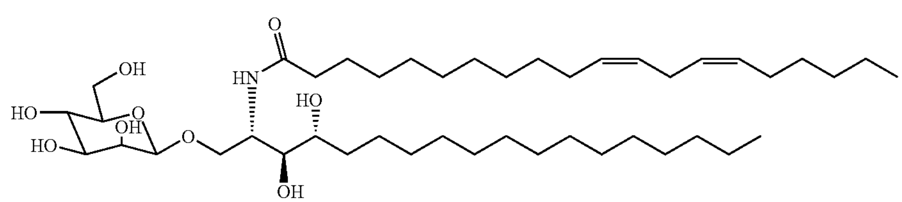 |
| DB05-9 | α-D-Gal | 742.08 | 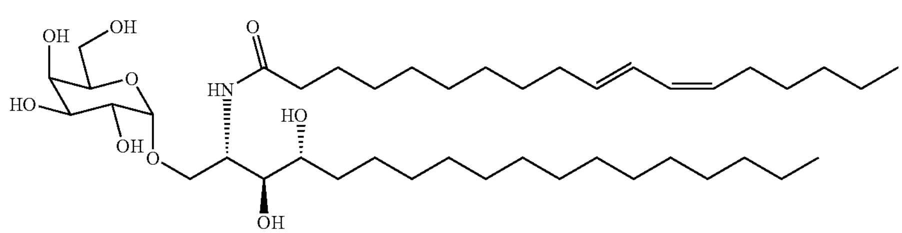 |

-continued

| Compound | Mono-saccharide | Molecular Weight | Structure |
|---|---|---|---|
| DB05-10 | α-D-Gal | 740.06 | 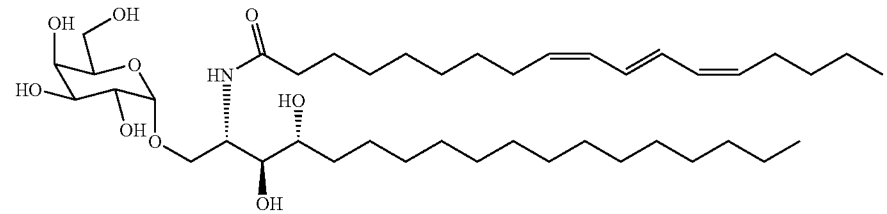 |
| DB05-11 | α-D-Gal | 742.08 | 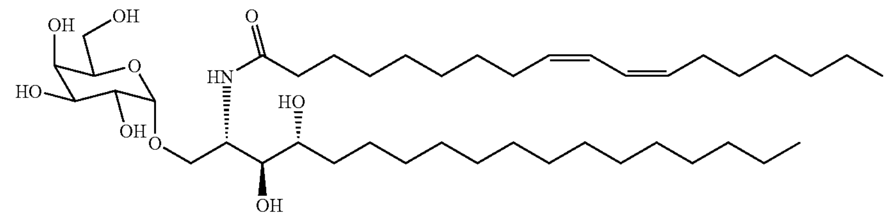 |
| DB05-12 | α-D-Gal | 770.13 | 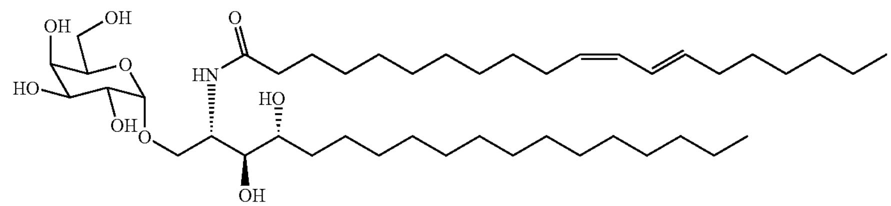 |
| DB05-14 | α-D-Gal | 740.06 | 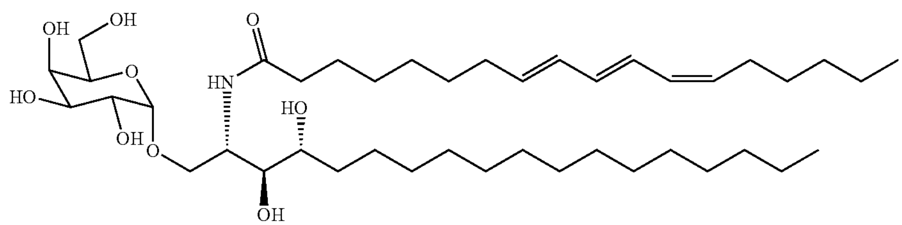 |
| DB05-15 | α-D-Gal | 742.08 | 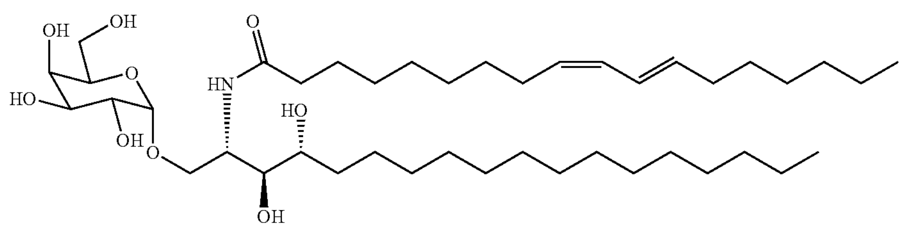 |
| DB05-16 | α-D-Gal | 742.08 | 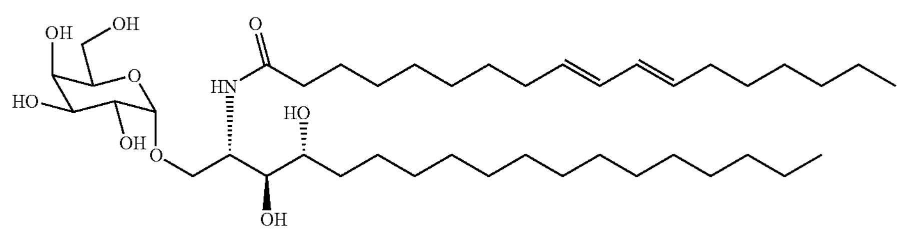 |
| DB05-17 | α-D-Gal | 740.06 | 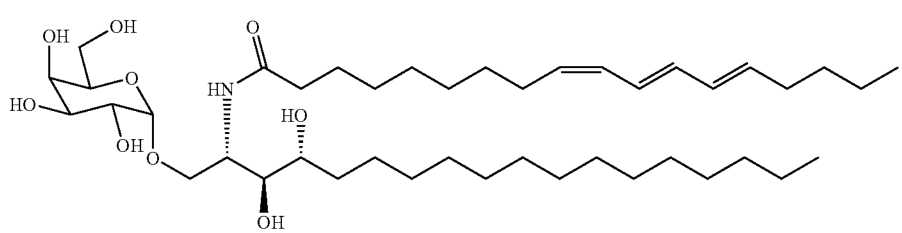 |

-continued

| Compound | Mono-saccharide | Molecular Weight | Structure |
|---|---|---|---|
| DB06-14 | α-L-Fuc | 842.32 | 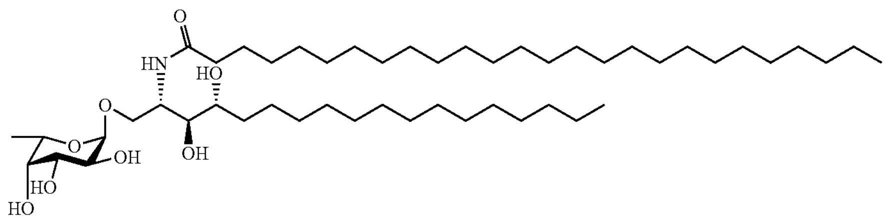 |
| DB06-15 | α-D-Glu | 770.13 | 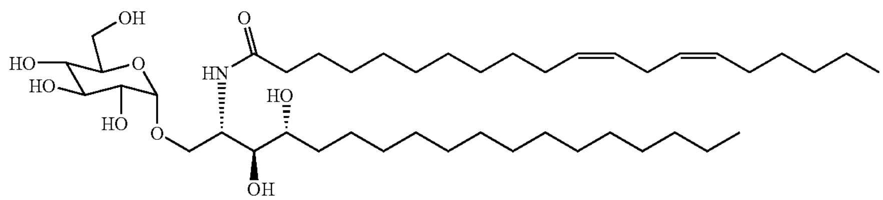 |
| YTC03-15 | α-D-Gal | 746.11 | 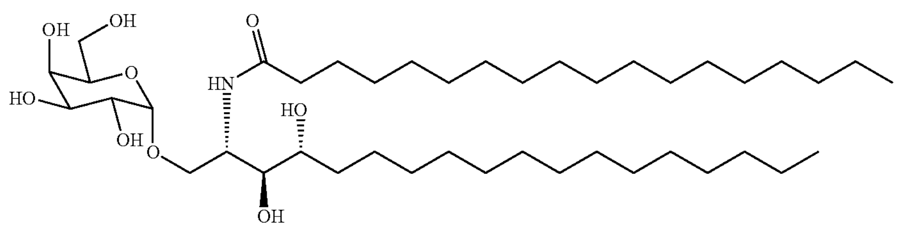 |
| YTC03-17 | α-D-Gal | 705.96 | 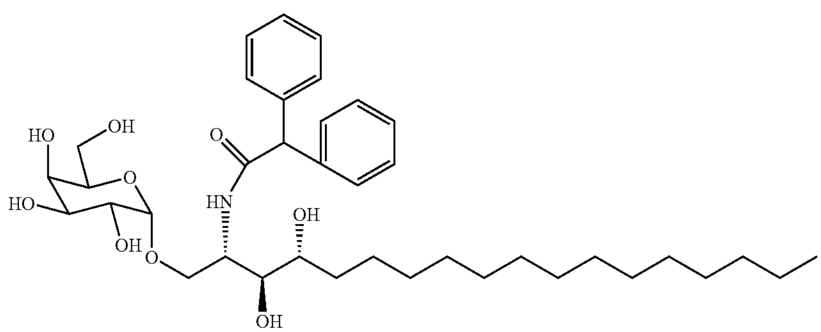 |
| YTC03-24 | α-D-Gal | 657.83 | 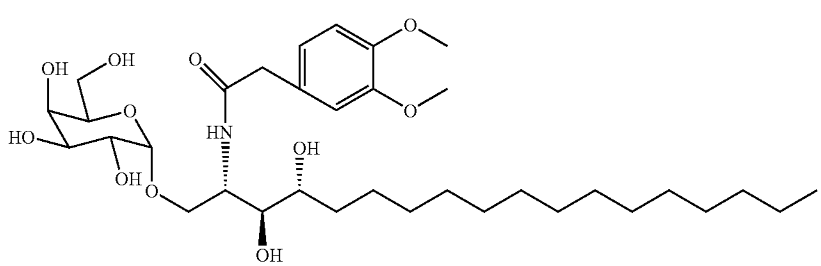 |
| YTC03-30 | α-D-Gal | 615.77 | 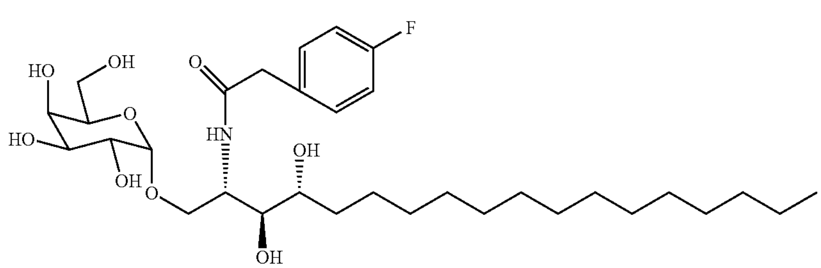 |

| Compound | Mono-saccharide | Molecular Weight | Structure |
|---|---|---|---|
| YTC03-33 | α-D-Gal | 627.81 | 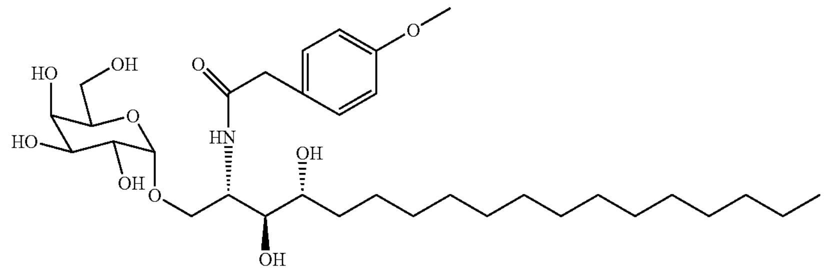 |
| YTC03-34 | α-D-Gal | 633.90 | 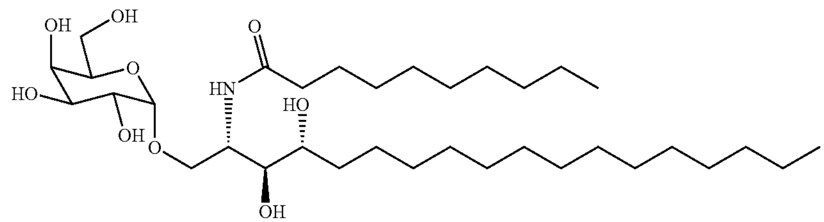 |
<sup>a</sup>DB04-01 (KRN7000) is not a compound of the invention.
The following synthetic scheme depicts a synthetic methodology used to make the ceramide-like glycolipids:
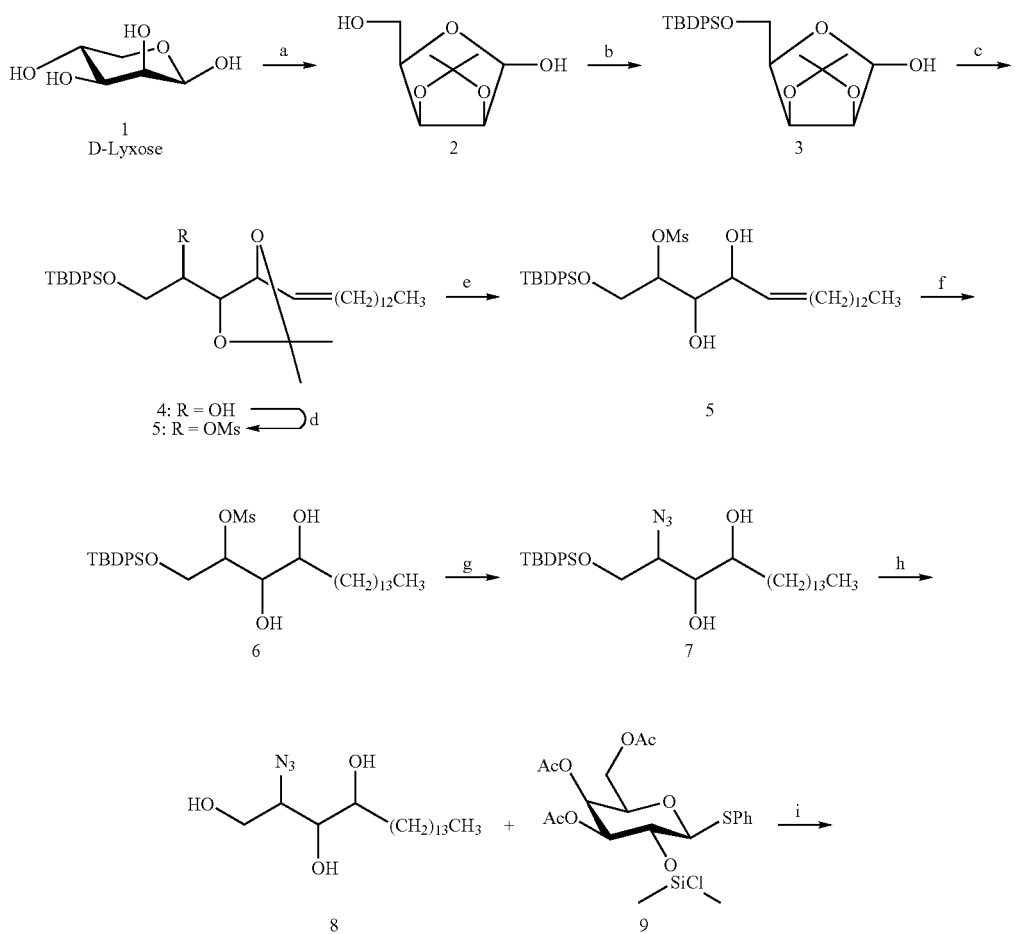

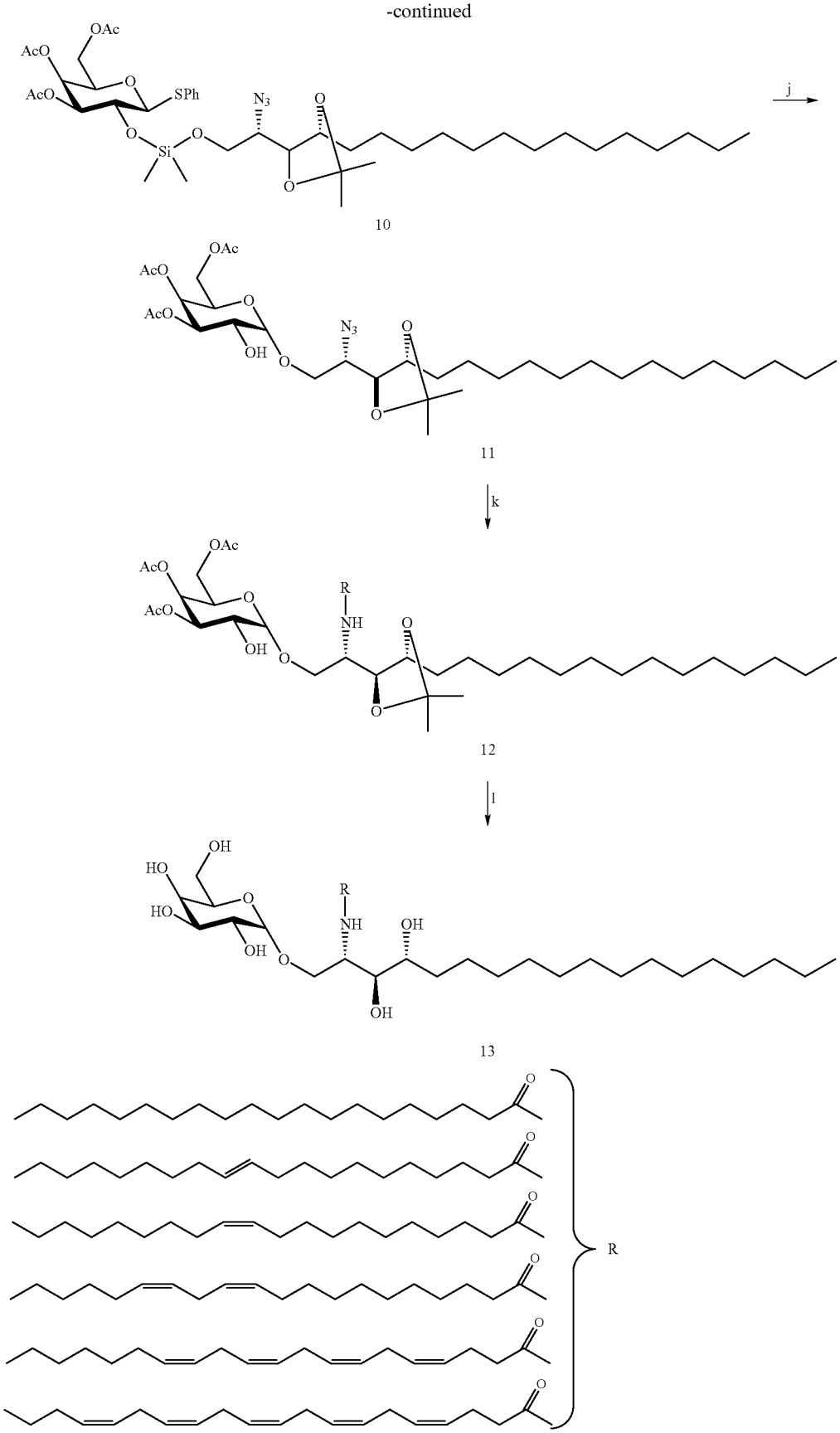

Using this synthetic process an azido sphingosine precursor (compound 8) is prepared from D-lyxose by reacting D-lyxose (compound 1) with acetone/$H_2SO_4$ for about 18 h at room temperature to provide compound 2 (step a). Compound 2 is then reacted with tert-butyl di-propyl silyl chloride (TBDPSCl) and 4-dimethylamino pyridine (DMAP) and $Et_3N$ in $CH_2Cl_2$ for about 16 h at room temperature to provide compound 3 (step b). Compound 3, is then reacted with triphenylphosphine ($Ph_3P$), 1-bromodecane, and BuLi in tetrahydrofuran (THF) at about 0° C. followed by allowing the reaction mixture to warm to room temperature and remain at room temperature for about 18 h to provide compound 4 (step c). Compound 4 is then reacted with mesyl chloride (MsCl) and pyridine in $CH_2Cl_2$ at about 31° C. for about 24 h to provide compound 5 (step d). Compound 5 is then reacted with HCl in $CH_2Cl_2$/MeOH for about 2 h at room temperature to provide compound 5 (step e). Compound 5 is reacted with $H_2$ using a Pd/$BaSO_4$ catalyst for about 20 h at room temperature to provide compound 6. Compound 6 is reacted with $NaN_3$ in dimethylformamide (DMF) at about 95° C. for about 4 h to provide compound 7. Compound 7 is then reacted with tetra-butyl ammonium fluoride (TBAF) (80%) to provide the azido sphingosine precursor (compound 8).

The 3,4-dihydroxy group of the azido sphingosine precursor (compound 8) is then protected as an isopropylidene acetal and coupled to the acetyl protected thiophenyl galactose bearing a chloro-dimethyl silyl ether at position-2 (compound 9) to provide the glycosyl intermediate (compound 10). The α-galactosyl azido sphingosine intermediate (compound 11) is obtained using an intramolecular aglycon delivery strategy, whereby the thioglycoside is activated by benzensulfinylpiperidine (BSP)/trifluoromethanesulfonic anhydride ($Tf_2O$), as described by D. Crich and M. Smith. in *J. Am. Chem. Soc.*, 123:9015 (2001). The azide group of compound 11 is then reduced to an amine and N-acylated with the appropriate fatty acid that has been activated as an acid chloride to provide compound 12. The remaining hydroxyl protecting groups are then removed from compound 12 using acidic and basic conditions to afford the ceramide-like glycolipid (compound 13). See also K Yu et al. PNAS, Mar. 1, 2005, 102:(9), 3383-3388.

Other methods known to those skilled in the art can also be used to prepare the ceramide-like glycolipids. For example, the ceramide-like glycolipids can also be obtained using the methodology described in U.S. Pat. No. 5,936,076.

Pharmaceutical Compositions, Methods of Administration, and Methods of Use:

Since the ceramide-like glycolipids are expected to be useful in vaccines or in treatments of disorders such as autoimmune diseases, various cancers or infections, pharmaceutical compositions comprising the ceramide-like glycolipids are also contemplated.

Accordingly, the invention further relates to a pharmaceutical composition comprising the ceramide-like glycolipids and a pharmaceutically acceptable excipient.

The pharmaceutical compositions can be made using methods well known to those skilled in the art (See, e.g., *Remington The Science and Practice of Pharmacy* 20$^{th}$ ed. ("Remington"), edited by A. Gennaro, Philadelphia College of Pharmacy and Science 2000 (the contents of which are expressly incorporated herein by reference hereto), p. 858-856).

Accordingly, compositions of ceramide-like glycolipids can be designed for oral, lingual, sublingual, buccal or intrabuccal administration, without undue experimentation, using means well known in the art, for example by combining a ceramide-like glycolipid with an inert diluent or with an edible carrier. The pharmaceutical compositions may be enclosed in gelatin capsules or compressed into tablets. For the purpose of oral therapeutic administration, the pharmaceutical compositions of the present invention may be in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Suitable excipients that can be used in the pharmaceutical compositions of the invention are well known to those skilled in the art (See, Remington). Examples of binders include, but are not limited to, microcrystalline cellulose, gum tragacanth or gelatin. Examples of diluents include, but are not limited to, starch or lactose. Examples of disintegrating agents include, but are not limited to, alginic acid, corn starch and the like. Examples of lubricants include, but are not limited to, magnesium stearate or potassium stearate. An example of a glidant is colloidal silicon dioxide. Examples of sweetening agents include, but are not limited to, sucrose, saccharin and the like. Examples of flavoring agents include, but are not limited to, peppermint, methyl salicylate, orange flavoring and the like. Materials used in preparing these various compositions should be pharmaceutically pure and nontoxic in the amounts used.

The pharmaceutical compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

The pharmaceutical compositions of the present invention can easily be administered rectally. Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the ceramide-like glycolipid in the glycerin, mixing the heated glycerin after which purified water may be added, and pouring the hot mixture into a suppository mold.

The pharmaceutical compositions of the present invention can easily be administered transdermally. Transdermal administration includes percutaneous absorption of the composition through the skin. Transdermal formulations include patches (such as the well-known nicotine patch), ointments, creams, gels, salves and the like.

The present invention includes nasally administering a therapeutically effective amount of the ceramide-like glycolipids. As used herein, nasally administering or nasal administration includes administering the pharmaceutical composition to the mucous membranes of the nasal passage or nasal cavity of the patient. Pharmaceutical compositions for nasal administration of a composition include therapeutically effective amounts of the ceramide-like glycolipids and an excipient and are prepared by well-known methods and adapted to be administered nasally, for example, as a nasal spray, nasal drop, suspension, gel, ointment, cream or powder. Administration of the pharmaceutical composition may also take place using a nasal tampon or nasal sponge.

The ceramide-like glycolipids can also be usefully combined with a CD1d-bearing antigen presenting cell such as a dendritic cell. This mixture would be expected to activate an NK T cell. Accordingly, the invention includes a pharmaceutical composition comprising a ceramide-like glycolipids and a CD1d-bearing antigen presenting cell such as a dendritic cell.

Based on the role of NK T cell activation in induction of memory T and B cells, the skilled artisan would understand that the ceramide-like glycolipids are useful vaccine adjuvants. Thus, in further embodiments, the invention is directed to a pharmaceutical composition comprising a ceramide-like glycolipid wherein the pharmaceutical composition is suitable for use as an adjuvant for a vaccine.

The invention is also directed to methods of administering a vaccine. The methods comprise administering the vaccine in combination with any of the above-described ceramide-like glycolipids.

Based on the role of NK T cell activation in induction of NK cells, the skilled artisan would understand that the ceramide-like glycolipids are useful adjuvants to enhance the effect of passively administered antibodies. Thus, in further embodiments, the invention is directed to a pharmaceutical composition comprising a ceramide-like glycolipid wherein the pharmaceutical composition is suitable for use as an adjuvant for passively administered antibody.

The invention is also directed to methods of administering a therapeutic antibody. The methods comprise administering the antibody in combination with any of the above-described ceramide-like glycolipids.

In one embodiment, the methods of use involve administering the ceramide-like glycolipids to a mammal. In one embodiment, the mammal is a human.

Additionally, the invention is directed to methods of modulating the activity of an NK T cell. The methods comprise contacting a NK T cell with a ceramide-like glycolipid. In one embodiment, the NK T cell exhibits increased production of a cytokine after being contacted with the ceramide-like glycolipids. In one embodiment, the NK T cell exhibits decreased production of a cytokine after being contacted with the ceramide-like glycolipids. The cytokine in these embodiments can be IL-2, IL-4 or IFNγ. Modulation of the NK T cell can be measured by production of a characteristic cytokine, for example IL-2, IL-4 or IFNγ, or increased CD40L expression.

In one embodiment, the NK T cell is in a living mammal. In one embodiment, the animal is a mammal that has, or is at risk for, an autoimmune disease, cancer, or an infection affected by activated NK T cells. In other embodiments, the mammal has, or is at risk for an autoimmune disease such as type 1 diabetes. In these embodiments, the ceramide-like glycolipids can be administered directly to said mammal or first added to dendritic cells ex vivo, then injecting the dendritic cells loaded with the ceramide-like glycolipids into the mammal. In one embodiment, the dendritic cells in these ex vivo embodiments are derived from the same mammal. In one embodiment, the mammal is a human. Methods for combining α-galactosylceramides with dendritic cells ex vivo are well known to those skilled in the art. Any method known to those skilled in the art for combining α-galactosylceramides with dendritic cells ex vivo can be used in the methods of the invention to combine the ceramide-like glycolipids with dendritic cells ex vivo. Representative methodologies include, but are not limited to, those described in D. H. Chang et al., *Sustained expansion of NKT cells and antigen-specific T cells after injection of alpha-galactosyl-ceramide loaded mature dendritic cells in cancer patients*, J Exp Med., May 2, 2005, 201(9):1503-17; S. Fujii et al., *Detection and activation of human Valpha24+ natural killer T cells using alpha-galactosyl ceramide-pulsed dendritic cells*, J Immunol Methods. Jan. 15, 2003; 272(1-2):147-59; and S. Fujii et al., *Prolonged IFN-gamma-producing NKT response induced with alpha-galactosylceramide-loaded DCs*, Nat. Immunol. Sep. 3, 2002, (9):867-74.

The invention is additionally directed to methods of stimulating the immune system in a mammal. The methods comprise administering an effective amount of a ceramide-like glycolipid to a mammal. In one embodiment, an effective amount of a ceramide-like glycolipid to a mammal is administered as a pharmaceutical composition. In one embodiment, the mammal has cancer. In other embodiments, the mammal has type 1 diabetes. In yet other embodiments, the mammal has an inflammatory disease such as rheumatoid arthritis.

In related embodiments, the methods comprise contacting dendritic cells with a ceramide-like glycolipids, then injecting the dendritic cells into the mammal. In one embodiment, the dendritic cells are contacted with a pharmaceutical composition of the ceramide-like glycolipids.

As illustrated in the experiments described in the Example, the ceramide-like glycolipids capable of activating NK T cells vary in the profile of NK T cell induction, depending on the antigen-presenting cell used. For example, some ceramide-like glycolipids are capable of inducing some cytokines in the presence of some antigen-presenting cells but not others. Thus, the ability of a compound, such as an α-galactosylceramide or other α-glycosylceramide, to induce an NK T cell is best measured by using more than one type of antigen presenting cell. Thus, the invention is directed to methods of evaluating a compound for its ability to activate an NK T cell in the presence of a cell expressing a CD1d protein. The methods comprise combining the compound with the NK T cell in the presence of more than one cell type that expresses a CD1d protein and then evaluating whether the NK T cell is activated. The cell type can be, for example, but without limitation, a lymphoid cell, a dendritic cell or an epithelial cell. See Examples. Activation of the NK T cells can be determined by measuring the increase in cytokine production using methods well known to those skilled in the art including, but not limited to, those described herein (See, Examples and data reported in FIGS. 5A and 6).

The test compound can be any compound that would be postulated to bind to CD1d and activate or suppress an NK T cell. Examples include lipotechoic acids, α-galactosylceramides, and other α-glycosylceramides, for example the ceramide-like glycolipids described above.

The invention is further directed to methods of treating a mammal having or at risk for developing an autoimmune disease, cancer, or an infection affected by an activated NK T cell. The invention is further directed to a method of treating or preventing a disorder in a mammal that is affected by modulating the activity of NK T cells. Representative disorders include, but are not limited to, an autoimmune disease, cancer, chronic allergic diseases, or an infection. In one embodiment, the disorder in a mammal is treated or prevented by activating NK T cells. An example is treatment of type I diabetes by activating NK T cells to inhibit the destruction of pancreatic β islet cells. In another embodiment, the disorder in a mammal is treated or prevented by suppressing the activity of NK T cells. An example is treatment of allergic airway hyperreactivity, a model of allergic asthma, by suppressing NK T cells as described in O. Akbari et al., *Essential role of NKT cells producing IL-4 and IL-13 in the development of allergen-induced airway hyperreactivity*, Nature Med, May 2003 9(5):582-588.

In yet another embodiment, the disorder in a mammal is treated or prevented by varying the cytokines produced by the NK T cells to bias the response in favor of type 2 or type I cytokine production. The methods comprise administering to the mammal a ceramide-like glycolipid. In one embodiment, the ceramide-like glycolipid is administered as a pharmaceutical composition. In one embodiment, the mammal has or is at risk for an autoimmune disease, for example type 1 diabetes, myasthenia gravis, pemphigus vulgaris, systemic lupus erythematosus, Guillain-Barre syndrome, antiphospholipid syndrome, Goodpasture syndrome, graft vs. host disease, multiple sclerosis, primary biliary cirrhosis, scleroderma, vasculitis, vitiligo, Wegener's granulomatosis, rheumatoid arthritis, glomerulo-nephritis, idiopathic thrombocytopenia purpura, psoriasis, or Sjogen's disease. In one embodiment, the autoimmune disease is type 1 diabetes. In one embodiment, the disorder is a chronic allergic disease such as asthma or atopic dermatitis. As with other embodiments described above, the pharmaceutical composition may be administered directly to the mammal by a method described above or first added to dendritic cells ex vivo followed by injection of the dendritic cells into the mammal.

The amount of the ceramide-like glycolipid that is effective in the treatment or prevention of a disorder can be determined by standard clinical techniques. In addition, in vitro or in vivo assays can optionally be employed to help identify optimal dosage ranges. The precise dose to be employed will also depend on the route of administration, and the seriousness of the disorder being treated and should be decided according to the judgment of the practitioner and each patient's circumstances in view of, e.g., published clinical studies. Suitable effective dosage amounts, however, typically range from about 1 micrograms to about 10,000 micrograms per kilogram of body weight weekly although they are typically about 1,000 micrograms or less per kilogram of body weight weekly. In one embodiment, the effective dosage amount ranges from about 10 to about 5,000 micrograms per kilogram of body weight weekly. In another embodiment, the effective dosage amount ranges from about 50 to about 1,000 micrograms per kilogram of body weight weekly. In another embodiment, the effective dosage amount ranges from about 75 to about 500 micrograms per kilogram of body weight weekly. The effective dosage amounts described herein refer to total amounts administered, that is, if more than one ceramide-like glycolipid is administered, the effective dosage amounts correspond to the total amount administered. The ceramide-like glycolipid can be administered as a single weekly dose or as divided doses.

The ceramide-like glycolipid can be assayed in vitro or in vivo for the desired therapeutic or prophylactic activity prior to use in humans. Animal model systems can be used to demonstrate safety and efficacy.

Embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

EXAMPLES

Amino Substituted Derivatives of α-galactosylceramides and Other α-Glycosylceramides as Modulators of Immunity and Autoimmunity Production and identification of novel amino substituted forms of α-galactosylceramide with immunomodulatory activities. The discovery of OCH and its enhanced properties at preventing autoimmune tissue damage provided a strong stimulus for our group to undertake the evaluation of a larger number of analogues based on the KRN7000 structure. The strategy we chose was to develop analogues based on modifications or substitutions of the amino-linked fatty acid chain of KRN7000. This choice was guided by two considerations. First of all, some work had already begun on modification of the sphingosine base by other investigators with the discovery of OCH, so this area was not entirely novel. See, also, U.S. Pat. No. 5,936,076. In contrast, very little previous work had appeared on modifications of the fatty acid chain. Fatty acid chain length variations were studied by Kawano, et al. (1997), but this analysis was very limited and not revealing of any interesting properties. Also, efficient methods of producing these compounds has been developed.

Using these methods, we produced more than 60 novel amino substituted analogues of KRN7000. These were screened in a functional assay that assessed the ability of the compounds to activate NK T cell hybridomas in the presence of various types of cells expressing CD1d, or in the presence of recombinant CD1d proteins bound to the tissue culture plate surface (FIG. 5).

The ability of the compounds to activate NK T cell hybridomas in the presence of various types of cells expressing CD1d reported in FIG. 5A was determined using a murine NK T cell hybridoma stimulation assay. CD1d-transfected RMA-S cells were plated at 50,000 cells/well in flat-bottom tissue culture plates in 100 microliters complete medium containing varying concentrations of ceramide-like glycolipids for 6 h at 37° C. The plates were then centrifuged (430 g, 3 min), and cells washed with PBS three times. Fifty thousand NKT hybridoma cells (clone DN3A4.1-2) were then added in 100 microliters of medium for a 12 h stimulation. Cell-free supernatants were collected at the end of incubation and assayed for IL-2 by standard capture ELISA. Relative potencies of the ceramide-like glycolipids were calculated from the reciprocal effective concentrations at half-maximal response ($1/EC_{50}$), and expressed as units by normalization to the observed potency for KRN7000. The structure of the ceramide-like glycolipids are provided in FIG. 5B.

The results of these screening assays revealed that between 5-10% of the analogues in our collection had potency equal to or greater than that of KRN7000 (potency was defined by the molar concentration required to give a half maximal response of the NK T cell hybridomas). In the representative assay shown in FIG. 5A, seven compounds showed substantially greater potency than KRN7000. In addition, several of these compounds with elevated potency also showed increased maximal activity when compared to KRN7000 (defined as the highest level of response achieved in the assay over the range of compound dilutions tested; data not shown).

Table 1 shows results from the proliferation assay, IL-4 assay, and IFNγ assay for compounds YTCO3-42 to YTCO3-61, showing variability in their ability to induce proliferation and induce the two cytokines, as well as the ratio of IL-4 to IFNγ. FIG. 5C shows a graphical representation of the results reported in Table 1 for cytokine response. Table I and FIG. 5C shows that cytokine production by normal mouse splenocytes is stimulated with ceramide-like glycolipids. The cytokine response reported in Table 1 and FIG. 5C was determined by the following procedure: Bulk splenocytes from C57BL/6 mice were plated at 300,000 per well in 96-well flat-bottom tissue culture plates with ceramide-like glycolipids diluted to a concentration of 500 nM in 200 microliters complete medium. After 48 h at 37° C., 150 microliters of supernatant was removed for cytokine measurements. Supernatant levels of IL-4, and IFNγ were measured by standard enzyme-linked immunosorbent assay (ELISA), using capture and biotinylated detection antibody pairs (clones 11B11/BVD6-24G2-biotin, and R4-6A2/XMG1.2-biotin, respectively, from BD Pharmingen, San Diego, Calif.). Cytokine content was revealed using streptavidin-horseradish peroxidase (Zymed, South San Francisco, Calif.) with TMB-Turbo substrate (Pierce, Rockford, Ill.) or alternatively with streptavidin-alkaline phosphatase (Zymed) with 4-nitrophenyl phosphate disodium hexahydrate substrate (Sigma-Aldrich, St. Louis, Mo.) and read at 450 or 405 nm, respectively, on a microplate reader (Titertek, Huntsville, Ala.). Standards for IL-4 and IFNγ were from Peprotech (Rocky Hill, N.J.).

Table 1 shows stimulation of CD1d-dependent proliferation by compounds YTCO3-42 to YTCO3-61. The results were obtained using a splenocyte proliferation assay according to the following procedure: Bulk splenocytes from C57BL/6 mice were plated at 300,000 per well in 96-well flat-bottom tissue culture plates with the indicated ceramide-like glycolipid diluted in complete medium to the concentrations shown. After 48 h at 37° C., the plate wells were pulsed with 20 microliters of medium containing 50 microCi/ml $^3$H-thymidine and incubated for a further 18 h. Cell proliferation was estimated by harvesting pulsed cells onto 96-well filtermats and scintillation counting on a 1450 Microbeta Trilux instrument (Wallac/Perkin Elmer, Boston, Mass.). FIG. 5D shows stimulation of CD1d-dependent proliferation by DB02-1, an α-glucosyl ceramide identical to DB01-1 except that a glucose replaces the galactose of DB01-1. The results reported in FIG. 5D were obtained by the same method used to obtain the data for proliferation provided in Table 1.

TABLE 1

$EC_{50}$ is the concentration of glycolipid that gave a 50% maximal response in proliferation of splenocyte cultures as measured by $^3$H-thymidine incorporation. Higher $EC_{50}$ values thus represent lower potency for stimulation of NKT cell dependent proliferation. IL-4 and IFNγ levels were measured by ELISA in culture supernatants of splenocyte cultures stimulated for 48 hours with 500 nM of each glycolipid. Cytokine concentrations are in ng/ml. ND indicates below the reliable level for detection by the assay. The values in parentheses are the IL-4/IFNγ ratios for each compound divided by this ratio for the KRN7000-like DB01-1 compound.

| COMPOUND | Proliferation $EC_{50}$ (nM) | Cytokine Response | | |
|---|---|---|---|---|
| | | IL-4 | IFNγ | ratio IL-4/IFNγ |
| DB01-1 | 63.6 | 0.19 | 7.29 | 0.026 (1.0) |
| YTCO3-42 | >2500 | ND | ND | — |
| YTCO3-43 | 86.9 | 0.35 | 19.50 | 0.018 (0.7) |
| YTCO3-44 | 57.1 | 1.38 | 14.19 | 0.097 (3.7) |
| YTCO3-45 | 222.3 | 0.63 | 15.26 | 0.041 (1.6) |
| YTCO3-46 | 4.8 | 0.22 | 8.52 | 0.026 (1.0) |
| YTCO3-47 | 7.5 | 0.21 | 19.63 | 0.011 (0.4) |
| YTCO3-48 | 86.9 | 0.20 | 12.56 | 0.016 (0.6) |
| YTCO3-49 | 57.1 | 0.13 | 4.57 | 0.028 (1.1) |
| YTCO3-50 | 5.4 | 0.07 | 9.47 | 0.007 (0.3) |
| YTCO3-51 | 63.8 | 0.05 | 9.03 | 0.006 (0.2) |
| YTCO3-52 | 17.0 | 0.19 | 10.25 | 0.019 (0.7) |
| YTCO3-53 | 38.0 | 0.02 | 0.67 | 0.030 (1.2) |
| YTCO3-54 | 17.2 | 0.11 | 10.39 | 0.011 (0.4) |
| YTCO3-55 | 675.0 | ND | ND | — |
| YTCO3-56 | 11.4 | 0.22 | 11.79 | 0.019 (0.7) |
| YTCO3-57 | 2188.9 | ND | ND | — |
| YTCO3-58 | 51.8 | 0.21 | 8.64 | 0.024 (0.9) |
| YTCO3-59 | 0.1 | 1.77 | 0.22 | 8.045 (309.4) |
| YTCO3-60 | 10.9 | 0.18 | 8.18 | 0.022 (0.8) |
| YTCO3-61 | 72.4 | 0.17 | 7.50 | 0.023 (0.9) |

Structure/activity relationships of the analogues. The compounds of greatest interest to emerge from the screening assays fall mainly into two general categories. They are either α-galactosylceramides containing truncated fatty acyl chains with various degrees of unsaturations, or α-galactosylceramides with aromatic rings in their amide linked branch. Our results indicate that these alterations in the amino substitution of KRN7000 can have at least three possible effects on the biological activity of the compounds: 1) change in potency/activity, 2) change in the type of cell that presents the compound efficiently, and 3) change in the outcome of NK T cell activation in terms of the types of cytokines produced. Illustrative examples of these effects are provided by the figures that follow.

Figure 6:
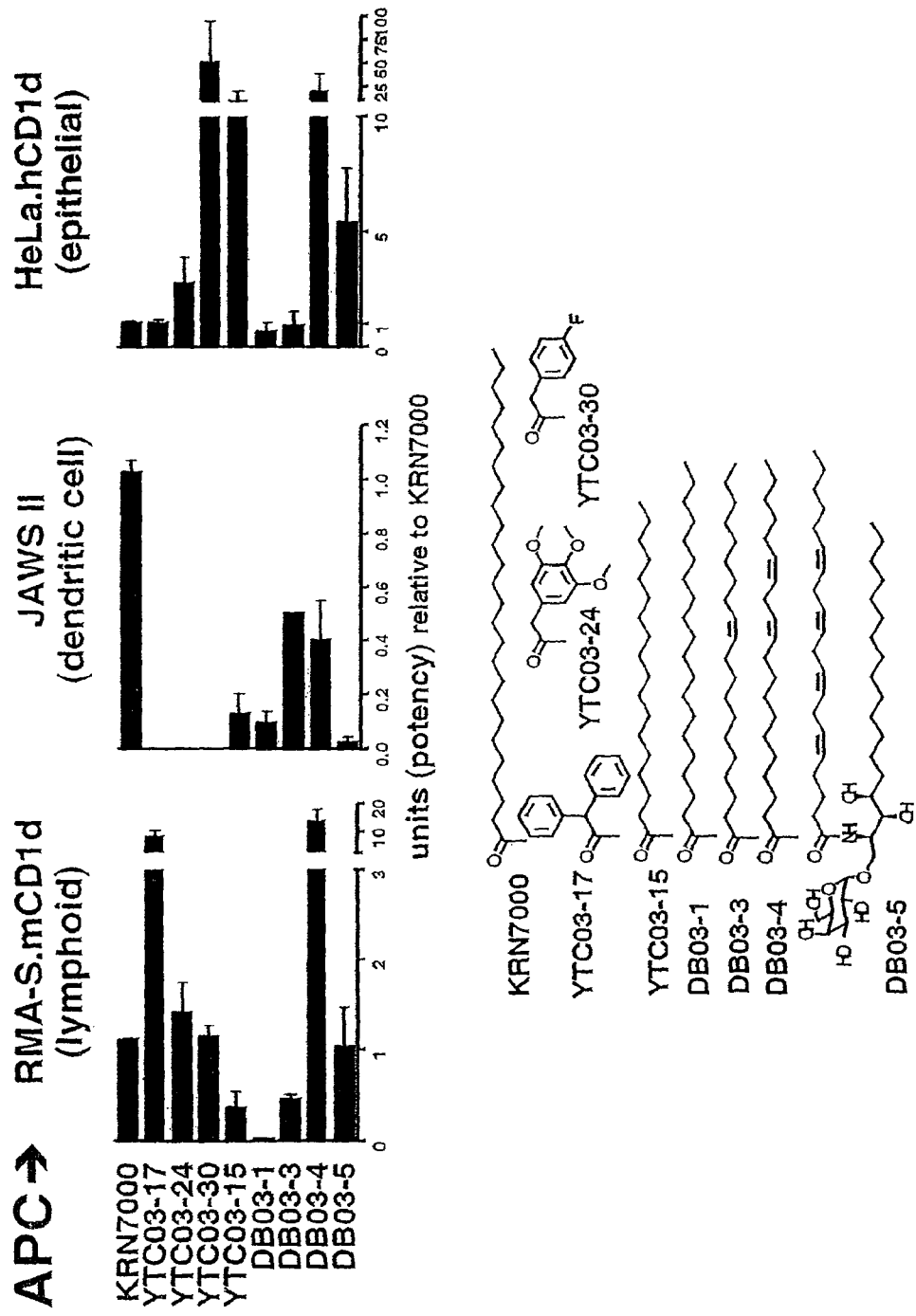
FIG. 6 shows experimental results of the differential presentation of ceramide-like glycolipids by various presenting cell types. IL-2 production by NK T hybridoma DN32.D3 in response to eight selected ceramide-like glycolipids is shown, using three different cell types as antigen presenting cells (APCs) (top). Structures of the amino linked side chains in each of the ceramide-like glycolipids used in this experiment are shown on the bottom.

FIG. 6 shows the differential presentation of various potent ceramide-like glycolipids when different types of antigen presenting cells (APCs) are used in the NK T cell activation assay. IL-2 production by NK T hybridoma DN32D3 in response to eight selected ceramide-like glycolipids, was determined using three different cell types as antigen presenting cells. RMA-S.mCD1d are a mouse lymphoma line that has been transfected to express murine CD1d. JAWS II is a mouse dendritic cell line that naturally expresses mouse CD1d. HeLa.hCD1d is a human cervical carcinoma cell line that has been transfected to express human CD1d. The assay was performed in the same manner as described above for the results depicted in FIG. 5A.

Note, for example, that YTC03-17 is markedly more potent than KRN7000 when the compounds are presented by CD1d molecules expressed on a lymphoid cell line (RMA-S), whereas these two compounds are presented about equally by CD1d molecules expressed on a epithelial tumor cell line (HeLa). When a dendritic cell line (JAWS-II) is used as the antigen presenting cell, there is very little or no response at all to YTC03-17. In addition to demonstrating that a biphenyl substitution can generate an active compound, these studies show that the activity is markedly dependent on the type of cell which bears the CD1d on which the compound is presented.

FIG. 6 also shows additional phenyl containing analogues that displayed enhanced potency in some assays. Again the results are quite dependent on the type of antigen presenting cell used. Note for example that YTC03-30 has extraordinary potency when presented by HeLa cells (at least 100 fold greater than KRN7000), but similar potency to KRN7000 when presented by RMA-S cells.

Figure 7:
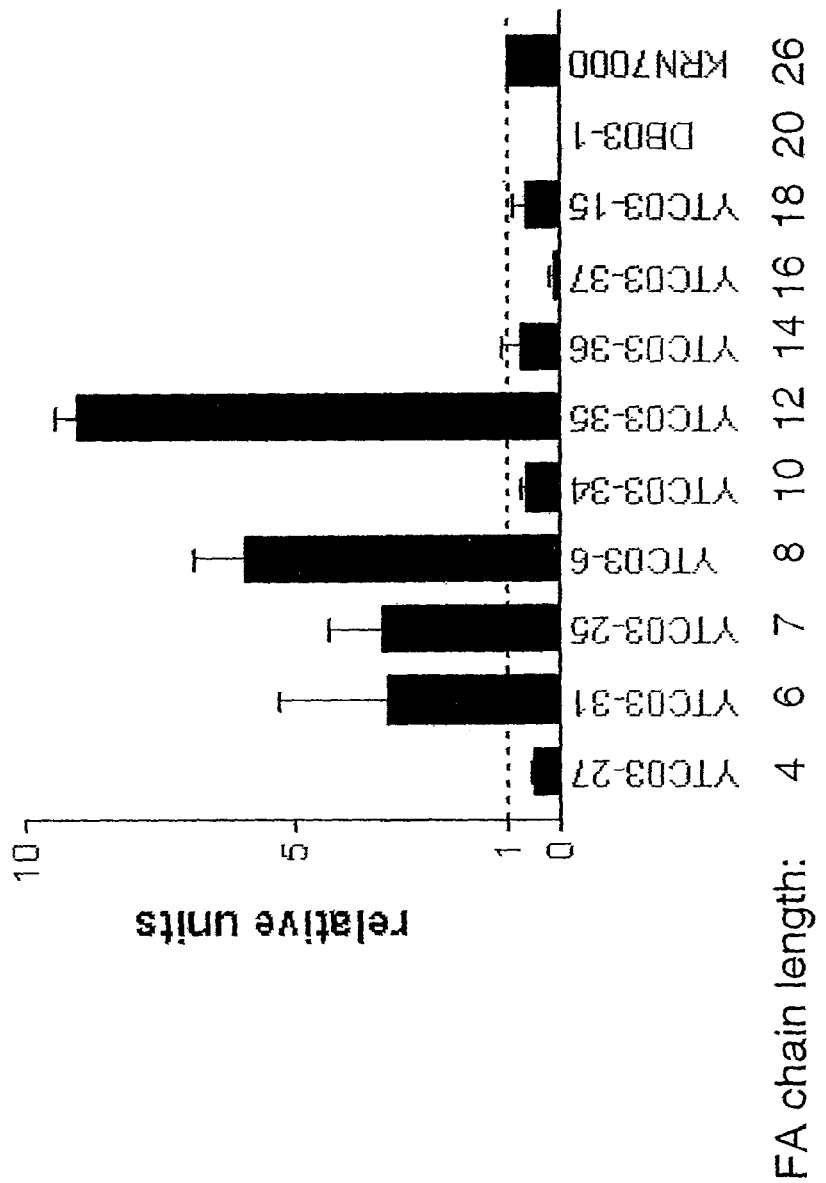
FIG. 7 shows the effects of fatty acid chain length on the potency of ceramide-like glycolipids. Ceramide-like glycolipids with the indicated chain lengths were tested for stimulation of NK T hybridoma DN32.D3 using RMA-S/CD1d as antigen presenting cells (APCs).
Figure 8:
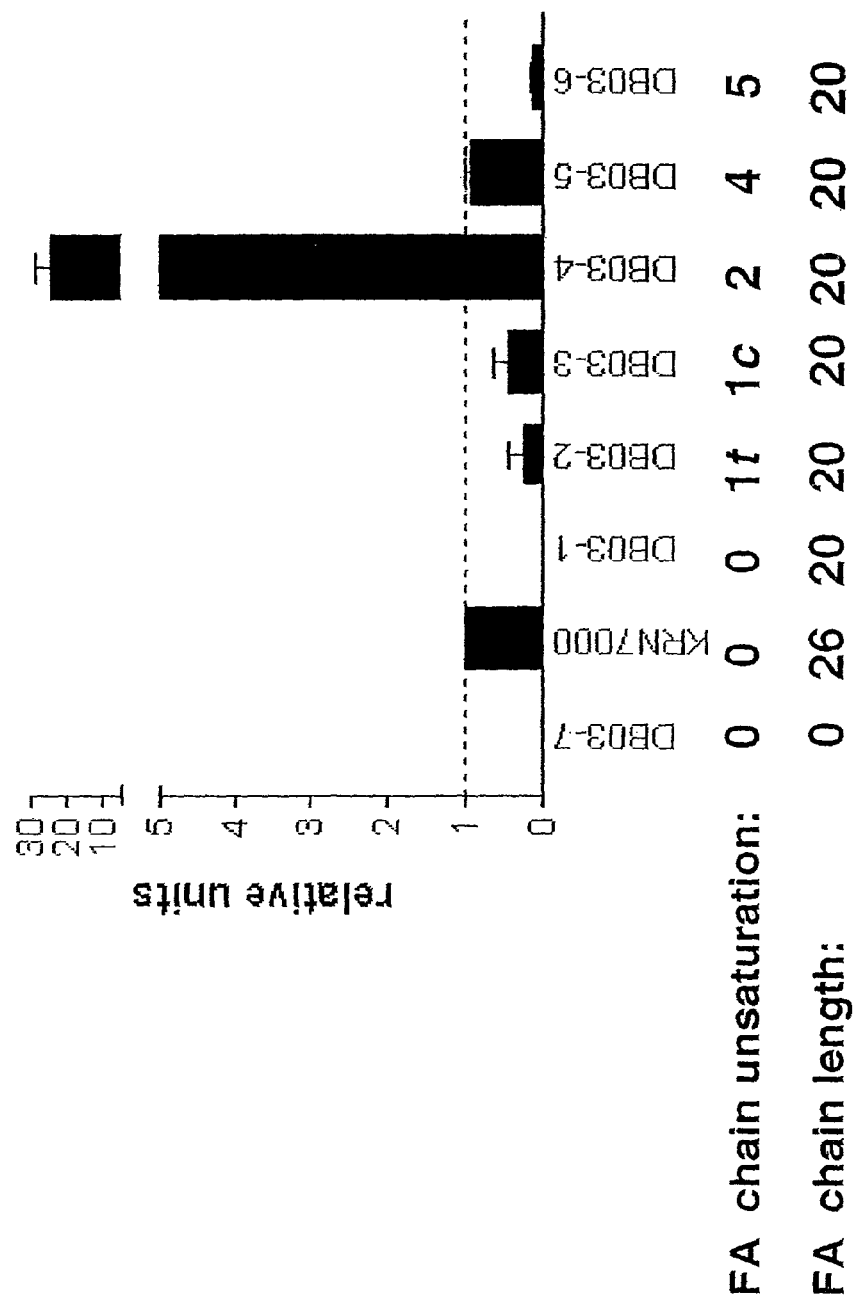
FIG. 8 shows the effects of fatty acid chain unsaturations on potency of C20 FA ceramide-like glycolipids. Ceramide-like glycolipids with the indicated chain lengths and indicated numbers of double bonds were tested for stimulation of NK T hybridoma DN32.D3 as in FIG. 7.

FIG. 7 shows effects of varying the length of the N-linked fatty acid when the fatty acid chain is fully saturated. Note that there appears to be a clear influence of chain length on potency, with optimal activity occurring at a length of C12 in this particular system. How this effect will be influenced by changing the nature of the antigen-presenting cell remains to be investigated. FIG. 8 shows the effects of introducing unsaturations into the fatty acid chain when the fatty acid length is held constant at C20. A dramatic effect on potency is observed, with a diunsaturated analogue (DB03-4) having extremely enhanced potency. Again, how this effect will be influenced by changing the nature of the antigen-presenting cell remains to be investigated. The relative potency of each analogue was determined by measuring L-2 production by mouse NK T cell hybridoma DN3A4.1-2 as described above for the results depicted in FIG. 5A.

FIG. 8 shows the effects of fatty acid chain unsaturations on potency of C20 fatty acid ceramide-like glycolipids. The ceramide-like glycolipids with the indicated chain lengths and indicated numbers of double bonds were tested for stimulation of NK T hybridoma DN32.D3 by measuring IL-2 production by mouse NK T cell hybridoma DN3A4.1-2 as described above for the results depicted in FIG. 7.

Figure 9:
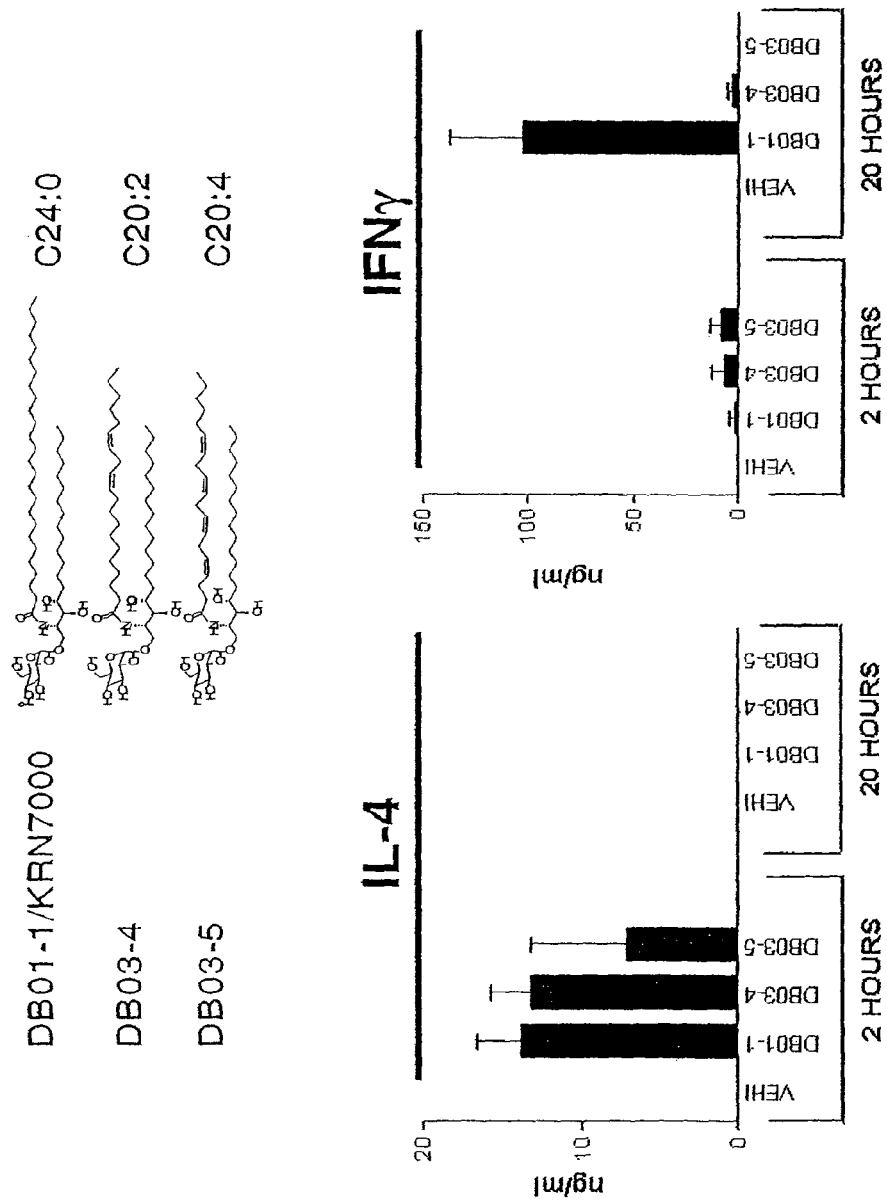
FIG. 9 shows the selective stimulation of IL-4 production in vivo in mice by ceramide-like glycolipids DB03-4 and DB03-5. Serum levels of L-4 and IFNγ after a single injection of DB01-1, DB03-4, or DB03-5 are shown. C57BL/6 mice (11-13 weeks old) were given a single i.p. injection of 4.8 nanomoles of the compounds or phosphate buffered saline (PBS)/vehicle control. Serum cytokine levels were measured 2 and 20 hours later by capture ELISA. Bars show means of three mice, with standard deviation. Note that DB01-1 has nearly identical structure to KRN7000 (C24 fatty acid as compared to C26) and has activity that is indistinguishable from KRN7000 in multiple bioassays. We use DB01-1 as a "KRN7000 mimic" because it has been synthesized by our group and is readily available for our studies, and KRN7000 was unavailable due to license restrictions.

A most intriguing property of KRN7000 analogues is that in some cases they may elicit immune responses that are qualitatively different from those that occur following stimulation with the parent compound. This was shown to be the case with the sphingosine chain length variant OCH, as published by Yamamura and colleagues (Miyamoto et al., 2001). In that case, it was shown that OCH elicited a selective production of interleukin-4 (IL-4) when administered in vivo to mice, and failed to stimulate the strong production of interferon-γ (IFNγ) that is observed after injection of KRN7000. This selective activation of IL-4 production by NK T cells was proposed to be the basis for the enhanced therapeutic effects of OCH in the EAE model of central nervous system autoimmune disease. We have observed a similar in vivo effect on the nature of the NK T cell response using several of our ceramide-like glycolipids. As shown in FIG. 9, two of the ceramide-like glycolipids containing unsaturated C20 fatty acids (DB03-4 and DB03-5) elicit a strong IL-4 response two hours after injection into mice. These responses are similar to those seen for DB01-1, an analogue that is structurally almost identical to KRN7000 (C24 fatty acid instead of C26, otherwise identical) and indistinguishable in terms of its activity in our hands. However, while DB01-1 also evokes a strong IFNγ response at 20 hours post injection, this late wave of IFNγ is not seen with the two C20 ceramide-like glycolipids. This selective IL-4 induction is virtually identical to that reported for the OCH analogue, and thus illustrates the potential for amino substituted analogues of KRN7000 to induce qualitatively different immunomodulatory effects in vivo. The results reported in FIG. 9 were obtained by measuring serum levels of IL-4 and IFNγ after administering a single injection of DB00-1, DB03-4, or DB03-5 to C57BL/6 mice. C57BL/6 mice (11-13 weeks old) were given a single i.p. injection of 4.8 nanomoles of the ceramide-like glycolipids or PBS/vehicle control. Serum cytokine levels were measured 2 and 20 hours later by capture ELISA. Bars show means of three mice, with standard deviation.

Figure 11:
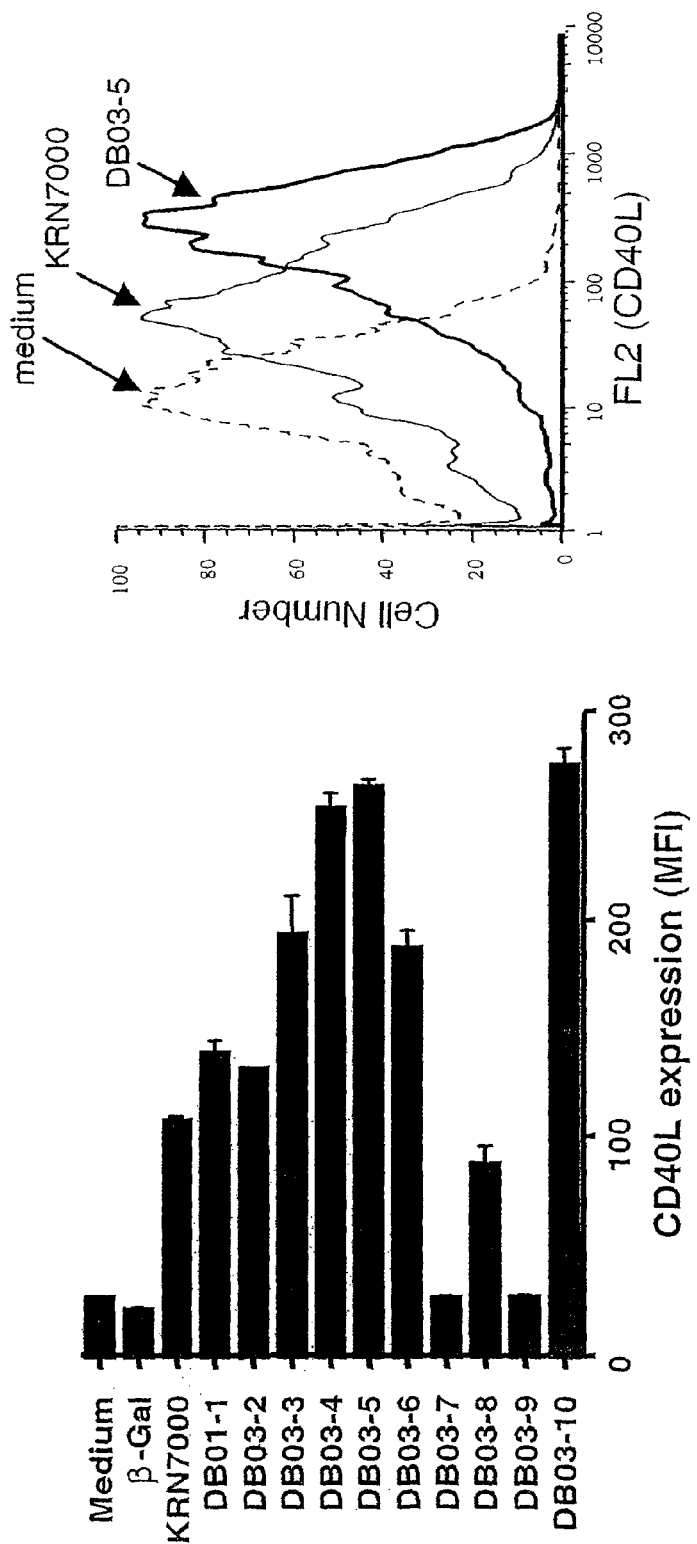
FIG. 11 shows graphs of experimental results showing that various ceramide-like glycolipids of the present invention can stimulate expression of CD40L (CD154).

FIG. 11, shows the differential effect of various KRN7000 analogs in stimulating CD40L expression. FIG. 11 also shows that the galactose moiety of these ceramide compounds can be replaced with another monosaccharide while still retaining some activity, since DB03-8, which has a fucose replacing the galactose, was capable of inducing CD40L. The upregulation of CD40L by ceramide-like glycolipids reported in FIG. 11 were obtained by incubating NK T hybridoma DN3A4.1-2 with RMA-S/CD1d cells at a ratio of 2:1 in the presence of 0.5 uM of ceramide-like glycolipid for 18 hours. Cells were then resuspended and labeled with mAbs specific for CD5 and CD40L. Levels of CD40L were determined by FACS analysis of the population gated for CD5 staining.

See also FIG. 5D, showing stimulation of CD1d-dependent proliferation by the α-glucosylceramide DB02-1. DB02-1 also stimulated significant cytokine production, including both IFNγ and IL-4. Interestingly, while IFNγ levels produced in response to DB02-1 in in vitro splenocyte cultures were markedly lower than those stimulated by DB01-1 at all concentrations of the analogs, the IL-4 levels were nearly equivalent at doses of 100 μM or greater. This suggests that DB02-1 is an NKT cell agonist with the potential to stimulate a TH2-biased cytokine response.

Figure 10:
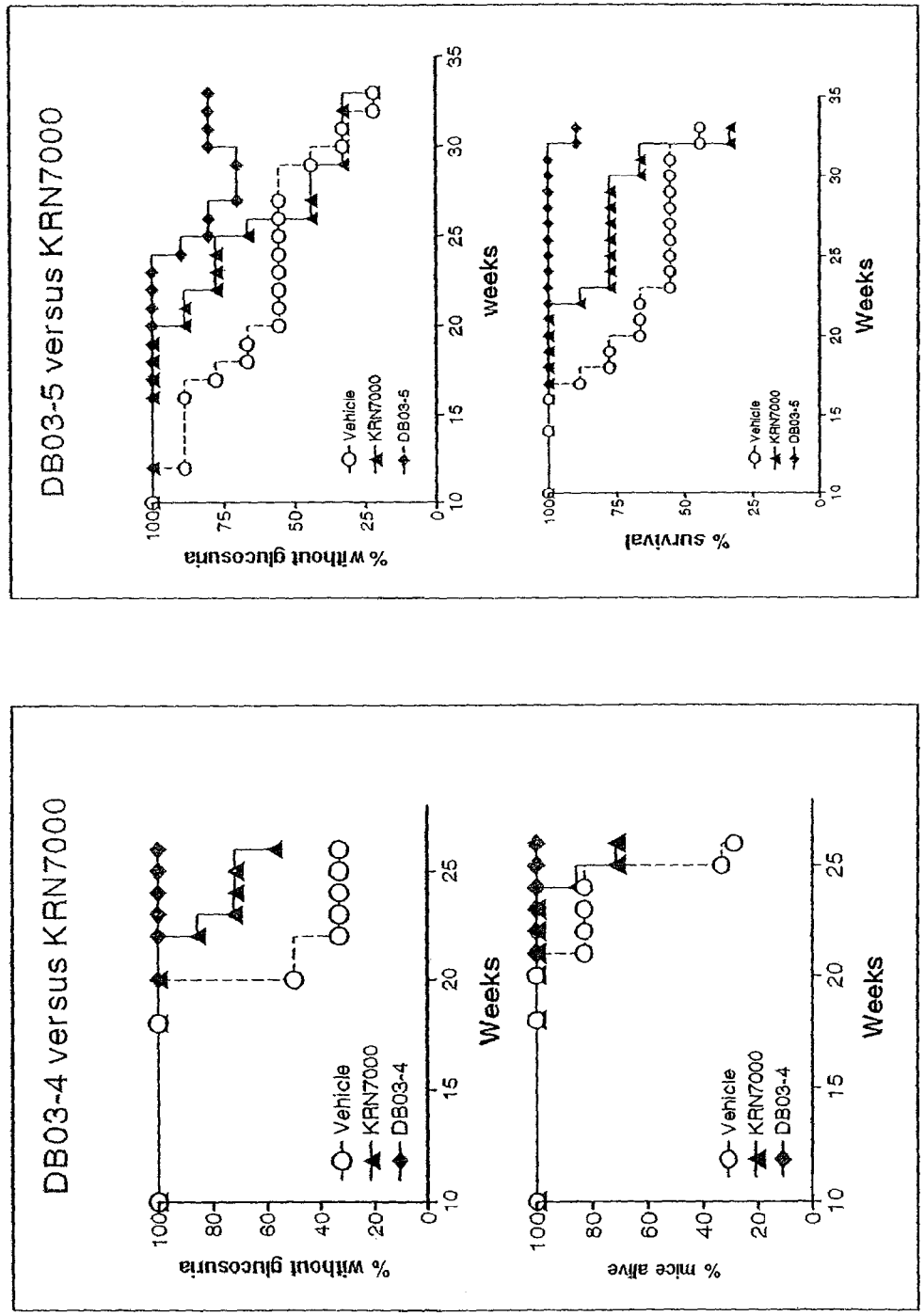
FIG. 10 shows experimental results establishing that DB03-4 and DB03-5 are superior to KRN7000 for prevention of diabetes in NOD mice. Cohorts of 6-8 female NOD mice were treated with placebo (vehicle) or DB01-1 (indicated as KRN7000), DB03-4 or DB03-5 injections once weekly beginning at 4-5 weeks of age. Treatment was discontinued after 5 injections (DB03-4) or 7 injections (DB03-5). Top graphs show incidence of glycosuria, and bottom graphs show survival in each cohort.

Given the widely held belief that selective augmentation of IL-4 production can be protective or therapeutic in the setting of many autoimmune diseases, we have initiated studies to examine the efficacy of compounds such as DB03-4 and DB03-5 in diabetes prone NOD mice. This work indicates that our ceramide-like glycolipids are superior to KRN7000 and the KRN7000-mimic DB01-1 in the prevention of diabetes in NOD mice (FIG. 10). FIG. 10 shows that type 1 diabetes can be delayed or prevented in NOD mice treated with ceramide-like glycolipids. The results reported in FIG. 10 were obtained by treating three groups, each consisting of 9-12 female NOD mice, starting from age 5 weeks with a ceramide-like glycolipid. The indicated ceramide-like glycolipids (DB03-4, DB03-5, or KRN7000) were injected i.p. once per week in a dose of 200 micrograms/kg. Treatment was discontinued at 11 weeks of age, and the mice were monitored weekly for glucosuria (top) and death (bottom).

For experiments involving in vivo treatment of mice with the ceramide-like glycolipids, the ceramide-like glycolipids were administered by i.p. or i.v. injection in 0.2 ml PBS+ 0.025% Tween-20, or in vehicle alone. A typical dose is about 4-5 nmoles per animal per injection. Representative references for administering an α-galactosyl ceramide to mice by i.p., i.v. or p.o. routes are S. Sharif et al., *Activation of natural killer T cells by alpha-galactosylceramide treatment prevents the onset and recurrence of autoimmune Type 1 diabetes*, Nat. Med., Sep. 7, 2001, (9):1057-62 and K. Miyamoto et al., *A synthetic glycolipid prevents autoimmune encephalomyelitis by inducing TH2 bias of natural killer T cells*, Nature. Oct. 4, 2001, 413(6855):5314.

Compounds DB04-1 (KRN-7000), DB05-9, DB05-10, DB05-11, DB05-12, DB05-14, DB05-15, DB05-16, and DB05-17 were also tested for their ability to induce proliferation and to induce the cytokines IFNγ and IL-4. Each of these compounds of the invention has conjugated double bonds in R1. The ability to induce the cytokines IFNγ and IL-4 was determined using the same IFNγ assay and IL-4 assay as described above for compounds YTC03-42 to YTC03-61. The ability of these compounds to induce proliferation was determined using the same splenocyte proliferation assay described above for compounds YTC0342 to YTC03-61.

Figure 12:
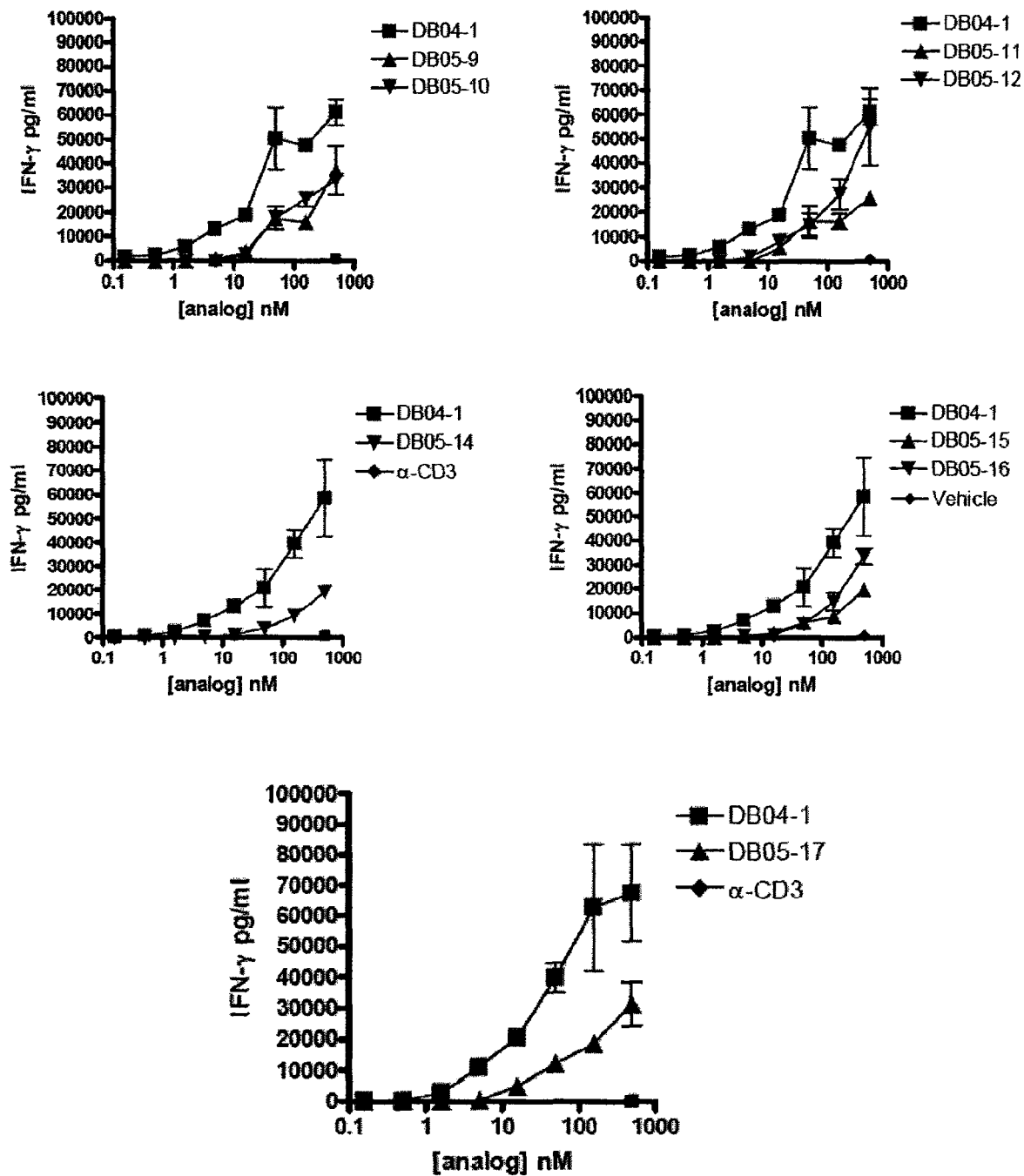
FIG. 12 is a graphical representation showing IFNγ induction by DB04-1 (KRN-7000), DB05-9, DB05-10, DB05-11, DB05-12, DB05-14, DB05-15, DB05-16, and DB05-17, determined as described in the experimental section.
Figure 13:
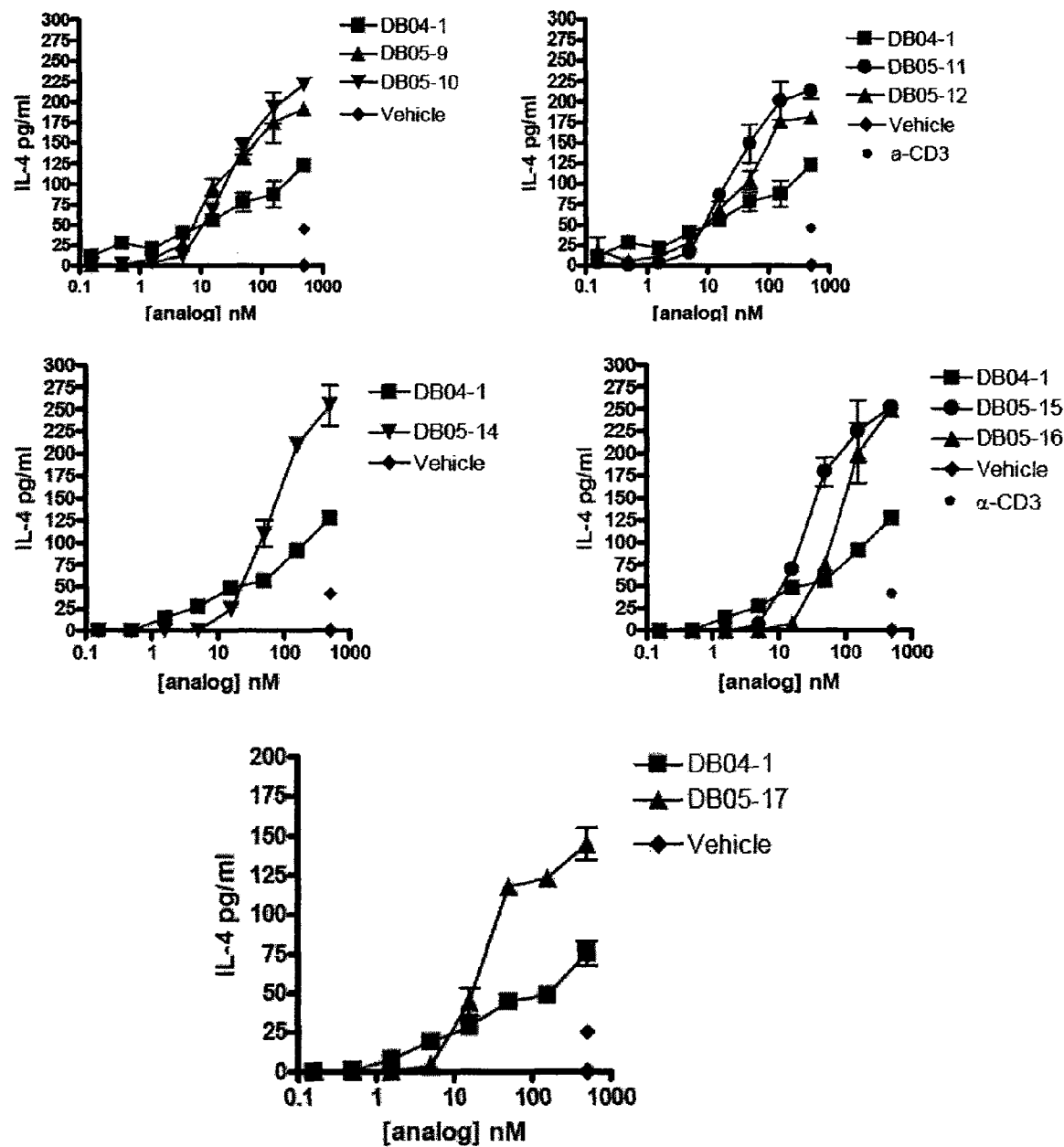
FIG. 13 is a graphical representation showing IL-4 induction by DB04-1 (KRN-7000), DB05-9, DB05-10, DB05-11, DB05-12, DB05-14, DB05-15, DB05-16, and DB05-17, determined as described in the experimental section.
Figure 14:
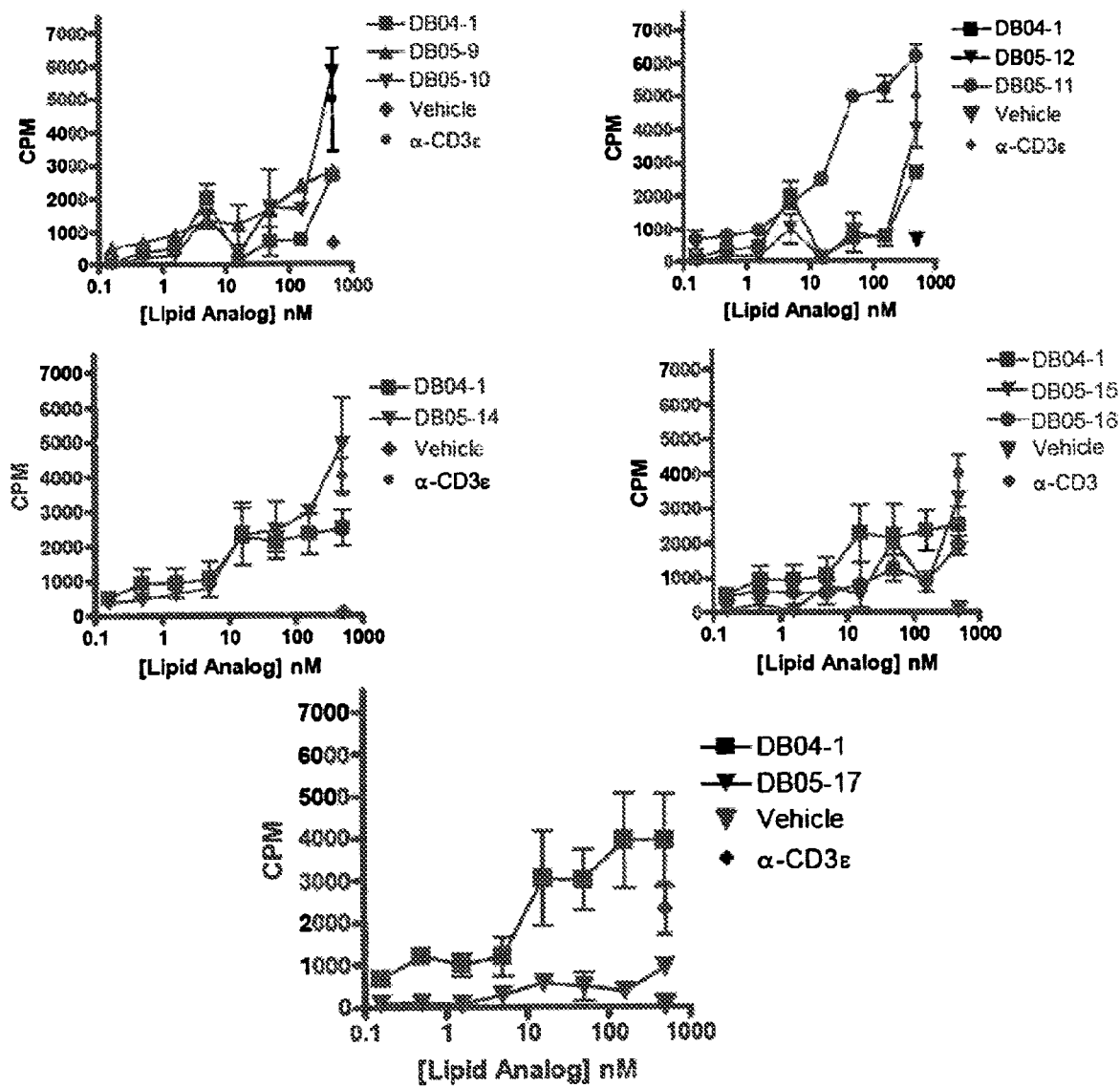
FIG. 14 is a graphical representation showing the stimulation of CD1d-dependent proliferation by DB04-1 (KRN-7000), DB05-9, DB05-10, DB05-11, DB05-12, DB05-14, DB05-15, DB05-16, and DB05-17 as described in the experimental section.

FIG. 12 shows results from the IFNγ assay and FIG. 13 shows the results from IL-4 assay for compounds DB04-1 (KRN-7000), DB05-9, DB05-10, DB05-11, DB05-12, DB05-14, DB05-15, DB05-16, and DB05-17. FIG. 14 shows stimulation of CD1d-dependent proliferation by each of these compounds, determined as described above.

Figure 15:
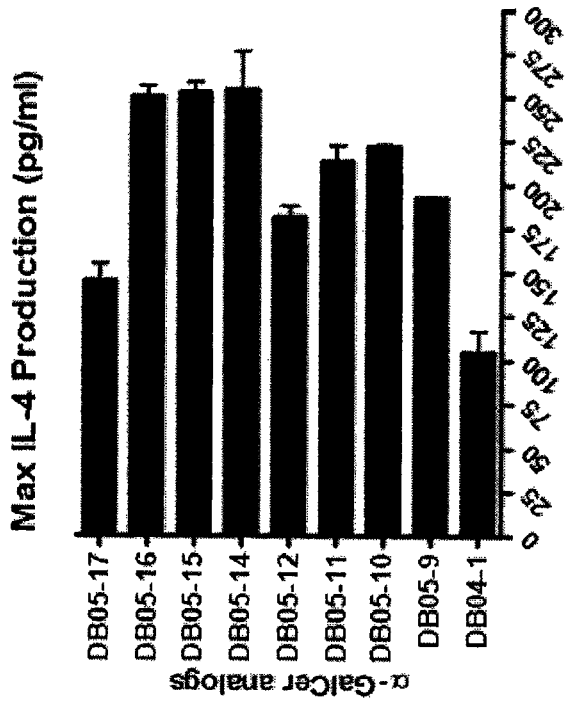
FIG. 15 is a graphical representation of maximum IFNγ production and maximum IL-4 production when cells are treated with 500 nm of DB04-1 (KRN-7000), DB05-9, DB05-10, DB05-11, DB05-12, DB05-14, DB05-15, DB05-16, and DB05-17 as described in the experimental section.
Figure 15:
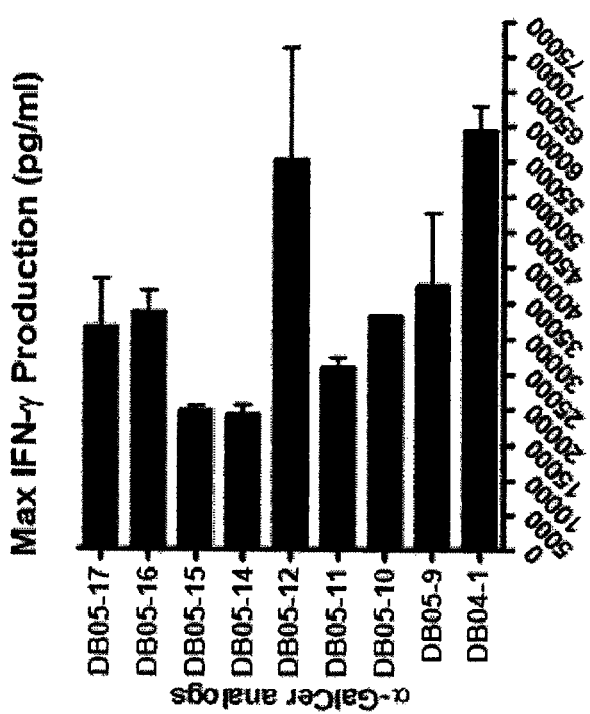

FIG. 15 shows maximum IFNγ production and maximum IL-4 production when cells are treated with 500 nM of DB04-1 (KRN-7000), DB05-9, DB05-10, DB05-11, DB05-

Figure 16:
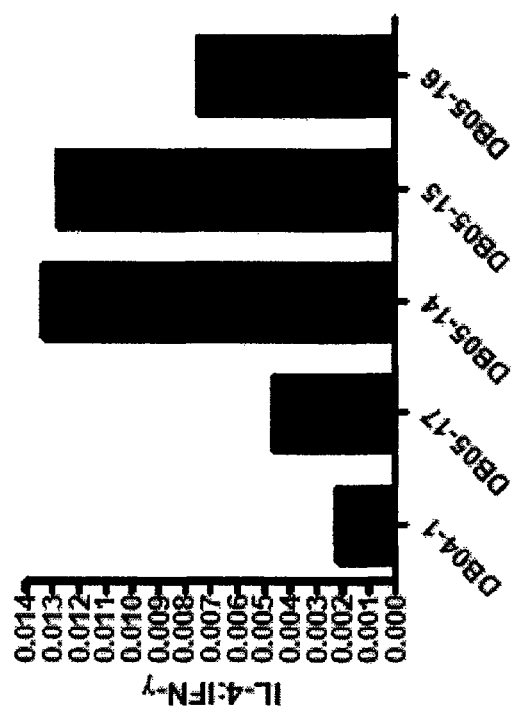
FIG. 16 is a graphical representation of the ratio of IL-4 production to IFNγ production for compounds DB04-1 (KRN-7000), DB05-9, DB05-10, DB05-11, DB05-12, DB05-14, DB05-15, DB05-16, and DB05-17 as described in the experimental section.
Figure 16:
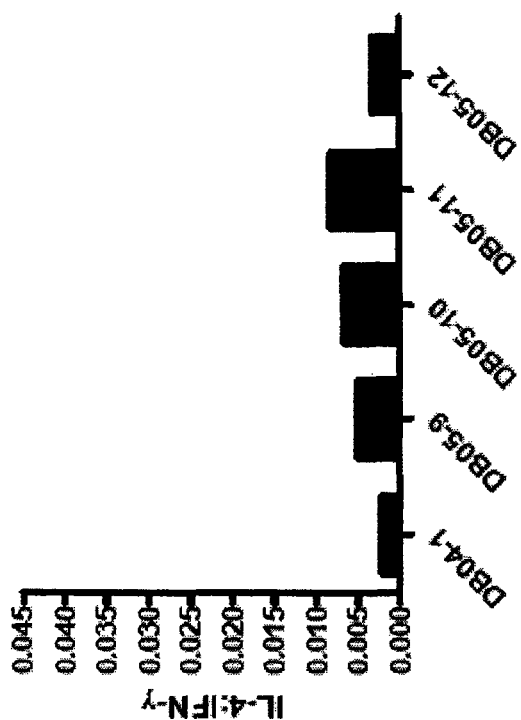

12, DB05-14, DB05-15, DB05-16, or DB05-17 and FIG. 16 shows the ratio of IL-4 production to IFNγ production for each of these compounds.

These results demonstrate that these compounds of the invention, with conjugate double bonds, can stimulate greater proliferative and functional activity of NKT cells than KRN-7000. Also, in some cases the compounds show a bias for high secretion levels of IL-4 relative to IFNγ.

These studies have identified a panel of novel immunologically active analogues of αGalCer. These compounds differ significantly in structure from the previously studied and well-documented prototype in this family, KRN7000. We have already demonstrated a number of important properties for certain analogues that would make them superior agents for a variety of applications in the prevention and treatment of disease. These compounds are also useful as adjuvants for stimulation of responses to vaccines, for immunotherapy against allergic diseases, and for the treatment of cancer.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of activating a NK T cell, the method comprising contacting the NK T cell with an α-galactosylceramide of Formula I:

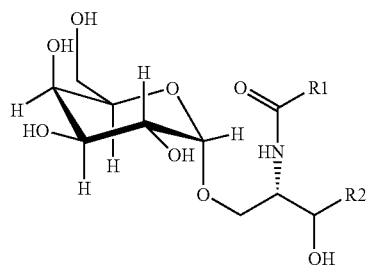

Formula I wherein
R1 is a linear or branched $C_2$-$C_{27}$ alkene with at least two C=C bonds wherein R1 includes at least two C=C bonds that are conjugated with each other; and
R2 is —CH(OH)(CH$_2$)$_x$CH$_3$,
wherein X is an integer ranging from 5-17.

2. The method of claim 1, wherein the NK T cell exhibits increased production of a cytokine after contacting with the α-galactosylceramide.

3. The method of claim 2, wherein the cytokine is selected from the group consisting of IL-2, IL-4, and IFNγ.

4. The method of claim 1, wherein the NK T cell exhibits increased CD40L expression after contacting with the α-galactosylceramide.

5. The method of claim 1, wherein the NK T cell is in a living mammal.

6. The method of claim 5, wherein the mammal has, or is at risk for developing, an autoimmune disease, cancer, or an infection.

7. The method of claim 5, wherein the mammal has or is at risk for developing type 1 diabetes.

8. A method of activating a NK T cell, the method comprising contacting the NK T cell with an α-galactosylceramide of Formula I:

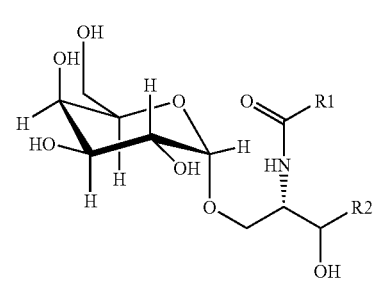

Formula I wherein
R1 is a linear or branched $C_2$-$C_{27}$ alkene with at least two C=C bonds; and
R2 is one of the following (a)-(c):
(a) —CH(OH)(OH)(CH$_2$)$_x$CH$_3$,
(b) —CH(OH)(CH$_2$)$_x$CH(CH$_1$)$_2$,
(c) —CH(OH)(CH$_1$)$_x$CH(CH$_3$)CH$_2$CH$_3$,
wherein X is an integer ranging from 5-17,
wherein the NK T cell is in a living mammal, and
wherein the α-galactosylceramide is contacted with dendritic cells ex vivo before the α-galactosylceramide is contacted with the NK T cell and then injecting the dendritic cells into the mammal.

9. The method of claim 8, wherein the dendritic cells are derived from the mammal.

10. A method of activating a NK T cell, the method comprising contacting the NK T cell with an α-galactosylceramide of Formula I:

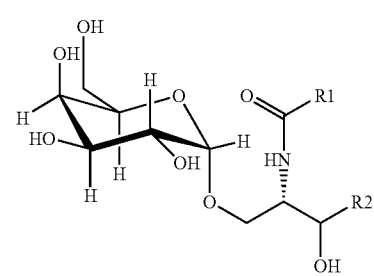

Formula I wherein
R1 is C(OH)—R3 where R3 is a linear or branched $C_2$-$C_{26}$ alkene; and
R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 5-17.

11. The method of claim 10, wherein the NK T cell exhibits increased production of a cytokine after contacting with the α-galactosylceramide.

12. The method of claim 11, wherein the cytokine is selected from the group consisting of IL-2, IL-4, and IFNγ.

13. The method of claim 10, wherein the NK T cell exhibits increased CD40L expression after contacting with the α-galactosylceramide.

14. The method of claim 10, wherein the NK T cell is in a living mammal.

15. The method of claim 14, wherein the mammal has, or is at risk for developing, an autoimmune disease, cancer, or an infection.

16. The method of claim 14, wherein the mammal has or is at risk for developing type 1 diabetes.

17. The method of claim 14, further comprising contacting the α-galactosylceramide with dendritic cells ex vivo before the α-galactosylceramide is contacted with the NK T cell and then injecting the dendritic cells into the mammal.

18. The method of claim 17, wherein the dendritic cells are derived from the mammal.

19. A method of activating a NK T cell, the method comprising contacting the NK T cell with an α-galactosylceramide comprising Formula I:

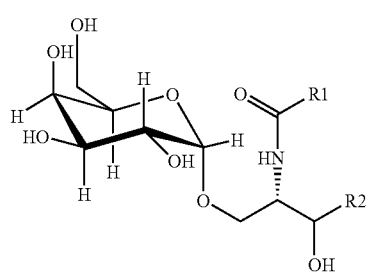

Formula I wherein

R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; and R2 is one of the following (a)-(e):

(a) —$CH_2(CH_2)_X CH_3$,
(b) —$CH(OH)(CH_2)_X CH_3$,
(c) —$CH(OH)(CH_2)_X CH(CH_3)_2$,
(d) —$CH$=$CH(CH_2)_X CH_3$,
(e) —$CH(OH)(CH_2)_X CH(CH_3)CH_2 CH_3$, wherein X is an integer ranging from 5-17.

20. The method of claim 19, wherein the NK T cell exhibits increased production of a cytokine after contacting with the α-galactosylceramide.

21. The method of claim 20, wherein the cytokine is selected from the group consisting of IL-2, IL-4, and IFNγ.

22. The method of claim 19, wherein the NK T cell exhibits increased CD40L expression after contacting with the α-galactosylceramide.

23. The method of claim 19, wherein the NK T cell is in a living mammal.

24. The method of claim 23, wherein the mammal has, or is at risk for developing, an autoimmune disease, cancer, or an infection.

25. The method of claim 23, wherein the mammal has or is at risk for developing type 1 diabetes.

26. The method of claim 23, further comprising contacting the α-galactosylceramide with dendritic cells ex vivo before the α-galactosylceramide is contacted with the NK T cell and then injecting the dendritic cells into the mammal.

27. The method of claim 26, wherein the dendritic cells are derived from the mammal.

28. A method of activating a NK T cell, the method comprising contacting the NK T cell with an α-galactosylceramide comprising Formula I:

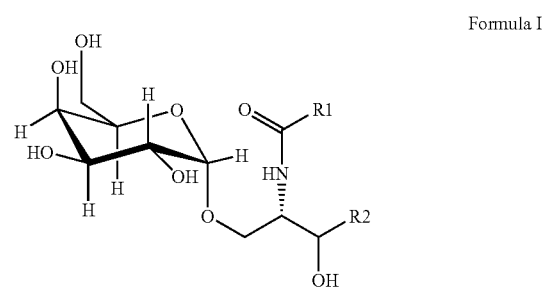

Formula I wherein

R1 is selected from the group consisting of —C(=O)OCH$_2$CH$_3$, —(CH$_2$)$_6$CH$_3$, —(CH$_2$)$_4$Cl, —(CH$_2$)$_{16}$CH$_3$, —(CH$_2$)$_5$CH$_3$, —(CH$_2$)$_2$CH$_3$, —(CH$_2$)$_4$CH$_3$, —(CH$_2$)$_8$CH$_3$, —(CH$_2$)$_{10}$CH$_3$, and —(CH$_2$)$_{12}$CH$_3$; and R2 is —CH(OH)(CH$_2$)$_{13}$CH$_3$.

29. The method of claim 28, wherein the NK T cell exhibits increased production of a cytokine after contacting with the α-galactosylceramide.

30. The method of claim 29, wherein the cytokine is selected from the group consisting of IL-2, IL-4, and IFNγ.

31. The method of claim 28, wherein the NK T cell exhibits increased CD40L expression after contacting with the α-galactosylceramide.

32. The method of claim 28, wherein the NK T cell is in a living mammal.

33. The method of claim 32, wherein the mammal has, or is at risk for developing, an autoimmune disease, cancer, or an infection.

34. The method of claim 32, wherein the mammal has or is at risk for developing type 1 diabetes.

35. The method of claim 32, further comprising contacting the α-galactosylceramide with dendritic cells ex vivo before the α-galactosylceramide is contacted with the NK T cell and then injecting the dendritic cells into the mammal.

36. The method of claim 35, wherein the dendritic cells are derived from the mammal.

37. The method of claim 10, wherein R1 includes at least two C=C bonds.

38. The method of claim 37, wherein R1 includes at least two C=C bonds that are conjugated with each other.

39. The method of claim 19, wherein R1 includes at least two C=C bonds.

40. The method of claim 39, wherein R1 includes at least two C=C bonds that are conjugated with each other.

41. The method of claim 1, wherein R2 is —CH(OH)(CH$_2$)$_{13}$CH$_3$.

42. The method of claim 1, wherein the α-galactosylceramide having the following formula:

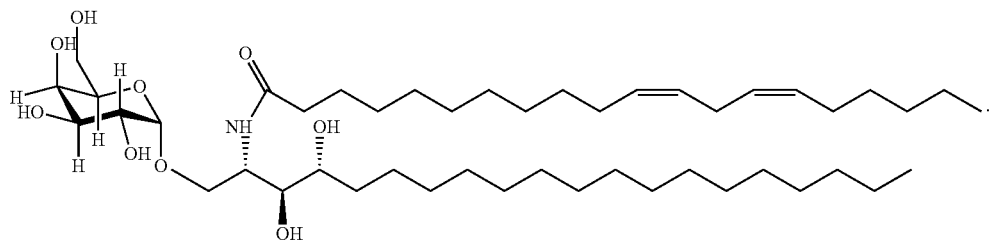

43. The method of claim 1, wherein the α-galactosylceramide having the following formula:

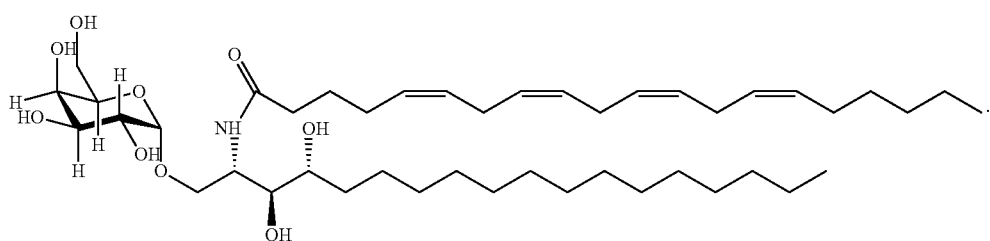

44. A method of activating a NK T cell, the method comprising contacting the NK T cell with an α-galactosylceramide comprising Formula I:

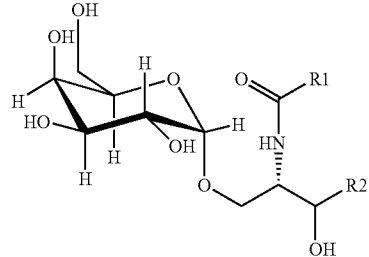

Formula I wherein
R1 is selected from the group consisting of

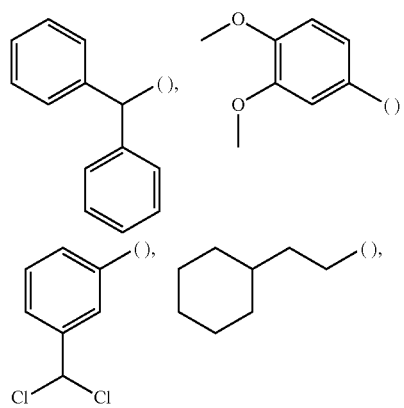

-continued

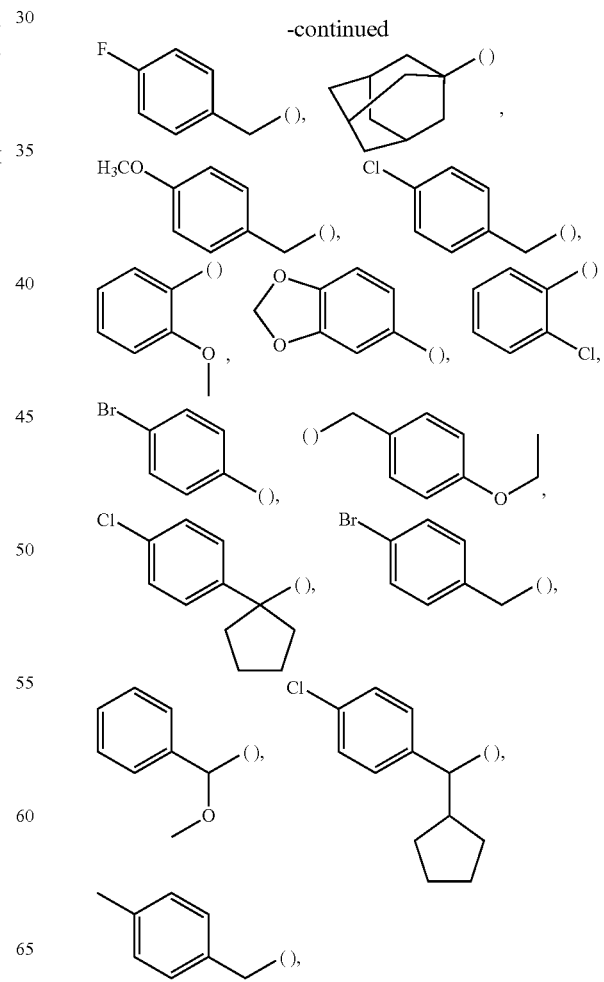

where ( ) represent the point of attachment of R1 to the compound of Formula I; and R2 is one of the following (a)-(e):
(a) —CH$_2$(CH$_2$)$_X$CH$_3$,
(b) —CH(OH)(CH$_2$)$_X$CH$_3$,
(c) —CH(OH)(CH$_2$)$_X$CH(CH$_3$)$_2$,
(d) —CH=CH(CH$_2$)$_X$CH$_3$,
(e) —CH(OH)(CH$_2$)$_X$CH(CH$_3$)CH$_2$CH$_3$,
wherein X is an integer ranging from 5-17.

45. The method of claim 44, wherein the NK T cell exhibits increased production of a cytokine after contacting with the α-galactosylceramide.

46. The method of claim 45, wherein the cytokine is selected from the group consisting of IL-2, IL-4, and IFNγ.

47. The method of claim 44, wherein the NK T cell exhibits increased CD40L expression after contacting with the α-galactosylceramide.

48. The method of claim 44, wherein the NK T cell is in a living mammal.

49. The method of claim 48, wherein the mammal has, or is at risk for developing, an autoimmune disease, cancer, or an infection.

50. The method of claim 48, wherein the mammal has or is at risk for developing type 1 diabetes.

51. The method of claim 48, further comprising contacting the α-galactosylceramide with dendritic cells ex vivo before the α-galactosylceramide is contacted with the NK T cell and then injecting the dendritic cells into the mammal.

52. The method of claim 51, wherein the dendritic cells are derived from the mammal.

53. An α-galactosylceramide of Formula I:

wherein
R$_1$ is a linear or branched C$_2$-C$_{27}$ alkene with at least two C=C bond, wherein said at least two C=C bonds are conjugated with each other, or R$_1$ is C(OH)—R$_3$, wherein R3 is a linear or branched C$_2$-C$_{26}$ alkene with at least two C=C bond, and wherein said at least two C=C bonds are conjugated with each other; and R2 is one of the following (a)-(e):
(a) —CH$_2$(CH$_2$)$_X$CH$_3$,
(b) —CH(OH)(CH$_2$)$_X$CH$_3$,
(c) —CH(OH)(CH$_2$)$_X$CH(CH$_3$)$_2$,
(d) —CH=CH(CH$_2$)$_X$CH$_3$,
(e) —CH(OH)(CH$_2$)$_X$CH(CH$_3$)CH$_2$CH$_3$,
wherein X is an integer ranging from 5-17.

54. The α-galactosylceramide of claim 53, wherein R2 is —CH(OH)(CH$_2$)$_{13}$CH$_3$.

* * * * *

UNITED STATES PATENT AND TRADEMARK OFFICE
CERTIFICATE OF CORRECTION

| | | |
|---|---|---|
| PATENT NO. | : 8,022,043 B2 | Page 1 of 1 |
| APPLICATION NO. | : 11/785988 | |
| DATED | : September 20, 2011 | |
| INVENTOR(S) | : Steven A. Porcelli | |

It is certified that error appears in the above-identified patent and that said Letters Patent is hereby corrected as shown below:

IN THE SPECIFICATION

Column 1, lines 16-18, delete "Portions of this work were supported by grants from the National Institutes of Health. The government may have certain rights in this invention." and insert -- This invention was made with government support under grant number AI045889 awarded by NIH. The government has certain rights in the invention. --

Signed and Sealed this
First Day of December, 2015

Michelle K. Lee
*Director of the United States Patent and Trademark Office*